United States Patent
Marchetto et al.

(10) Patent No.: US 9,696,297 B2
(45) Date of Patent: Jul. 4, 2017

(54) METHOD FOR PREPARING AN X CHROMOSOME INACTIVATED FEMALE HUMAN NEURAL CELL

(75) Inventors: Maria C. N. Marchetto, La Jolla, CA (US); Fred H. Gage, La Jolla, CA (US); Alysson R. Muotri, La Jolla, CA (US)

(73) Assignee: SALK INSTITUTE FOR BIOLOGICAL STUDIES, La Jolla, CA (US)

( * ) Notice: Subject to any disclaimer, the term of this patent is extended or adjusted under 35 U.S.C. 154(b) by 924 days.

(21) Appl. No.: 13/518,842

(22) PCT Filed: Dec. 23, 2010

(86) PCT No.: PCT/US2010/062080
§ 371 (c)(1),
(2), (4) Date: Jun. 22, 2012

(87) PCT Pub. No.: WO2011/079307
PCT Pub. Date: Jun. 30, 2011

(65) Prior Publication Data
US 2013/0004985 A1    Jan. 3, 2013

Related U.S. Application Data

(60) Provisional application No. 61/289,863, filed on Dec. 23, 2009.

(51) Int. Cl.
*C12N 5/079* (2010.01)
*G01N 33/50* (2006.01)

(52) U.S. Cl.
CPC ..... *G01N 33/5058* (2013.01); *G01N 2800/28* (2013.01)

(58) Field of Classification Search
CPC .............. G01N 2800/28; G01N 33/5058
See application file for complete search history.

(56) References Cited

U.S. PATENT DOCUMENTS

| 2009/0047263 A1* | 2/2009 | Yamanaka et al. ........ 424/93.21 |
| 2009/0136456 A1 | 5/2009 | Huang et al. |
| 2010/0184051 A1* | 7/2010 | Hochedlinger et al. .......... 435/6 |

FOREIGN PATENT DOCUMENTS

CA        2683056 A1 *  10/2008

OTHER PUBLICATIONS

Hotta et al. "Isolation of human iPS cells using EOS lentiviral vectors to select for pluripotency." Nature Methods (May 2009); 6: pp. 370-376.*
Hoffbuhr et al. "Associations between MeCP2 mutations, X-chromosome inactivation, and phenotype." Ment Retard Dev Disabil Res Rev. 2002;8(2):99-105.*
Lewitzky et al. "Reprogramming somatic cells towards pluripotency by defined factors." Curr Opin Biotechnol. Oct. 2007;18(5):467-73.*
Niwa et al. "Quantitative expression of Oct-3/4 defines differentiation, dedifferentiation or self-renewal of ES cells." Nat Genet. Apr. 2000;24(4):372-6.*
Kim et al. "Direct reprogramming of mouse fibroblasts to neural progenitors." Proc. Natl. Acad Sci U S A. May 10, 2011;108(19):7838-43. Epub Apr. 26, 2011.*
Yamanaka, S. "Induction of pluripotent stem cells from mouse fibroblasts by four transcription factors." Cell Prolif. Feb. 2008;41 Suppl 1:51-6.*
Stadtfeld et al. "Induced pluripotent stem cells generated without viral integration." Science. Nov. 7, 2008;322(5903):945-949. 1162494. Epub Sep. 25, 2008.*
Okita et al. "Generation of mouse induced pluripotent stem cells without viral vectors." Science. Nov. 7, 2008;322(5903):949-53. 1164270. Epub Oct. 9, 2008.*
Gonzalez et al. "Generation of mouse-induced pluripotent stem cells by transient expression of a single nonviral polycistronic vector." Proc. Natl. Acad. Sci.Okita U S A. Jun. 2, 2009;106(22):8918-22. Epub May 19, 2009.*
Minks et al. "A skewed view of X chromosome inactivation." J. Clin. Invest. (2008);118(1):pp. 20-23.*
Makedonski et al. "MeCP2 deficiency in Rett syndrome causes epigenetic aberrations at the PWS/AS imprinting center that affects UBE3A expression." Hum Mol Genet. Apr. 15, 2005;14(8):1049-58. Epub Mar. 9, 2005.*
Jensen et al. "Strengths and Limitations of the Neurosphere Culture System." Mol Neurobiol. Dec. 2006;34(3):153-61.*
Esch et al. "A unique Oct4 interface is crucial for reprogramming to pluripotency." Nat Cell Biol. Mar. 2013;15(3):295-301.*
Bain et al. "Embryonic stem cells express neuronal properties in vitro." Dev Biol. Apr. 1995;168(2):342-57.*
Luikenhuis et al. "Expression of MeCP2 in postmitotic neurons rescues Rett syndrome in mice." Proc Natl Acad Sci U S A. Apr. 20, 2004;101(16):6033-8.*
Amir, et al., "Rett Syndrome: Methyl-CpG-Binding protein 2 mutations and phenotype-genotype correlations", *American Journal of Medical Genetics*, 97:147-152 (2000).
Amir, et al., "Rett syndrome is caused by mutations in X-linked MECP2, encoding methyl-CpG-binding protein 2", *Nature Genetics*, 23:185-188 (1999).
Ballas, et al., "Non-cell autonomous influence of MeCP2-deficient glia neuronal dendritic morphology", *Nature Neuroscience*, 12(3):311-317 (2009).
Chahrour, et al., "Material for MeCP2, a key contributor to neurological disease, activates and represses transcription", *Science*, 320:1224-1229 (2008).
Chahrour, et al., "Supporting Online Material for MeCP2, a key contributor to neurological disease, activates and represses transcription", *Science*, 320: 208 pages (2008).
Chao, et al., "MeCP2 controls excitatory synaptic strength by regulating glutamatergic synapse number", *Neuron*, 56:58-65 (2007).
Chao, et al., "MeCP2 controls excitatory synaptic strength by regulating glutamatergic synapse number", *Neuron*, 56:58-65 (2007) (Supplemental Data).

(Continued)

Primary Examiner — Titilayo Moloye
(74) Attorney, Agent, or Firm — Baker Botts L.L.P.

(57) ABSTRACT

Provided herein are methods and compositions useful in treating neurological disorders.

4 Claims, 38 Drawing Sheets

(56) References Cited

OTHER PUBLICATIONS

Chapleau, et al., "Dendritic spine pathologies in hippocampal pyramid neurons from Rett syndrome brain and after expression of Rett-associated MECP2 mutations", *Neurobiology of Disease*, 35:219-233 (2009).
Collins, et al., "Mild overexpression of MeCP2 causes a progressive neurological disorder in mice", *Human Molecular Genetics*, 13(21):2679-2689 (2004).
Collins, et al., "Mild overexpression of MeCP2 causes a progressive neurological disorder in mice", *Human Molecular Genetics*, 13(21):2679-2689 (Supplemental Captions) (2004).
Collins, et al., "Mild overexpression of MeCP2 causes a progressive neurological disorder in mice", *Human Molecular Genetics*, 13(21):2679-2689 (Supplemental Figure 1) (2004).
Collins, et al., "Mild overexpression of MeCP2 causes a progressive neurological disorder in mice", *Human Molecular Genetics*, 13(21):2679-2689 (Supplemental Figure 2) (2004).
Collins, et al., "Mild overexpression of MeCP2 causes a progressive neurological disorder in mice", *Human Molecular Genetics*, 13(21):2679-2689 (Supplemental Figure 3) (2004).
Collins, et al., "Mild overexpression of MeCP2 causes a progressive neurological disorder in mice", *Human Molecular Genetics*, 13(21):2679-2689 (Supplemental Table 1) (2004).
Courchesne, et al., "Evidence of brain overgrowth in the first year of life in Autism", *JAMA*, 290(3):337-344 (2003).
De Filippis, et al., "Early postnatal behavioral changes in the Mecp2-308 truncation mouse model of Rett syndrome", *Genes, Brain and Behavior*, 9:213-223 (2010).
Dhara, et al., Gene trap as a tool for genome annotation and analysis of X chromosome inactivation in human embryonic stem cells, *Nucleic Acids Research*, 32(13):3998-4002 (2004).
Dimos, et al., "Induced pluripotent stem cells generated from patients with ALS can be differentiated into motor neurons", *Science*, 321:1218-1221 (2008).
Ebert, et al., "Induced pluripotent stem cells from a spinal muscular atrophy patient", *Nature*, 457:277-280 (2009).
Giacometti, et al., "Partial rescue of MeCP2 deficiency by postnatal activation of MeCP2", *PNAS*, 104(6):1931-1936 (2007).
Hagberg, et al., "Head growth in Rett syndrome", *Brian & Development*, 23:S227-S229 (2001).
Hammer, et al., "The phenotypic consequences of MECP2 mutations extend beyond Rett syndromw", *Mental Retardation and Developmental Disabilities Research Reviews*, 8:94-98 (2002).
Hotta, et al., "Isolation of human iPS cells using EOS lentiviral vectors to select for pluripotency", *Nature Methods*, 6(5):370-376 (2009).
Hotta, et al., "Isolation of human iPS cells using EOS lentiviral vectors to select for pluripotency", *Nature Methods*, 6(5):370-376 (Supplemental Figures and Text) (2009).
Kishi, et al., "MeCP2 functions largely cell-autonomously, but also non-cell-autonomously, in neuronal maturation and dendritic arborization of cortical pyramidal neurons", *Experimental Neurology*, 222:51-58 (2010).
Laccone, et al., "Mutation spectrum in patients with Rett syndrome in the German population: Evidence of hot spot regions", *Human Mutation*, 17:183-190 (2001).
Lee, et al., "Modelling pathogenesis and treatment of familial dysautonomia using patient-specific iPSCs", *Nature*, 461:402-406 (2009).
Lee, et al., "Modelling pathogenesis and treatment of familial dysautonomia using patient-specific iPSCs", *Nature*, 461:402-406 (Supplemental Data) (2009).
Maezawa, et al., Rett syndrome astrocytes are abnormal and spread MeCP2 deficiency through gap junctions, *The Journal of Neuroscience*, 29(16):5051-5061 (2009).
Maezawa, et al., Rett syndrome astrocytes are abnormal and spread MeCP2 deficiency through gap junctions, *The Journal of Neuroscience*, 29(16):5051-5061 (Supplemental Material) 2009.
Maherali, et al., "Directly reprogrammed fibroblasts show global epigenetic remodeling and widespread tissue contribution", *Cell Stem Cell*, 1:55-70 (2007).
Marchetto, et al., "A model for neural development and treatment of Rett syndrome using human induced pluripotent stem cells", *Cell*, 143:527-239 (2010).
Marchetto, et al., "Non-cell-autonomous effect of human SOD1$^{G37R}$ astrocytes on motor neurons derived from human embryonic stem cells", *Cell Stem Ceel*, 3:649-657 (2008).
Mironov, et al., "Remodelling of the respiratory network in a mouse model of Rett syndrome depends on brain-derived neurotrophic factor regulated slow calcium buffering", *J. Physiol.*, 11:2473-2485 (2009).
Muotri, "Modeling epilepsy with pluripotent human cells", *Epilepsy & Behavior*, 14:81-85 (2009).
Park, et al., "Disease-specific induced pluripotent stem cells", *Cell*, 134:877-886 (2008).
Ramocki, et al., "Autism and other neuropsychiatric symptoms are prevalent in individuals with MECP2 duplication syndrome", *Ann. Neurol.*, 66:771-782 (2009).
Samaco, et al., "Epigenetic overlap in autism-spectrum neurodevelopmental disorders: MECP2 deficiency causes reduced expression of UBE3A and GABRB3", *Human Molecular Genetics*, 14(4):483-492 (2005).
Samaco, et al., "Multiple pathways regulate MeCP@ expression in normal brain development and exhibit defects in autism-spectrum disorders", *Human Molecular Genetics*, 13(6):629-639 (2004).
Santos, et al., "Evidence for abnormal early development in a mouse model of Rett syndrome", *Genes, Brain and Behavior*, 6:277-286 (2007).
Soldner, et al., "Parkinson's disease patient-derived induced pluripotent stem cells free of viral reprogamming factors", *Cell*, 136:964-977 (2009).
Spitzer, et al,, "Orchestrating neuronal differentiation: patterns of $Ca^{2+}$ spikes specify transmitter choice", *Trends in Neurosciences*, 27(7):415-421 (2004).
Splawski, et al., "CACNA1H Mutations in autism spectrum disorders", *The Journal of Biological Chemistry*, 281(31):22085-22091 (2006).
Takahashi, et al., "Induction of pluripotent stem cells from adult human fibroblasts by defined factors", *Cell*, 131:861-872 (2007).
Tao, et al., "Phosphorylation of MeCP2 at serine 80 regulates its chromatin association and neurological function", *PNAS*, 106(12):4882-4887 (2009).
Traynor, et al., "Gene expression patterns vary in clonal cell cultures from Rett syndrome females with eight different MECP2 mutations", *BMC Medical Genetics*, 3: 15 pages (2002).
Tropea, et al., "Partial reversal of Rett syndrome-like symptoms in MeCP2 mutant mice", *PNAS*, 106(6):2029-2034 (2009).
Tudor, et al., "Transcriptional profiling of a mouse model for Rett syndrome reveals subtle transcriptional changes in the brain", *PNAS*, 99(24):15536-15541 (2002).
Tudor, et al., "Transcriptional profiling of a mouse model for Rett syndrome reveals subtle transcriptional changes in the brain", *PNAS*, 99(24): Table 3 (2002).
Tudor, et al., "Transcriptional profiling of a mouse model for Rett syndrome reveals subtle transcriptional changes in the brain", *PNAS*, 99(24): Figure 3 (2002).
Tudor, et al., "Transcriptional profiling of a mouse model for Rett syndrome reveals subtle transcriptional changes in the brain", *PNAS*, 99(24): Table 4 (2002).
Tudor, et al., "Transcriptional profiling of a mouse model for Rett syndrome reveals subtle transcriptional changes in the brain", *PNAS*, 99(24): Figure 4 (2002).
Van Esch, et al., "Duplication of the MECP2 region is a frequent cause of severe mental retardation and progressive neurological symptoms in males", *Am. J. Hum. Genet.*, 77:442-453 (2005).
Van Esch, et al., "Duplication of the MECP2 region is a frequent cause of severe mental retardation and progressive neurological symptoms in males", *Am. J. Hum. Genet.*, 77:442-453 (2005) (Supplemental Data).
Yamanka, "A fresh look at iPS Cells", *Cell*, 137:13-17 (2009).

(56) References Cited

OTHER PUBLICATIONS

Yasui, et al., :Integrated epigenomic analyses of neuronal MeCP2 reveal a role for long-range interaction with active genes, *PNAS*, 104(49):19416-19421 (2007).
Yeo, et al., :Alternative splicing events identified in human embryonic stem cells and neural progenitors, *PLoS*, 3(10):e196 (pp. 1951-1967) (2007).
Zapella, et al., "Study of MECP2 gene in Rett syndrome variants and autistic girls", *American Journal of Medical Genetics Part B (Neuropsychiatric Genetics)*, 119B:102-107 (2003).
Zhou, et al., "Brain-specific phosphorylation of MeCP2 regulates activity-dependent Bdnftranscription, dendritic growth, and spine maturation", *Neuron*, 52:255-269 (2006).
Zoghbi, "Postnatal neurodevelopmental disorders: Meeting at the synapse?", *Science*, 302:826-830 (2003).

\* cited by examiner

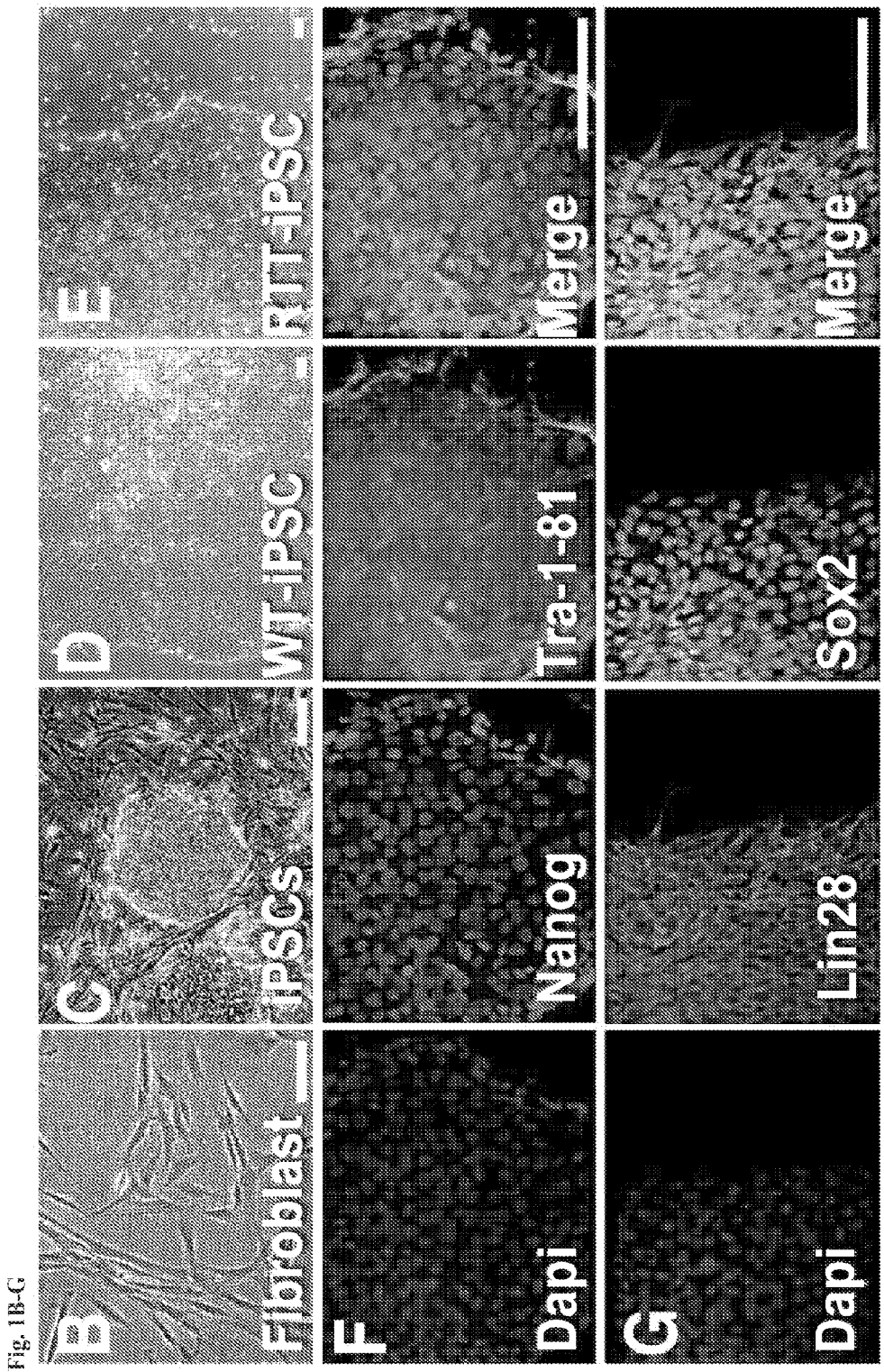
Fig. 1B-G

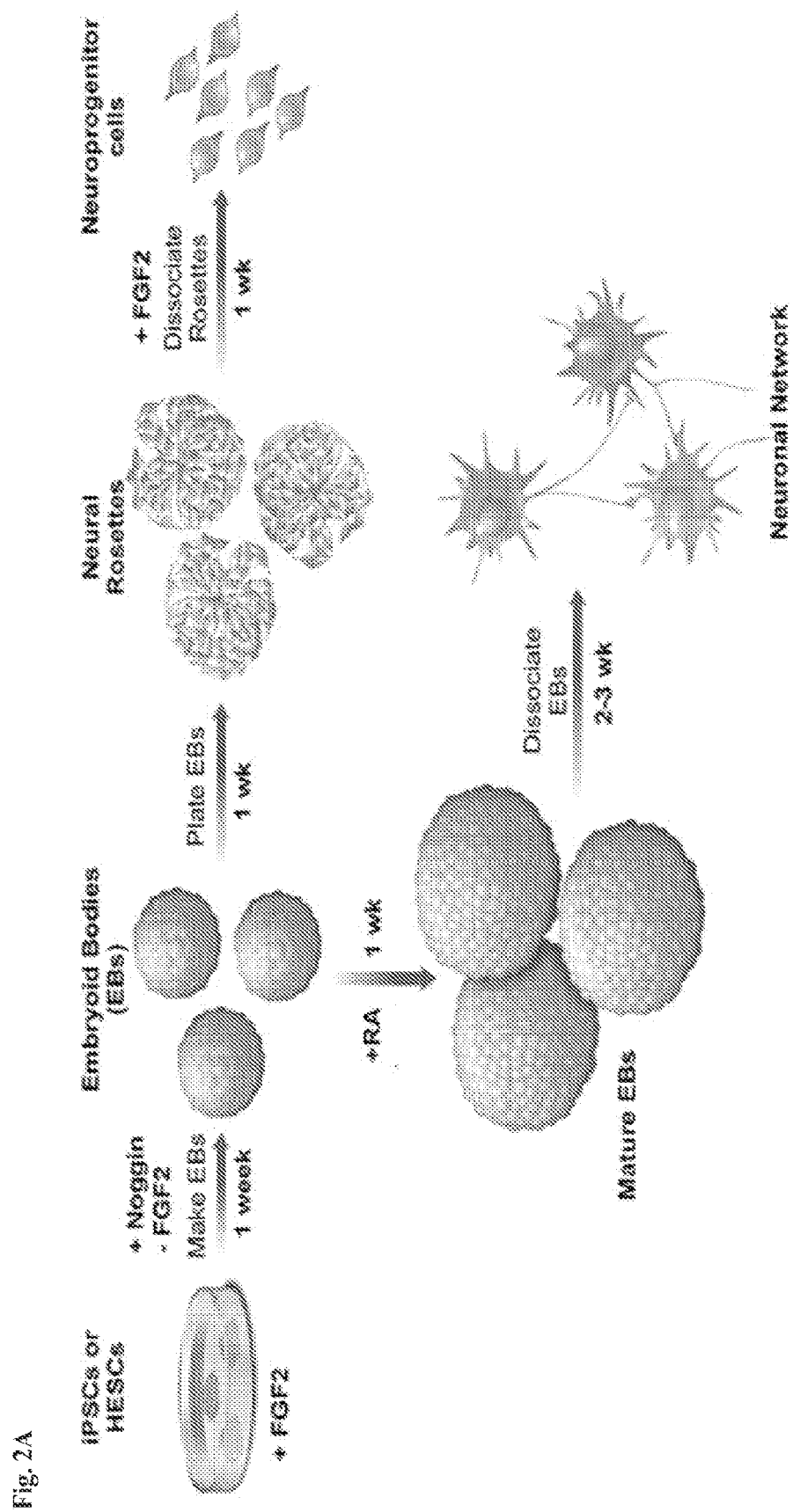

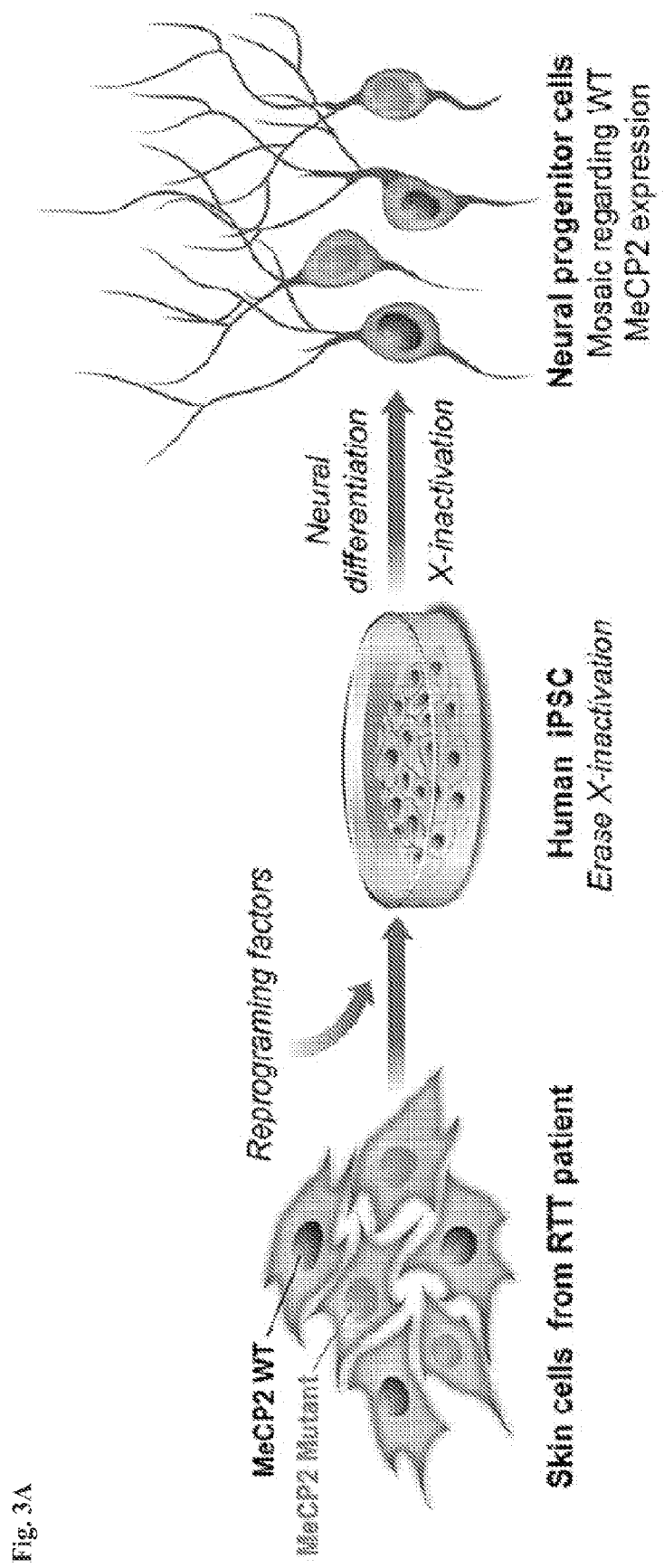

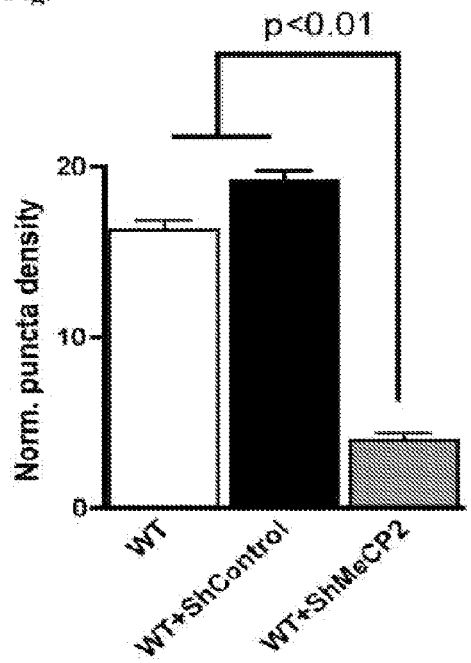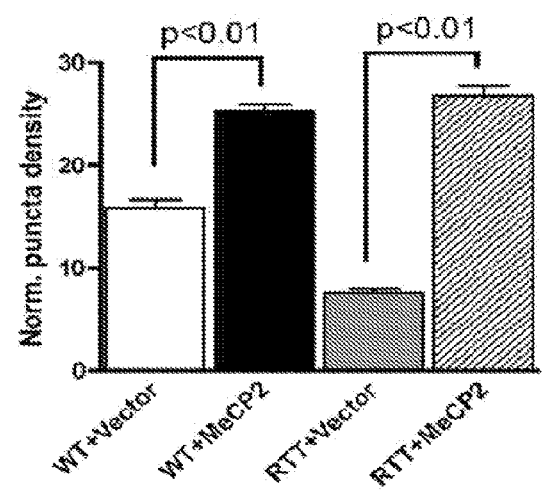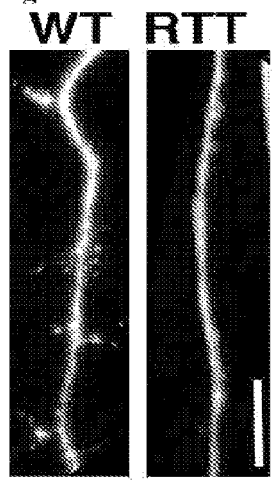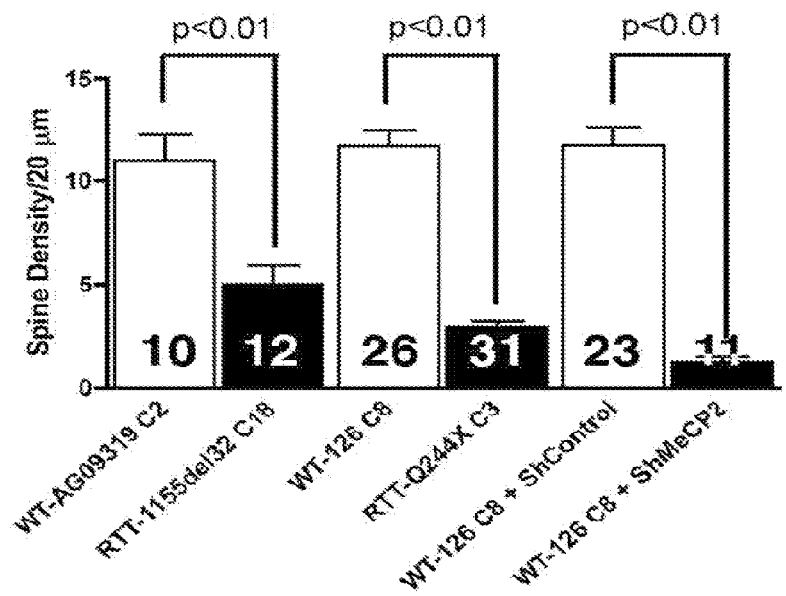

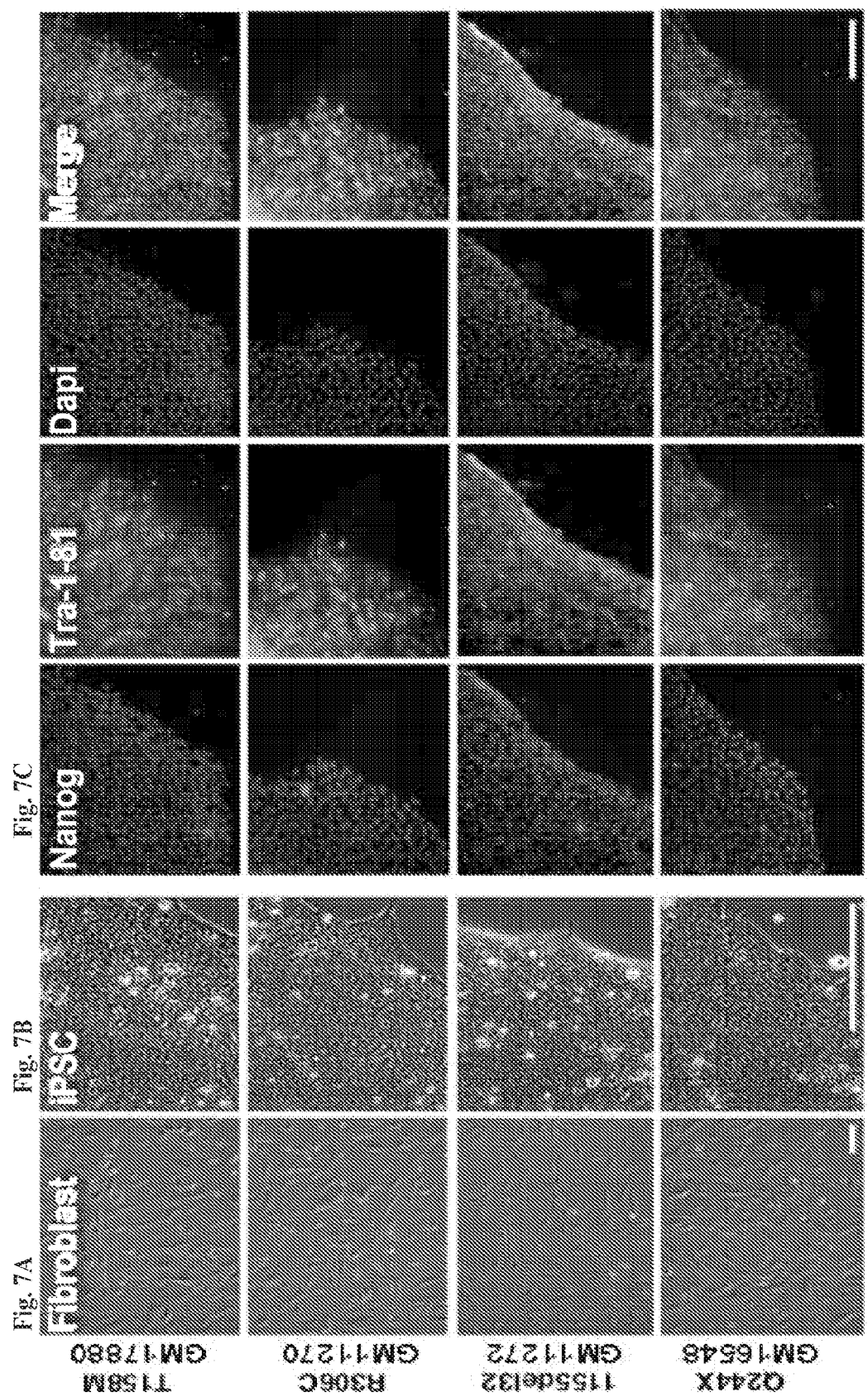

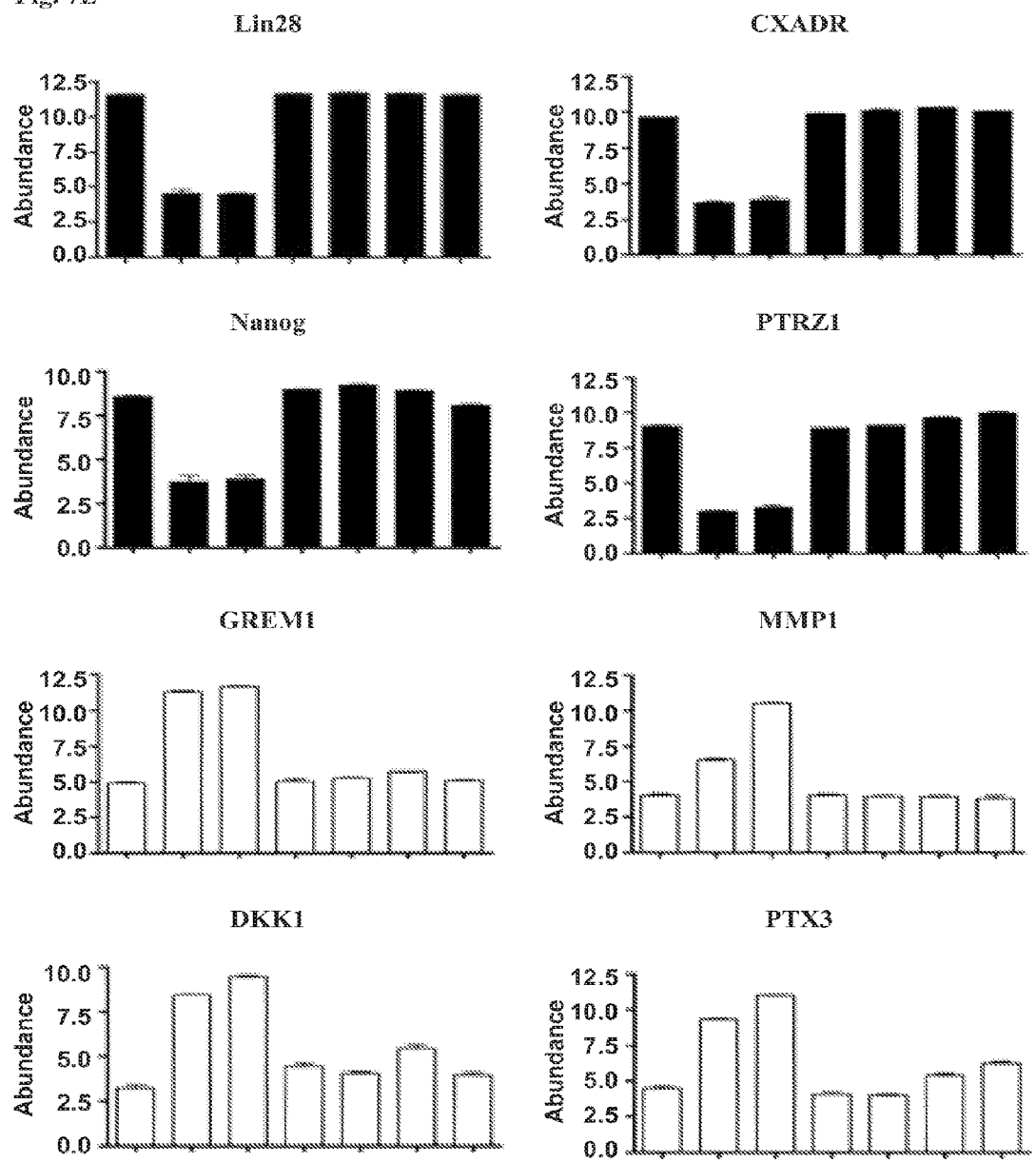

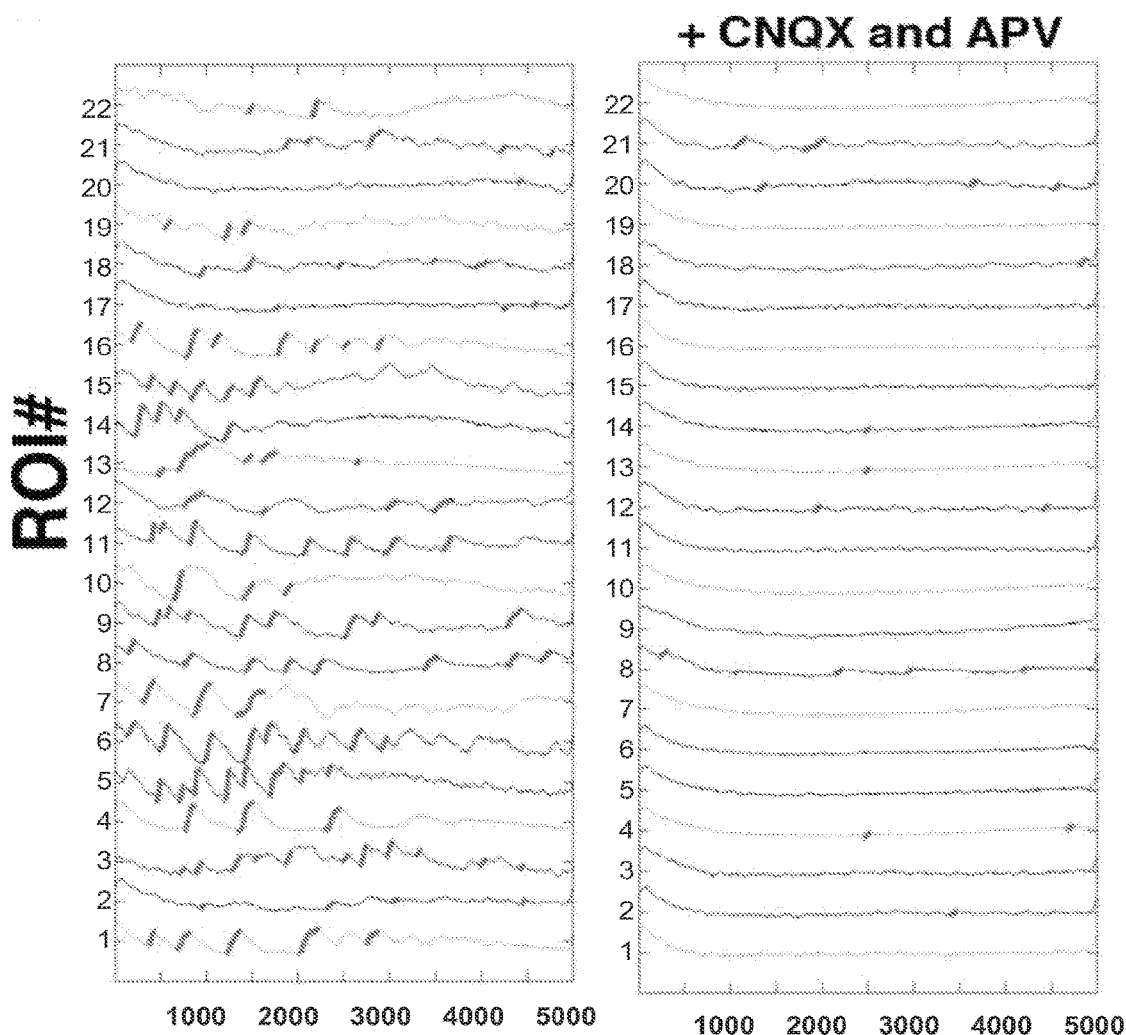

SEQUENCE LISTING

```
<160> NUMBER OF SEQ ID NOS: 20

<210> SEQ ID NO 1
<211> LENGTH: 479
<212> TYPE: PRT
<213> ORGANISM: Homo sapiens

<400> SEQUENCE: 1

Met Arg Gln Pro Pro Gly Glu Ser Asp Met Ala Val Ser Asp Ala Leu
1               5                   10                  15

Leu Pro Ser Phe Ser Thr Phe Ala Ser Gly Pro Ala Gly Arg Glu Lys
            20                  25                  30

Thr Leu Arg Gln Ala Gly Ala Pro Asn Asn Arg Trp Arg Glu Glu Leu
        35                  40                  45

Ser His Met Lys Arg Leu Pro Pro Val Leu Pro Gly Arg Pro Tyr Asp
    50                  55                  60

Leu Ala Ala Ala Thr Val Ala Thr Asp Leu Glu Ser Gly Gly Ala Gly
65                  70                  75                  80

Ala Ala Cys Gly Gly Ser Asn Leu Ala Pro Leu Pro Arg Arg Glu Thr
                85                  90                  95

Glu Glu Phe Asn Asp Leu Leu Asp Leu Asp Phe Ile Leu Ser Asn Ser
            100                 105                 110

Leu Thr His Pro Pro Glu Ser Val Ala Ala Thr Val Ser Ser Ser Ala
        115                 120                 125

Ser Ala Ser Ser Ser Ser Ser Pro Ser Ser Ser Gly Pro Ala Ser Ala
    130                 135                 140

Pro Ser Thr Cys Ser Phe Thr Tyr Pro Ile Arg Ala Gly Asn Asp Pro
145                 150                 155                 160

Gly Val Ala Pro Gly Gly Thr Gly Gly Gly Leu Leu Tyr Gly Arg Glu
                165                 170                 175

Ser Ala Pro Pro Pro Thr Ala Pro Phe Asn Leu Ala Asp Ile Asn Asp
            180                 185                 190

Val Ser Pro Ser Gly Gly Phe Val Ala Glu Leu Leu Arg Pro Glu Leu
        195                 200                 205

Asp Pro Val Tyr Ile Pro Pro Gln Gln Pro Gln Pro Pro Gly Gly Gly
    210                 215                 220

Leu Met Gly Lys Phe Val Leu Lys Ala Ser Leu Ser Ala Pro Gly Ser
225                 230                 235                 240

Glu Tyr Gly Ser Pro Ser Val Ile Ser Val Ser Lys Gly Ser Pro Asp
```

```
                245                 250                 255
Gly Ser His Pro Val Val Ala Pro Tyr Asn Gly Pro Pro Arg
        260                 265                 270

Thr Cys Pro Lys Ile Lys Gln Glu Ala Val Ser Ser Cys Thr His Leu
        275                 280                 285

Gly Ala Gly Pro Pro Leu Ser Asn Gly His Arg Pro Ala Ala His Asp
        290                 295                 300

Phe Pro Leu Gly Arg Gln Leu Pro Ser Arg Thr Thr Pro Thr Leu Gly
305                 310                 315                 320

Leu Glu Glu Val Leu Ser Ser Arg Asp Cys His Pro Ala Leu Pro Leu
                325                 330                 335

Pro Pro Gly Phe His Pro His Pro Gly Pro Asn Tyr Pro Ser Phe Leu
                340                 345                 350

Pro Asp Gln Met Gln Pro Gln Val Pro Pro Leu His Tyr Gln Glu Leu
                355                 360                 365

Met Pro Pro Gly Ser Cys Met Pro Glu Glu Pro Lys Pro Lys Arg Gly
        370                 375                 380

Arg Arg Ser Trp Pro Arg Lys Arg Thr Ala Thr His Thr Cys Asp Tyr
385                 390                 395                 400

Ala Gly Cys Gly Lys Thr Tyr Thr Lys Ser Ser His Leu Lys Ala His
                405                 410                 415

Leu Arg Thr His Thr Gly Glu Lys Pro Tyr His Cys Asp Trp Asp Gly
                420                 425                 430

Cys Gly Trp Lys Phe Ala Arg Ser Asp Glu Leu Thr Arg His Tyr Arg
        435                 440                 445

Lys His Thr Gly His Arg Pro Phe Gln Cys Gln Lys Cys Asp Arg Ala
        450                 455                 460

Phe Ser Arg Ser Asp His Leu Ala Leu His Met Lys Arg His Phe
465                 470                 475

<210> SEQ ID NO 2
<211> LENGTH: 360
<212> TYPE: PRT
<213> ORGANISM: Homo sapiens

<400> SEQUENCE: 2

Met Ala Gly His Leu Ala Ser Asp Phe Ala Phe Ser Pro Pro Pro Gly
1               5                   10                  15

Gly Gly Gly Asp Gly Pro Gly Gly Pro Glu Pro Gly Trp Val Asp Pro
                20                  25                  30

Arg Thr Trp Leu Ser Phe Gln Gly Pro Pro Gly Gly Pro Gly Ile Gly
            35                  40                  45

Pro Gly Val Gly Pro Gly Ser Glu Val Trp Gly Ile Pro Pro Cys Pro
        50                  55                  60

Pro Pro Tyr Glu Phe Cys Gly Gly Met Ala Tyr Cys Gly Pro Gln Val
65                  70                  75                  80

Gly Val Gly Leu Val Pro Gln Gly Gly Leu Glu Thr Ser Gln Pro Glu
                85                  90                  95

Gly Glu Ala Gly Val Gly Val Glu Ser Asn Ser Asp Gly Ala Ser Pro
            100                 105                 110

Glu Pro Cys Thr Val Thr Pro Gly Ala Val Lys Leu Glu Lys Glu Lys
        115                 120                 125

Leu Glu Gln Asn Pro Glu Glu Ser Gln Asp Ile Lys Ala Leu Gln Lys
    130                 135                 140
```

```
Glu Leu Glu Gln Phe Ala Lys Leu Leu Lys Gln Lys Arg Ile Thr Leu
145                 150                 155                 160

Gly Tyr Thr Gln Ala Asp Val Gly Leu Thr Leu Gly Val Leu Phe Gly
                165                 170                 175

Lys Val Phe Ser Gln Thr Thr Ile Cys Arg Phe Glu Ala Leu Gln Leu
            180                 185                 190

Ser Phe Lys Asn Met Cys Lys Leu Arg Pro Leu Leu Gln Lys Trp Val
        195                 200                 205

Glu Glu Ala Asp Asn Asn Glu Asn Leu Gln Glu Ile Cys Lys Ala Glu
    210                 215                 220

Thr Leu Val Gln Ala Arg Lys Arg Lys Arg Thr Ser Ile Glu Asn Arg
225                 230                 235                 240

Val Arg Gly Asn Leu Glu Asn Leu Phe Leu Gln Cys Pro Lys Pro Thr
                245                 250                 255

Leu Gln Gln Ile Ser His Ile Ala Gln Gln Leu Gly Leu Glu Lys Asp
                260                 265                 270

Val Val Arg Val Trp Phe Cys Asn Arg Arg Gln Lys Gly Lys Arg Ser
            275                 280                 285

Ser Ser Asp Tyr Ala Gln Arg Glu Asp Phe Glu Ala Ala Gly Ser Pro
    290                 295                 300

Phe Ser Gly Gly Pro Val Ser Phe Pro Leu Ala Pro Gly Pro His Phe
305                 310                 315                 320

Gly Thr Pro Gly Tyr Gly Ser Pro His Phe Thr Ala Leu Tyr Ser Ser
                325                 330                 335

Val Pro Phe Pro Glu Gly Glu Ala Phe Pro Pro Val Ser Val Thr Thr
            340                 345                 350

Leu Gly Ser Pro Met His Ser Asn
        355                 360

<210> SEQ ID NO 3
<211> LENGTH: 265
<212> TYPE: PRT
<213> ORGANISM: Homo sapiens

<400> SEQUENCE: 3

Met His Phe Tyr Arg Leu Phe Leu Gly Ala Thr Arg Arg Phe Leu Asn
1               5                   10                  15

Pro Glu Trp Lys Gly Glu Ile Asp Asn Trp Cys Val Tyr Val Leu Thr
            20                  25                  30

Ser Leu Leu Pro Phe Lys Ile Gln Ser Gln Asp Ile Lys Ala Leu Gln
        35                  40                  45

Lys Glu Leu Glu Gln Phe Ala Lys Leu Leu Lys Gln Lys Arg Ile Thr
    50                  55                  60

Leu Gly Tyr Thr Gln Ala Asp Val Gly Leu Thr Leu Gly Val Leu Phe
65                  70                  75                  80

Gly Lys Val Phe Ser Gln Thr Thr Ile Cys Arg Phe Glu Ala Leu Gln
                85                  90                  95

Leu Ser Phe Lys Asn Met Cys Lys Leu Arg Pro Leu Leu Gln Lys Trp
            100                 105                 110

Val Glu Glu Ala Asp Asn Asn Glu Asn Leu Gln Glu Ile Cys Lys Ala
        115                 120                 125

Glu Thr Leu Val Gln Ala Arg Lys Arg Lys Arg Thr Ser Ile Glu Asn
    130                 135                 140

Arg Val Arg Gly Asn Leu Glu Asn Leu Phe Leu Gln Cys Pro Lys Pro
145                 150                 155                 160
```

```
Thr Leu Gln Gln Ile Ser His Ile Ala Gln Gln Leu Gly Leu Glu Lys
            165                 170                 175

Asp Val Val Arg Val Trp Phe Cys Asn Arg Arg Gln Lys Gly Lys Arg
        180                 185                 190

Ser Ser Ser Asp Tyr Ala Gln Arg Glu Asp Phe Glu Ala Ala Gly Ser
    195                 200                 205

Pro Phe Ser Gly Gly Pro Val Ser Phe Pro Leu Ala Pro Gly Pro His
210                 215                 220

Phe Gly Thr Pro Gly Tyr Gly Ser Pro His Phe Thr Ala Leu Tyr Ser
225                 230                 235                 240

Ser Val Pro Phe Pro Glu Gly Glu Ala Phe Pro Pro Val Ser Val Thr
                245                 250                 255

Thr Leu Gly Ser Pro Met His Ser Asn
            260                 265

<210> SEQ ID NO 4
<211> LENGTH: 190
<212> TYPE: PRT
<213> ORGANISM: Homo sapiens

<400> SEQUENCE: 4

Met Gly Val Leu Phe Gly Lys Val Phe Ser Gln Thr Thr Ile Cys Arg
1               5                   10                  15

Phe Glu Ala Leu Gln Leu Ser Phe Lys Asn Met Cys Lys Leu Arg Pro
            20                  25                  30

Leu Leu Gln Lys Trp Val Glu Glu Ala Asp Asn Asn Glu Asn Leu Gln
        35                  40                  45

Glu Ile Cys Lys Ala Glu Thr Leu Val Gln Ala Arg Lys Arg Lys Arg
    50                  55                  60

Thr Ser Ile Glu Asn Arg Val Arg Gly Asn Leu Glu Asn Leu Phe Leu
65                  70                  75                  80

Gln Cys Pro Lys Pro Thr Leu Gln Gln Ile Ser His Ile Ala Gln Gln
                85                  90                  95

Leu Gly Leu Glu Lys Asp Val Val Arg Val Trp Phe Cys Asn Arg Arg
            100                 105                 110

Gln Lys Gly Lys Arg Ser Ser Ser Asp Tyr Ala Gln Arg Glu Asp Phe
        115                 120                 125

Glu Ala Ala Gly Ser Pro Phe Ser Gly Gly Pro Val Ser Phe Pro Leu
    130                 135                 140

Ala Pro Gly Pro His Phe Gly Thr Pro Gly Tyr Gly Ser Pro His Phe
145                 150                 155                 160

Thr Ala Leu Tyr Ser Ser Val Pro Phe Pro Glu Gly Glu Ala Phe Pro
                165                 170                 175

Pro Val Ser Val Thr Thr Leu Gly Ser Pro Met His Ser Asn
            180                 185                 190

<210> SEQ ID NO 5
<211> LENGTH: 317
<212> TYPE: PRT
<213> ORGANISM: Homo sapiens

<400> SEQUENCE: 5

Met Tyr Asn Met Met Glu Thr Glu Leu Lys Pro Pro Gly Pro Gln Gln
1               5                   10                  15

Thr Ser Gly Gly Gly Gly Gly Asn Ser Thr Ala Ala Ala Ala Gly Gly
            20                  25                  30
```

```
Asn Gln Lys Asn Ser Pro Asp Arg Val Lys Arg Pro Met Asn Ala Phe
         35                  40                  45

Met Val Trp Ser Arg Gly Gln Arg Arg Lys Met Ala Gln Glu Asn Pro
 50                  55                  60

Lys Met His Asn Ser Glu Ile Ser Lys Arg Leu Gly Ala Glu Trp Lys
 65                  70                  75                  80

Leu Leu Ser Glu Thr Glu Lys Arg Pro Phe Ile Asp Glu Ala Lys Arg
                 85                  90                  95

Leu Arg Ala Leu His Met Lys Glu His Pro Asp Tyr Lys Tyr Arg Pro
                100                 105                 110

Arg Arg Lys Thr Lys Thr Leu Met Lys Lys Asp Lys Tyr Thr Leu Pro
                115                 120                 125

Gly Gly Leu Leu Ala Pro Gly Gly Asn Ser Met Ala Ser Gly Val Gly
        130                 135                 140

Val Gly Ala Gly Leu Gly Ala Gly Val Asn Gln Arg Met Asp Ser Tyr
145                 150                 155                 160

Ala His Met Asn Gly Trp Ser Asn Gly Ser Tyr Ser Met Met Gln Asp
                165                 170                 175

Gln Leu Gly Tyr Pro Gln His Pro Gly Leu Asn Ala His Gly Ala Ala
                180                 185                 190

Gln Met Gln Pro Met His Arg Tyr Asp Val Ser Ala Leu Gln Tyr Asn
                195                 200                 205

Ser Met Thr Ser Ser Gln Thr Tyr Met Asn Gly Ser Pro Thr Tyr Ser
        210                 215                 220

Met Ser Tyr Ser Gln Gln Gly Thr Pro Gly Met Ala Leu Gly Ser Met
225                 230                 235                 240

Gly Ser Val Val Lys Ser Glu Ala Ser Ser Ser Pro Pro Val Val Thr
                245                 250                 255

Ser Ser Ser His Ser Arg Ala Pro Cys Gln Ala Gly Asp Leu Arg Asp
        260                 265                 270

Met Ile Ser Met Tyr Leu Pro Gly Ala Glu Val Pro Glu Pro Ala Ala
        275                 280                 285

Pro Ser Arg Leu His Met Ser Gln His Tyr Gln Ser Gly Pro Val Pro
        290                 295                 300

Gly Thr Ala Ile Asn Gly Thr Leu Pro Leu Ser His Met
305                 310                 315

<210> SEQ ID NO 6
<211> LENGTH: 454
<212> TYPE: PRT
<213> ORGANISM: Homo sapiens

<400> SEQUENCE: 6

Met Asp Phe Phe Arg Val Val Glu Asn Gln Gln Pro Pro Ala Thr Met
 1               5                  10                  15

Pro Leu Asn Val Ser Phe Thr Asn Arg Asn Tyr Asp Leu Asp Tyr Asp
                 20                  25                  30

Ser Val Gln Pro Tyr Phe Tyr Cys Asp Glu Glu Glu Asn Phe Tyr Gln
         35                  40                  45

Gln Gln Gln Gln Ser Glu Leu Gln Pro Pro Ala Pro Ser Glu Asp Ile
         50                  55                  60

Trp Lys Lys Phe Glu Leu Leu Pro Thr Pro Pro Leu Ser Pro Ser Arg
 65                  70                  75                  80

Arg Ser Gly Leu Cys Ser Pro Ser Tyr Val Ala Val Thr Pro Phe Ser
```

85                  90                  95
Leu Arg Gly Asp Asn Asp Gly Gly Gly Ser Phe Ser Thr Ala Asp
                    100                 105                 110

Gln Leu Glu Met Val Thr Glu Leu Leu Gly Gly Asp Met Val Asn Gln
            115                 120                 125

Ser Phe Ile Cys Asp Pro Asp Glu Thr Phe Ile Lys Asn Ile Ile
        130                 135                 140

Ile Gln Asp Cys Met Trp Ser Gly Phe Ser Ala Ala Lys Leu Val
145                 150                 155                 160

Ser Glu Lys Leu Ala Ser Tyr Gln Ala Ala Arg Lys Asp Ser Gly Ser
                165                 170                 175

Pro Asn Pro Ala Arg Gly His Ser Val Cys Ser Thr Ser Ser Leu Tyr
            180                 185                 190

Leu Gln Asp Leu Ser Ala Ala Ser Glu Cys Ile Asp Pro Ser Val
        195                 200                 205

Val Phe Pro Tyr Pro Leu Asn Asp Ser Ser Ser Pro Lys Ser Cys Ala
                210                 215                 220

Ser Gln Asp Ser Ser Ala Phe Ser Pro Ser Ser Asp Ser Leu Leu Ser
225                 230                 235                 240

Ser Thr Glu Ser Ser Pro Gln Gly Ser Pro Glu Pro Leu Val Leu His
                245                 250                 255

Glu Glu Thr Pro Pro Thr Thr Ser Ser Asp Ser Glu Glu Gln Glu
            260                 265                 270

Asp Glu Glu Glu Ile Asp Val Val Ser Val Glu Lys Arg Gln Ala Pro
                275                 280                 285

Gly Lys Arg Ser Glu Ser Gly Ser Pro Ser Ala Gly Gly His Ser Lys
            290                 295                 300

Pro Pro His Ser Pro Leu Val Leu Lys Arg Cys His Val Ser Thr His
305                 310                 315                 320

Gln His Asn Tyr Ala Ala Pro Pro Ser Thr Arg Lys Asp Tyr Pro Ala
                325                 330                 335

Ala Lys Arg Val Lys Leu Asp Ser Val Arg Val Leu Arg Gln Ile Ser
            340                 345                 350

Asn Asn Arg Lys Cys Thr Ser Pro Arg Ser Ser Asp Thr Glu Glu Asn
            355                 360                 365

Val Lys Arg Arg Thr His Asn Val Leu Glu Arg Gln Arg Arg Asn Glu
        370                 375                 380

Leu Lys Arg Ser Phe Phe Ala Leu Arg Asp Gln Ile Pro Glu Leu Glu
385                 390                 395                 400

Asn Asn Glu Lys Ala Pro Lys Val Val Ile Leu Lys Lys Ala Thr Ala
            405                 410                 415

Tyr Ile Leu Ser Val Gln Ala Glu Glu Gln Lys Leu Ile Ser Glu Glu
        420                 425                 430

Asp Leu Leu Arg Lys Arg Arg Glu Gln Leu Lys His Lys Leu Glu Gln
        435                 440                 445

Leu Arg Asn Ser Cys Ala
        450

<210> SEQ ID NO 7
<211> LENGTH: 10241
<212> TYPE: DNA
<213> ORGANISM: Artificial
<220> FEATURE:
<223> OTHER INFORMATION: Synthetic DNA which is cDNA of mRNA for Homo
      sapiens methyl CpG binding protein 2, transcript variant 1

<400> SEQUENCE: 7

```
ccggcgtcgg cggcgcgcgc gctccctcct ctcggagaga gggctgtggt aaaagccgtc    60
cggaaaatgg ccgccgccgc cgccgccgcg ccgagcggag gaggaggagg aggcgaggag   120
gagagactgc tccataaaaa tacagactca ccagttcctg ctttgatgtg acatgtgact   180
ccccagaata caccttgctt ctgtagacca gctccaacag gattccatgg tagctgggat   240
gttagggctc agggaagaaa agtcagaaga ccaggacctc cagggcctca aggacaaacc   300
cctcaagttt aaaaaggtga agaaagataa gaaagaagag aaagagggca agcatgagcc   360
cgtgcagcca tcagcccacc actctgctga gcccgcagag gcaggcaaag cagagacatc   420
agaagggtca ggctccgccc cggctgtgcc ggaagcttct gcctccccca acagcggcg   480
ctccatcatc cgtgaccggg gacccatgta tgatgacccc accctgcctg aaggctggac   540
acggaagctt aagcaaagga atctggccg ctctgctggg aagtatgatg tgtatttgat   600
caatccccag ggaaaagcct ttcgctctaa agtggagttg attgcgtact tcgaaaaggt   660
aggcgacaca tccctggacc ctaatgattt tgacttcacg gtaactggga gagggagccc   720
ctcccggcga gagcagaaac cacctaagaa gcccaaatct cccaaagctc caggaactgg   780
cagaggccgg ggacgcccca agggagcgg caccacgaga cccaaggcgg ccacgtcaga   840
gggtgtgcag gtgaaaaggg tcctggagaa aagtcctggg aagctccttg tcaagatgcc   900
ttttcaaact tcgccagggg gcaaggctga ggggggtggg gccaccacat ccacccaggt   960
catggtgatc aaacgccccg gcaggaagcg aaaagctgag gccgaccctc aggccattcc  1020
caagaaacgg ggccgaaagc cggggagtgt ggtggcagcc gctgccgccg aggccaaaaa  1080
gaaagccgtg aaggagtctt ctatccgatc tgtgcaggag accgtactcc ccatcaagaa  1140
gcgcaagacc cgggagacgg tcagcatcga ggtcaaggaa gtggtgaagc ccctgctggt  1200
gtccaccctc ggtgagaaga gcgggaaagg actgaagacc tgtaagagcc ctgggcggaa  1260
aagcaaggag agcagcccca aggggcgcag cagcagcgcc tcctcacccc ccaagaagga  1320
gcaccaccac catcaccacc actcagagtc cccaaaggcc cccgtgccac tgctcccacc  1380
cctgccccca cctccacctg agcccgagag ctccgaggac cccaccagcc ccctgagcc  1440
ccaggacttg agcagcagcg tctgcaaaga ggagaagatg cccagaggag gctcactgga  1500
gagcgacggc tgccccaagg agccagctaa gactcagccc cgcggttgcca ccgccgccac  1560
ggccgcagaa aagtacaaac accgagggga gggagagcgc aaagacattg tttcatcctc  1620
catgccaagg ccaaacagag aggagcctgt ggacagccgg acgcccgtga ccgagagagt  1680
tagctgactt tacacggagc ggattgcaaa gcaaaccaac aagaataaag gcagctgttg  1740
tctcttctcc ttatgggtag ggctctgaca aagcttcccg attaactgaa ataaaaaata  1800
ttttttttc tttcagtaaa cttagagttt cgtggcttca gggtgggagt agttggagca  1860
ttggggatgt ttttcttacc gacaagcaca gtcaggttga agacctaacc agggccagaa  1920
gtagctttgc actttctaa actaggctcc ttcaacaagg cttgctgcag atactactga  1980
ccagacaagc tgttgaccag gcacctcccc tcccgcccaa accttccccc catgtggtcg  2040
ttagagacag agcgacagag cagttgagag gacactcccg ttttcggtgc catcagtgcc  2100
ccgtctacag ctccccccagc tcccccccacc tcccccactc ccaaccacgt tgggacaggg  2160
aggtgtgagg caggagagac agttggattc tttagagaag atggatatga ccagtggcta  2220
tggcctgtgc gatcccaccc gtggtggctc aagtctggcc ccacaccagc cccaatccaa  2280
```

```
aactggcaag gacgcttcac aggacaggaa agtggcacct gtctgctcca gctctggcat    2340
ggctaggagg ggggagtccc ttgaactact gggtgtagac tggcctgaac cacaggagag    2400
gatggcccag ggtgaggtgg catggtccat tctcaaggga cgtcctccaa cgggtggcgc    2460
tagaggccat ggaggcagta ggacaaggtg caggcaggct ggcctgggt caggccgggc     2520 agagcacagc ggggtgagag ggattcctaa tcactcagag cagtctgtga cttagtggac    2580
aggggagggg gcaaaggggg aggagaagaa aatgttcttc cagttacttt ccaattctcc    2640
tttagggaca gcttagaatt atttgcacta ttgagtcttc atgttcccac ttcaaaacaa    2700
acagatgctc tgagagcaaa ctggcttgaa ttggtgacat ttagtccctc aagccaccag    2760
atgtgacagt gttgagaact acctggattt gtatatatac ctgcgcttgt tttaaagtgg    2820
gctcagcaca tagggttccc acgaagctcc gaaactctaa gtgtttgctg caattttata    2880
aggacttcct gattggtttc tcttctcccc ttccatttct gccttttgtt catttcatcc    2940
tttcacttct ttcccttcct ccgtcctcct ccttcctagt tcatcccttc tcttccaggc    3000
agccgcggtg cccaaccaca cttgtcggct ccagtcccca gaactctgcc tgcccttttgt   3060 cctcctgctg ccagtaccag ccccaccctg ttttgagccc tgaggaggcc ttgggctctg    3120
ctgagtccga cctggcctgt ctgtgaagag caagagagca gcaaggtctt gctctcctag    3180
gtagccccct cttccctggt aagaaaaagc aaaaggcatt tcccaccctg aacaacgagc    3240
cttttcaccc ttctactcta gagaagtgga ctggaggagc tgggcccgat ttggtagttg    3300
aggaaagcac agaggcctcc tgtggcctgc cagtcatcga gtggcccaac aggggctcca    3360
tgccagccga ccttgacctc actcagaagt ccagagtcta gcgtagtgca gcagggcagt    3420
agcggtacca atgcagaact cccaagaccc gagctgggac cagtacctgg gtccccagcc    3480
cttcctctgc tccccttttt ccctcggagt tcttcttgaa tggcaatgtt ttgcttttgc    3540
tcgatgcaga caggggccca gaacaccaca catttcactg tctgtctggt ccatagctgt    3600
ggtgtagggg cttagaggca tgggcttgct gtgggttttt aattgatcag ttttcatgtg    3660
ggatcccatc ttttaaccct ctgttcagga agtccttatc tagctgcata tcttcatcat    3720
attggtatat cctttctgt gtttacagag atgtctctta tatctaaatc tgtccaactg     3780
agaagtacct tatcaaagta gcaaatgaga cagcagtctt atgcttccag aaacacccac    3840
aggcatgtcc catgtgagct gctgccatga actgtcaagt gtgtgttgtc ttgtgtatt    3900 cagttattgt ccctggcttc cttactatgg tgtaatcatg aaggagtgaa acatcataga    3960
aactgtctag cacttccttg ccagtcttta gtgatcagga accatagttg acagttccaa    4020
tcagtagctt aagaaaaaac cgtgtttgtc tcttctggaa tggttagaag tgagggagtt    4080
tgccccgttc tgtttgtaga gtctcatagt tggactttct agcatatatg tgtccatttc    4140
cttatgctgt aaaagcaagt cctgcaacca aactcccatc agcccaatcc ctgatccctg    4200
atcccttcca cctgctctgc tgatgacccc cccagcttca cttctgactc ttccccagga    4260
agggaagggg ggtcagaaga gagggtgagt cctccagaac tcttcctcca aggacagaag    4320
gctcctgccc ccatagtggc ctcgaactcc tggcactacc aaaggacact tatccacgag    4380
agcgcagcat ccgaccaggt tgtcactgag aagatgttta ttttggtcag ttgggttttt    4440
atgtattata cttagtcaaa tgtaatgtgg cttctggaat cattgtccag agctgcttcc    4500
ccgtcacctg ggcgtcatct ggtcctggta agaggagtgc gtggcccacc aggccccct    4560 gtcacccatg acagttcatt caggccgat ggggcagtcg tggttgggaa cacagcattt     4620
caagcgtcac tttatttcat tcgggcccca cctgcagctc cctcaaagag gcagttgccc    4680
```

```
agcctctttc ccttccagtt tattccagag ctgccagtgg ggcctgaggc tccttagggt    4740
tttctctcta tttcccccTt tcttcctcat ccctcgtct ttcccaaagg catcacgagt    4800
cagtcgcctt tcagcaggca gccttggcgg tttatcgccc tggcaggcag gggccctgca    4860
gctctcatgc tgcccctgcc ttggggtcag gttgacagga ggttggaggg aaagccttaa    4920
gctgcaggat tctcaccagc tgtgtccggc ccagttttgg ggtgtgacct caatttcaat    4980
tttgtctgta cttgaacatt atgaagatgg gggcctcttt cagtgaattt gtgaacagca    5040
gaattgaccg acagctttcc agtacccatg gggctaggtc attaaggcca catccacagt    5100
ctcccccacc cttgttccag ttgttagtta ctacctcctc tcctgacaat actgtatgtc    5160
gtcgagctcc ccccaggtct acccctcccg gccctgcctg ctggtgggct tgtcatagcc    5220
agtgggattg ccggtcttga cagctcagtg agctggagat acttggtcac agccaggcgc    5280
tagcacagct cccttctgtt gatgctgtat tcccatatca aaagacacag ggacaccca    5340 gaaacgccac atcccccaat ccatcagtgc caaactagcc aacggcccca gcttctcagc    5400
tcgctggatg gcggaagctg ctactcgtga gcgccagtgc gggtgcagac aatcttctgt    5460
tgggtggcat cattccaggc ccgaagcatg aacagtgcac ctgggacagg agcagcccc    5520 aaattgtcac ctgcttctct gcccagcttt tcattgctgt gacagtgatg gcgaaagagg    5580
gtaataacca gacacaaact gccaagttgg gtggagaaag gagtttcttt agctgacaga    5640
atctctgaat tttaaatcac ttagtaagcg gctcaagccc aggagggagc agagggatac    5700
gagcggagtc ccctgcgcgg gaccatctgg aattggttta gcccaagtgg agcctgacag    5760
ccagaactct gtgtcccccg tctaaccaca gctccttttc cagagcattc cagtcaggct    5820
ctctgggctg actgggccag gggaggttac aggtaccagt tctttaagaa gatctttggg    5880
catatacatt tttagcctgt gtcattgccc caaatggatt cctgtttcaa gttcacacct    5940
gcagattcta ggacctgtgt cctagacttc agggagtcag ctgtttctag agttcctacc    6000
atggagtggg tctggaggac ctgcccggtg ggggggcaga gccctgctcc ctccgggtct    6060
tcctactctt ctctctgctc tgacgggatt tgttgattct ctccattttg gtgtctttct    6120
cttttagata ttgtatcaat ctttagaaaa ggcatagtct acttgttata aatcgttagg    6180
atactgcctc ccccagggtc taaaattaca tattagaggg gaaaagctga acactgaagt    6240
cagttctcaa caatttagaa ggaaaaccta gaaaacattt ggcagaaaat tacatttcga    6300 tgttttgaa tgaatacgag caagctttta caacagtgct gatctaaaaa tacttagcac    6360
ttggcctgag atgcctggtg agcattacag gcaaggggaa tctggaggta gccgacctga    6420
ggacatggct tctgaacctg tcttttggga gtggtatgga aggtggagcg ttcaccagtg    6480
acctggaagg cccagcacca ccctccttcc cactcttctc atcttgacag agcctgcccc    6540
agcgctgacg tgtcaggaaa acacccaggg aactaggaag gcacttctgc ctgaggggca    6600
gcctgccttg cccactcctg ctctgctcgc ctcggatcag ctgagccttc tgagctggcc    6660
tctcactgcc tccccaaggc cccctgcctg cctgtcagg aggcagaagg aagcaggtgt    6720
gagggcagtg caaggaggga gcacaacccc cagctcccgc tccgggctcc gacttgtgca    6780
caggcagagc ccagaccctg gaggaaatcc tacctttgaa ttcaagaaca tttggggaat    6840
ttggaaatct cttttgcccc aaaccccat tctgtcctac cttttaatcag gtcctgctca    6900 gcagtgagag cagatgaggt gaaaaggcca agaggtttgg ctcctgccca ctgatagccc    6960 ctctcccgc agtgtttgtg tgtcaagtgg caaagctgtt cttcctggtg accctgatta    7020
```

-continued

```
tatccagtaa cacatagact gtgcgcatag gcctgctttg tctcctctat cctgggcttt      7080
tgttttgctt tttagttttg cttttagttt ttctgtccct tttatttaac gcaccgacta      7140
gacacacaaa gcagttgaat ttttatatat atatctgtat attgcacaat tataaactca      7200
ttttgcttgt ggctccacac acacaaaaaa agacctgtta aaattatacc tgttgcttaa      7260
ttacaatatt tctgataacc atagcatagg acaagggaaa ataaaaaaag aaaaaaaaga      7320
aaaaaaaacg acaaatctgt ctgctggtca cttcttctgt ccaagcagat tcgtggtctt      7380
ttcctcgctt cttctcaaggg ctttcctgtg ccaggtgaag gaggctccag gcagcaccca      7440
ggttttgcac tcttgtttct cccgtgcttg tgaaagaggt cccaaggttc tgggtgcagg      7500
agcgctccct tgacctgctg aagtccggaa cgtagtcggc acagcctggt cgccttccac      7560
ctctgggagc tggagtccac tggggtggcc tgactccccc agtcccttc ccgtgacctg      7620
gtcagggtga gcccatgtgg agtcagcctc gcaggcctcc ctgccagtag ggtccgagtg      7680
tgtttcatcc ttcccactct gtcgagcctg gggctggag cggagacggg aggcctggcc      7740
tgtctcggaa cctgtgagct gcaccaggta gaacgccagg acccccagaa tcatgtgcgt      7800
cagtccaagg ggtcccctcc aggagtagtg aagactccag aaatgtccct ttcttctccc      7860
ccatcctacg agtaattgca tttgcttttg taattcttaa tgagcaatat ctgctagaga      7920
gtttagctgt aacagttctt tttgatcatc ttttttaat aattagaaac accaaaaaaa      7980
tccagaaact tgttcttcca aagcagagag cattataatc accagggcca aaagcttccc      8040
tccctgctgt cattgcttct tctgaggcct gaatccaaaa gaaaacagc cataggccct      8100
ttcagtggcc gggctacccg tgagcccttc ggaggaccag ggctggggca gcctctgggc      8160
ccacatccgg ggccagctcc ggcgtgtgtt cagtgttagc agtgggtcat gatgctcttt      8220
cccacccagc ctgggatagg ggcagaggag gcgaggaggc cgttgccgct gatgtttggc      8280
cgtgaacagg tgggtgtctg cgtgcgtcca cgtgcgtgtt ttctgactga catgaaatcg      8340
acgcccgagt tagcctcacc cggtgacctc tagccctgcc cggatggagc ggggcccacc      8400
cggttcagtg tttctgggga ctggacagt ggagtgcaaa aggcttgcag aacttgaagc      8460
ctgctccttc ccttgctacc acggcctcct ttccgtttga tttgtcactg cttcaatcaa      8520
taacagccgc tccagagtca gtagtcaatg aatatatgac caaatatcac caggactgtt      8580
actcaatgtg tgccgagccc ttgcccatgc tgggctcccg tgtatctgga cactgtaacg      8640
tgtgctgtgt ttgctcccct tccccttcct tctttgccct ttacttgtct ttctggggtt      8700
tttctgtttg ggtttggttt ggttttatt tctccttttg tgttccaaac atgaggttct      8760
ctctactggt cctcttaact gtggtgttga ggcttatatt tgtgtaattt ttggtgggtg      8820
aaaggaattt tgctaagtaa atctcttctg tgtttgaact gaagtctgta ttgtaactat      8880
gtttaaagta attgttccag agacaaatat ttctagacac ttttttcttta caaacaaaag      8940
cattcggagg gagggggatg tgtgactgaga tgagagggga gagctgaaca gatgaccct      9000
gcccagatca gccagaagcc acccaaagca gtggagccca ggagtccac tccaagccag      9060
caagccgaat agctgatgtg ttgccacttt ccaagtcact gcaaaaccag gttttgttcc      9120
gcccagtgga ttcttgtttt gcttcccctc cccccgagat tattaccacc atcccgtgct      9180
tttaaggaaa ggcaagattg atgtttcctt gagggagcc aggagggat gtgtgtgtgc      9240
agagctgaag agctggggag aatggggctg ggcccaccca agcaggaggc tgggacgctc      9300
tgctgtgggc acaggtcagg ctaatgttgg cagatgcagc tcttcctgga caggccaggt      9360
ggtgggcatt ctctctccaa ggtgtgcccc gtgggcatta ctgtttaaga cacttccgtc      9420
```

-continued

```
acatcccacc ccatcctcca gggctcaaca ctgtgacatc tctattcccc accctcccct   9480
tcccagggca ataaaatgac catggagggg gcttgcactc tcttggctgt cacccgatcg   9540
ccagcaaaac ttagatgtga gaaaacccct tcccattcca tggcgaaaac atctccttag   9600
aaaagccatt accctcatta ggcatggttt tgggctccca aaacacctga cagcccctcc   9660
ctcctctgag aggcggagag tgctgactgt agtgaccatt gcatgccggg tgcagcatct   9720
ggaagagcta ggcagggtgt ctgccccctc ctgagttgaa gtcatgctcc cctgtgccag   9780
cccagaggcc gagagctatg gacagcattg ccagtaacac aggccaccct gtgcagaagg   9840
gagctggctc cagcctggaa acctgtctga ggttgggaga ggtgcacttg gggcacaggg   9900
agaggccggg acacacttag ctggagatgt ctctaaaagc cctgtatcgt attcaccttc   9960 agttttgtg ttttgggaca attactttag aaaataagta ggtcgtttta aaacaaaaa   10020 ttattgattg cttttttgta gtgttcagaa aaaaggttct ttgtgtatag ccaaatgact   10080
gaaagcactg atatatttaa aaacaaaagg caatttatta aggaaatttg taccatttca   10140
gtaaacctgt ctgaatgtac ctgtatacgt ttcaaaaaca ccccccccccc actgaatccc   10200 tgtaacctat ttattatata aagagtttgc cttataaatt t                       10241
```

<210> SEQ ID NO 8
<211> LENGTH: 486
<212> TYPE: PRT
<213> ORGANISM: Homo sapeins

<400> SEQUENCE: 8

```
Met Val Ala Gly Met Leu Gly Leu Arg Glu Glu Lys Ser Glu Asp Gln
1               5                   10                  15

Asp Leu Gln Gly Leu Lys Asp Lys Pro Leu Lys Phe Lys Lys Val Lys
            20                  25                  30

Lys Asp Lys Lys Glu Glu Lys Glu Gly Lys His Glu Pro Val Gln Pro
        35                  40                  45

Ser Ala His His Ser Ala Glu Pro Ala Glu Ala Gly Lys Ala Glu Thr
    50                  55                  60

Ser Glu Gly Ser Gly Ser Ala Pro Ala Val Pro Glu Ala Ser Ala Ser
65                  70                  75                  80

Pro Lys Gln Arg Arg Ser Ile Ile Arg Asp Arg Gly Pro Met Tyr Asp
                85                  90                  95

Asp Pro Thr Leu Pro Glu Gly Trp Thr Arg Lys Leu Lys Gln Arg Lys
            100                 105                 110

Ser Gly Arg Ser Ala Gly Lys Tyr Asp Val Tyr Leu Ile Asn Pro Gln
        115                 120                 125

Gly Lys Ala Phe Arg Ser Lys Val Glu Leu Ile Ala Tyr Phe Glu Lys
    130                 135                 140

Val Gly Asp Thr Ser Leu Asp Pro Asn Asp Phe Asp Phe Thr Val Thr
145                 150                 155                 160

Gly Arg Gly Ser Pro Ser Arg Arg Glu Gln Lys Pro Pro Lys Lys Pro
                165                 170                 175

Lys Ser Pro Lys Ala Pro Gly Thr Gly Arg Gly Arg Gly Arg Pro Lys
            180                 185                 190

Gly Ser Gly Thr Thr Arg Pro Lys Ala Ala Thr Ser Glu Gly Val Gln
        195                 200                 205

Val Lys Arg Val Leu Glu Lys Ser Pro Gly Lys Leu Leu Val Lys Met
    210                 215                 220
```

```
Pro Phe Gln Thr Ser Pro Gly Gly Lys Ala Glu Gly Gly Ala Thr
225                 230                 235                 240

Thr Ser Thr Gln Val Met Val Ile Lys Arg Pro Gly Arg Lys Arg Lys
            245                 250                 255

Ala Glu Ala Asp Pro Gln Ala Ile Pro Lys Lys Arg Gly Arg Lys Pro
                260                 265                 270

Gly Ser Val Val Ala Ala Ala Ala Glu Ala Lys Lys Lys Ala Val
            275                 280                 285

Lys Glu Ser Ser Ile Arg Ser Val Gln Glu Thr Val Leu Pro Ile Lys
        290                 295                 300

Lys Arg Lys Thr Arg Glu Thr Val Ser Ile Glu Val Lys Glu Val Val
305                 310                 315                 320

Lys Pro Leu Leu Val Ser Thr Leu Gly Glu Lys Ser Gly Lys Gly Leu
                325                 330                 335

Lys Thr Cys Lys Ser Pro Gly Arg Lys Ser Lys Glu Ser Ser Pro Lys
            340                 345                 350

Gly Arg Ser Ser Ala Ser Ser Pro Pro Lys Lys Glu His His His
        355                 360                 365

His His His His Ser Glu Ser Pro Lys Ala Pro Val Pro Leu Leu Pro
370                 375                 380

Pro Leu Pro Pro Pro Pro Glu Pro Glu Ser Ser Glu Asp Pro Thr
385                 390                 395                 400

Ser Pro Pro Glu Pro Gln Asp Leu Ser Ser Ser Val Cys Lys Glu Glu
                405                 410                 415

Lys Met Pro Arg Gly Gly Ser Leu Glu Ser Asp Gly Cys Pro Lys Glu
                420                 425                 430

Pro Ala Lys Thr Gln Pro Ala Val Ala Thr Ala Ala Thr Ala Ala Glu
            435                 440                 445

Lys Tyr Lys His Arg Gly Glu Gly Glu Arg Lys Asp Ile Val Ser Ser
        450                 455                 460

Ser Met Pro Arg Pro Asn Arg Glu Glu Pro Val Asp Ser Arg Thr Pro
465                 470                 475                 480

Val Thr Glu Arg Val Ser
            485

<210> SEQ ID NO 9
<211> LENGTH: 1734
<212> TYPE: DNA
<213> ORGANISM: Artificial
<220> FEATURE:
<223> OTHER INFORMATION: Synthetic DNA which is cDNA of Homo sapiens
      methyl CpG binding protein 2, transcript variant 2

<400> SEQUENCE: 9
ccggcgtcgg cggcgcgcgc gctccctcct ctcggagaga gggctgtggt aaaagccgtc      60
cggaaaatgg ccgccgccgc cgccgccgcg ccgagcggag gaggaggagg aggcgaggag     120
gagagactgg aagaaaagtc agaagaccag gacctccagg gcctcaagga caaacccctc     180
aagtttaaaa aggtgaagaa agataagaaa gaagagaaag agggcaagca tgagcccgtg     240
cagccatcag cccaccactc tgctgagccc gcagaggcag gcaaagcaga gacatcagaa     300
gggtcaggct ccgccccggc tgtgccggaa gcttctgcct cccccaaaca gcggcgctcc     360
atcatccgtg accggggacc catgtatgat gaccccaccc tgcctgaagg ctggacacgg     420
aagcttaagc aaaggaaatc tggccgctct gctgggaagt atgatgtgta tttgatcaat     480
cccccaggga aaagcctttc gctctaaagtg gagttgattg cgtacttcga aaggtaggc      540
```

```
gacacatccc tggaccctaa tgattttgac ttcacggtaa ctgggagagg gagcccctcc      600
cggcgagagc agaaaccacc taagaagccc aaatctccca agctccagg aactggcaga      660 ggccggggac gccccaaagg gagcggcacc acgagaccca aggcggccac gtcagagggt      720
gtgcaggtga aaagggtcct ggagaaaagt cctgggaagc tccttgtcaa gatgcctttt      780
caaacttcgc caggggggcaa ggctgagggg ggtggggcca ccacatccac ccaggtcatg      840
gtgatcaaac gccccggcag gaagcgaaaa gctgaggccg accctcaggc cattcccaag      900
aaacggggcc gaaagccggg gagtgtggtg gcagccgctg ccgccgaggc caaaaagaaa      960
gccgtgaagg agtcttctat ccgatctgtg caggagaccg tactccccat caagaagcgc     1020
aagacccggg agacggtcag catcgaggtc aaggaagtgg tgaagcccct gctggtgtcc     1080
accctcggtg agaagagcgg gaaaggactg aagacctgta agagccctgg gcggaaaagc     1140
aaggagagca gccccaaggg gcgcagcagc agcgcctcct cacccccaa gaaggagcac     1200 caccaccatc accaccactc agagtcccca aaggcccccg tgccactgct cccacccctg     1260
cccccacctc cacctgagcc cgagagctcc gaggacccca ccagcccccc tgagcccag     1320 gacttgagca gcagcgtctg caaagaggag aagatgccca ggggaggctc actggagagc     1380
gacggctgcc ccaaggagcc agctaagact cagcccgcgg ttgccaccgc cgccacggcc     1440
gcagaaaagt acaaacaccg aggggaggga gagcgcaaag acattgtttc atcctccatg     1500
ccaaggccaa acagagagga gcctgtggac agccggacgc ccgtgaccga gagagttagc     1560
tgactttaca cggagcggat tgcaaagcaa accaacaaga ataaaggcag ctgttgtctc     1620
ttctccttat gggtagggct ctgacaaagc ttcccgatta actgaaataa aaatatttt     1680 tttttctttc agtaaaaaaa aaaaaaaaa aaaaaaaaa aaaaaaaaa aaaa              1734
```

<210> SEQ ID NO 10
<211> LENGTH: 498
<212> TYPE: PRT
<213> ORGANISM: Homo sapiens

<400> SEQUENCE: 10

```
Met Ala Ala Ala Ala Ala Ala Pro Ser Gly Gly Gly Gly Gly Gly
1               5                   10                  15

Glu Glu Glu Arg Leu Glu Glu Lys Ser Glu Asp Gln Asp Leu Gln Gly
            20                  25                  30

Leu Lys Asp Lys Pro Leu Lys Phe Lys Lys Val Lys Lys Asp Lys Lys
        35                  40                  45

Glu Glu Lys Glu Gly Lys His Glu Pro Val Gln Pro Ser Ala His His
    50                  55                  60

Ser Ala Glu Pro Ala Glu Ala Gly Lys Ala Glu Thr Ser Glu Gly Ser
65                  70                  75                  80

Gly Ser Ala Pro Ala Val Pro Glu Ala Ser Ala Ser Pro Lys Gln Arg
                85                  90                  95

Arg Ser Ile Ile Arg Asp Arg Gly Pro Met Tyr Asp Asp Pro Thr Leu
            100                 105                 110

Pro Glu Gly Trp Thr Arg Lys Leu Lys Gln Arg Lys Ser Gly Arg Ser
        115                 120                 125

Ala Gly Lys Tyr Asp Val Tyr Leu Ile Asn Pro Gln Gly Lys Ala Phe
    130                 135                 140

Arg Ser Lys Val Glu Leu Ile Ala Tyr Phe Glu Lys Val Gly Asp Thr
145                 150                 155                 160
```

Ser Leu Asp Pro Asn Asp Phe Asp Phe Thr Val Thr Gly Arg Gly Ser
            165                 170                 175

Pro Ser Arg Arg Glu Gln Lys Pro Pro Lys Pro Lys Ser Pro Lys
        180                 185                 190

Ala Pro Gly Thr Gly Arg Gly Arg Pro Lys Gly Ser Gly Thr
        195                 200                 205

Thr Arg Pro Lys Ala Ala Thr Ser Glu Gly Val Gln Val Lys Arg Val
210                 215                 220

Leu Glu Lys Ser Pro Gly Lys Leu Leu Val Lys Met Pro Phe Gln Thr
225                 230                 235                 240

Ser Pro Gly Gly Lys Ala Glu Gly Gly Ala Thr Thr Ser Thr Gln
            245                 250                 255

Val Met Val Ile Lys Arg Pro Gly Arg Lys Arg Lys Ala Glu Ala Asp
            260                 265                 270

Pro Gln Ala Ile Pro Lys Lys Arg Gly Arg Lys Pro Gly Ser Val Val
            275                 280                 285

Ala Ala Ala Ala Ala Glu Ala Lys Lys Lys Ala Val Lys Glu Ser Ser
            290                 295                 300

Ile Arg Ser Val Gln Glu Thr Val Leu Pro Ile Lys Lys Arg Lys Thr
305                 310                 315                 320

Arg Glu Thr Val Ser Ile Glu Val Lys Glu Val Val Lys Pro Leu Leu
                325                 330                 335

Val Ser Thr Leu Gly Glu Lys Ser Gly Lys Gly Leu Lys Thr Cys Lys
                340                 345                 350

Ser Pro Gly Arg Lys Ser Lys Glu Ser Ser Pro Lys Gly Arg Ser Ser
            355                 360                 365

Ser Ala Ser Ser Pro Pro Lys Lys Glu His His His His His His
        370                 375                 380

Ser Glu Ser Pro Lys Ala Pro Val Pro Leu Leu Pro Pro Leu Pro Pro
385                 390                 395                 400

Pro Pro Pro Glu Pro Glu Ser Ser Glu Asp Pro Thr Ser Pro Pro Glu
                405                 410                 415

Pro Gln Asp Leu Ser Ser Ser Val Cys Lys Glu Glu Lys Met Pro Arg
            420                 425                 430

Gly Gly Ser Leu Glu Ser Asp Gly Cys Pro Lys Glu Pro Ala Lys Thr
            435                 440                 445

Gln Pro Ala Val Ala Thr Ala Ala Thr Ala Ala Glu Lys Tyr Lys His
        450                 455                 460

Arg Gly Glu Gly Glu Arg Lys Asp Ile Val Ser Ser Ser Met Pro Arg
465                 470                 475                 480

Pro Asn Arg Glu Glu Pro Val Asp Ser Arg Thr Pro Val Thr Glu Arg
                485                 490                 495

Val Ser

<210> SEQ ID NO 11
<211> LENGTH: 28
<212> TYPE: DNA
<213> ORGANISM: Artificial
<220> FEATURE:
<223> OTHER INFORMATION: Synthetic DNA primer

<400> SEQUENCE: 11
acccattatc cagatgtgtt tgcccgag                                          28

<210> SEQ ID NO 12

```
<211> LENGTH: 26
<212> TYPE: DNA
<213> ORGANISM: Artificial
<220> FEATURE:
<223> OTHER INFORMATION: Synthetic DNA primer

<400> SEQUENCE: 12
atggtgaagc tgggcatagg cggcag                                              26

<210> SEQ ID NO 13
<211> LENGTH: 24
<212> TYPE: DNA
<213> ORGANISM: Artificial
<220> FEATURE:
<223> OTHER INFORMATION: Synthetic DNA primer

<400> SEQUENCE: 13
cgagaggacc ccgtggatgc agag                                                24

<210> SEQ ID NO 14
<211> LENGTH: 24
<212> TYPE: DNA
<213> ORGANISM: Artificial
<220> FEATURE:
<223> OTHER INFORMATION: Synthetic DNA primer

<400> SEQUENCE: 14
ggcggccatc ttcagcttct ccag                                                24

<210> SEQ ID NO 15
<211> LENGTH: 20
<212> TYPE: DNA
<213> ORGANISM: Artificial
<220> FEATURE:
<223> OTHER INFORMATION: Synthetic DNA primer

<400> SEQUENCE: 15
tctgtggaga acgacatcca                                                     20

<210> SEQ ID NO 16
<211> LENGTH: 21
<212> TYPE: DNA
<213> ORGANISM: Artificial
<220> FEATURE:
<223> OTHER INFORMATION: Synthetic DNA primer

<400> SEQUENCE: 16
ctgtacgtct cagctctgtg a                                                   21

<210> SEQ ID NO 17
<211> LENGTH: 19
<212> TYPE: DNA
<213> ORGANISM: Artificial
<220> FEATURE:
<223> OTHER INFORMATION: Synthetic DNA primer

<400> SEQUENCE: 17
aaaagcccac tccagcatc                                                      19

<210> SEQ ID NO 18
<211> LENGTH: 20
<212> TYPE: DNA
<213> ORGANISM: Artificial
<220> FEATURE:
<223> OTHER INFORMATION: Synthetic DNA primer

<400> SEQUENCE: 18
```

```
cagacaatcc agcacatctc                                               20

<210> SEQ ID NO 19
<211> LENGTH: 20
<212> TYPE: DNA
<213> ORGANISM: Artificial
<220> FEATURE:
<223> OTHER INFORMATION: Synthetic DNA primer

<400> SEQUENCE: 19
accacagtcc atgccatcac                                               20

<210> SEQ ID NO 20
<211> LENGTH: 20
<212> TYPE: DNA
<213> ORGANISM: Artificial
<220> FEATURE:
<223> OTHER INFORMATION: Synthetic DNA primer

<400> SEQUENCE: 20
tccaccaccc tgttgctgta                                               20
```

METHOD FOR PREPARING AN X CHROMOSOME INACTIVATED FEMALE HUMAN NEURAL CELL

CROSS-REFERENCES TO RELATED APPLICATIONS

This application is a national phase application of PCT Application No. PCT/US2010/062080, filed Dec. 23, 2010, which claims the benefit of U.S. Provisional Application No. 61/289,863, filed Dec. 23, 2009, all of which are incorporated herein by reference in their entirety and for all purposes.

STATEMENT AS TO RIGHTS TO INVENTIONS MADE UNDER FEDERALLY SPONSORED RESEARCH OR DEVELOPMENT

This invention was made with Government support under grant 1-DP2-OD006495-01 awarded by the National Institutes of Health.

BACKGROUND OF THE INVENTION

Autism spectrum disorders (ASD) are complex neurodevelopmental diseases affecting 1 in 150 children in the United States See e.g., MMWR Surveill Summ 56 (1):1-11 (2007). Such diseases are mainly characterized by impaired social interaction and repetitive behavior. Family history and twin studies suggest that, in some cases, these disorders share genetic roots, but the degree to which environmental and genetic patterns account for individual differences within ASD is currently unknown. See e.g., Piven, J. et al., 1997, The American Journal of Psychiatry 154 (2):185-190; Ronald, A. et al., 2006, J Am Acad Child Adolesc Psychiatry 45 (6):691-699. Several reports suggest that many autistic patients have novel genetic alterations, such as SNPs, deletions and duplications in their genomes. See e.g., Sebat, J. et al., 2007, Science 316(5823):445-449; Glessner, J. T. et al., 2009, Nature 459:1461-1465. A different combination of genetic mutations is likely to play a role in each individual. Nevertheless, the study of mutations in specific genes can help to identify molecular mechanisms responsible for subtle alterations in the nervous system, pointing to common mechanisms for ASD.

Rett syndrome (RTT) is a progressive neurological disorder caused by mutations in the X-linked gene encoding MeCP2 protein. See e.g., Amir, R. E. et al. 1999, Nat Genet 23 (2):185-188. RTT patients have a large spectrum of autistic characteristics and are considered part of the ASD population. See e.g., Samaco, R. C. et al., 2004, Hum Mol Genet 13 (6):629-639; Zappella, M. et al., 2003, Am J Med Genet B Neuropsychiatr Genet 119 (1):102-107; Hammer, S. et al., 2002, Ment Retard Dev Disabil Res Rev 8(2):94-98; Samaco, R. C. et al., 2005, Hum Mol Genet 14 (4):483-492. These individuals undergo apparently normal development until 6-18 months of age, followed by impaired motor function, stagnation and then regression of developmental skills, hypotonia, seizures and autistic behavior. See e.g., Amir, R. E. et al, 1999, Id.; Amir, R. E. & Zoghbi, H. Y., 2000, Am J Med Genet 97 (2):147-152. MeCP2 may be involved in the epigenetic regulation of target genes, by binding to methylated CpG dinucleotides within promoters, and may function as a transcriptional repressor, although this view has been challenged recently. See e.g., Yasui, D. H. et al., 2007, Proc Natl Acad Sci USA 104 (49):19416-19421; Chahrour, M. et al., 2008, Science 320 (5880):1224-1229.

Without wishing to be bound by any theory, it is believed that genes misregulated by MeCP2 mutations are probably responsible for the phenotypic abnormalities observed rather than the MeCP2 gene itself. However, microarray analyses comparing gene expression in RTT patients or RTT mouse models to wild type (WT) controls have failed to identify many genes with robust changes in gene expression. See, e.g., Traynor, J. et al., 2002, BMC Medical Genetics 3:12; Tudor, M. et al., 2003, Proc Natl Acad Sci USA 99(24): 15536-15541. Such subtle gene expression changes will probably target genes expressed only in specific brain regions or neurons that are, therefore, being masked in the analyses of entire brain regions. In support of this argument, a recent study revealed changes in the expression levels of thousands of genes by focusing on mouse hypothalamus only instead of whole brain. See Chahrour, M. et al., 2008, Science 320(5880):1224-1229. It is further believed that such analysis may not determine the affected cell type due to cellular heterogeneity. Furthermore, MeCP2 regulation of target genes is very likely developmental-stage specific. Finally, the majority of the work has been focused on mouse models of RTT or postmortem brain samples, and an in vitro human developmental model of RTT has been lacking.

Pluripotent human embryonic stem cells (hESCs) have been successfully generated from early stage human embryos and can differentiate into various cell types. See, e.g., Thomson, J. A. et al., 1998, Science 282(5391):1145-1147. However, to develop cellular models of human disease, it is necessary to generate cell lines with genomes pre-disposed to diseases. Recently, reprogramming of somatic cells to a pluripotent state by over-expression of specific genes (induced pluripotent stem cells, iPSCs) has been accomplished. See, e.g., Takahashi, K. & Yamanaka, S., 2006, Cell 126(4):663-676; Takahashi, K. et al., 2007, Cell 131 (5):861-872; Yu, J. et al., 2007, Science 318(5858): 1917-1920. Resultant iPSCs are isogenic to the donor individual, i.e., they carry the identical genetic background. Isogenic pluripotent cells are attractive not only for their potential therapeutic use with lower risk of immune rejection but also for understanding complex diseases. See, e.g., Marchetto et al., 2010, Cell 143:527-539; Muotri, A. R., 2009, Epilepsy Behav 14:Suppl. 1, 81-85. Although iPSCs have been generated for several neurological diseases (Dimos et al., 2008, Science 321:1218-1221; Ebert et al., 2009, Nature 457:277-280; Hotta et al., 2009, Nat. Methods 6:370-376; Lee et al., 2009, Nature 461:402-406; Park et al., 2008, Cell 134:877-886; Soldner et al., 2009, Cell 136:964-977), the demonstration of disease-specific pathogenesis and phenotypic rescue in relevant cell types is a current challenge in the field (Marchetto et al. 2010, id).

Thus, there is a need in the art for methods and compositions useful in identifying compounds useful in treating a neurological disorder. The present invention addresses these and other needs in the art.

BRIEF SUMMARY OF THE INVENTION

In one aspect, an X chromosome inactivated female human neural cell derived from an induced pluripotent stem cell is provided.

In another aspect, a plurality of X chromosome inactivated female human neural cells are provided that are derived from a plurality of induced pluripotent stem cells. The X chromosome inactivated female human neural cells can be neural progenitor cells or neuronal cells. Each of the X chromosome inactivated female human neural cells includes a first X chromosome and a second X chromosome.

The second X chromosome includes a mutated gene, where a portion of the plurality of X chromosome inactivated female human neural cells include an inactive first X chromosome and an active second X chromosome and another portion of the plurality of X chromosome inactivated female human neural cells include an active first X chromosome and an inactive second X chromosome.

In another aspect, a method of identifying a compound useful in treating a neurological disorder is provided. The method includes contacting a test compound with a plurality of X chromosome inactivated female human neural cells (e.g. as described in the preceding paragraph). The level of neurological functionality of the plurality of X chromosome inactivated female human neural cells is determined. The level of neurological functionality of the plurality of X chromosome inactivated female human neural cells in the presence of the test compound is compared to a control thereby identifying a compound useful in treating a neurological disorder.

BRIEF DESCRIPTION OF THE DRAWINGS

FIG. 1. Generation of iPSCs. FIG. 1C: Aspect of iPSCs colonies 14 days after infection. FIGS. 1D-1E: Representative images of established iPSC colonies as described herein. FIGS. 1F-1G: Representative images of RTT-iPSCs showing expression of pluripotent markers Dapi, Nanog, Tra-1-81 and merge (FIG. 1F), and Dapi, Lin28, Sox2 and merge (FIG. 1G). FIG. 1I: Representative images of teratoma sections depicting endoderm, mesoderm and ectoderm in WT-iPSC and RTT-iPSC. Bar=100 μm. See also FIG. 7.

FIG. 5. Altered activity-dependent calcium transients in RTT-derived neurons.

FIG. 6. Decreased frequency of spontaneous postsynaptic currents in RTT neurons.

FIG. 7. Generation of iPSCs derived from RTT patients' fibroblasts carrying distinct mutations in the MeCP2 gene; related to FIG. 1. FIG. 7A: Morphology of fibroblasts before retroviral infection. FIG. 7B: Aspect of iPSCs colonies growing in the absence of feeder layer. Colonies are compact and have well-defined borders. Cells display high nucleus-to-cytoplasm ratio and are morphologically similar to hESCs. FIG. 7C: Representative immunofluorescence analysis of RTT-iPSC clones. Expression of pluripotent markers such as Nanog and Tra-1-81 is observed. Bar=100 μm. Y-axis labels for FIGS. 7B-7C are as indicated for FIG. 7A. FIG. 7E: Reprogrammed iPSCs showed expressions similar to hESC-enriched genes (Lin28, CXADR, Nanog and PTRZ1; black bars) and showed distinct differences from fibroblast-enriched genes (GREM1, MMP1, DKK1 and PTX3; white bars). Legend: for each histogram of FIG. 7E, the X-axis species appear in the order (left to right): HUES6; Fibroblast WT; Fibroblast RTT; iPSC-WT cl (clone) 1; iPSC-WT cl 2; iPSC-RTT cl 15; iPSC-RTT cl 18.

FIG. 8. Neuronal differentiation from individual WT and RTT-iPSC clones; related to FIG. 2. Clones from WT and RTT-iPSCs were differentiated into neurons for approximately 1 month. FIG. 8A: WT-AG09319 C1; WT-ADRC40; WT-33 C1; WT-126 C5; WT-126 C8; RTT-1155del32 C15; RTT-1155del32 C18; RTT-Q244X C3; RTT-Q244X C4; RTT-T158M C3. FIG. 8B: WT-33 C1; WT-126 C8; RTT-1155del32 C15; RTT-1155del32 C18; RTT-Q244X C3. FIG. 8C: WT-AG09319 C1; WT-33 C1; WT-126 C8; RTT-1155del32 C15; RTT-Q244X C3; RTT-T158M C3. Data shown as mean±s.e.m.

FIG. 9. Androgen receptor analysis; related to FIG. 3. Example of X-inactivation analysis using the X-linked androgen receptor locus for the RTT-1155del32 C15 genomic DNA. After the PCR, two different sized amplicons were detected (different peaks) and digested with a methylation-sensitive restriction enzyme (HpaII). The PCR using undigested DNA shows if two distinct alleles are present and also allows a correction factor due to the advantage on the amplification of the smaller allele. When the template DNA is digested, amplification occurs if the restriction sites are methylated. If the site is unmethylated, digestion will occur between the flanking oligonucleotides and amplification will not be possible. The peak areas after HpaII restriction digestion of genomic DNA are used to distinguish each parental X chromosome.

FIG. 10. Phenotypic analysis iPSC-derived neurons from several clones; related to FIG. 4.

FIG. 11. Calcium transient analysis in iPSC-derived neurons; related to FIG. 5. Neurons were selected after the confirmation that calcium transients were blocked with 1 μM of TTX or the glutamate receptor antagonists CNQX/APV treatments. FIG. 11A: Blocking glutamatergic signaling in the neuronal network using CNQX and APV resulted in significant reduction in intracellular calcium transients.

DETAILED DESCRIPTION OF THE INVENTION

I. Definitions

Figure 1A:
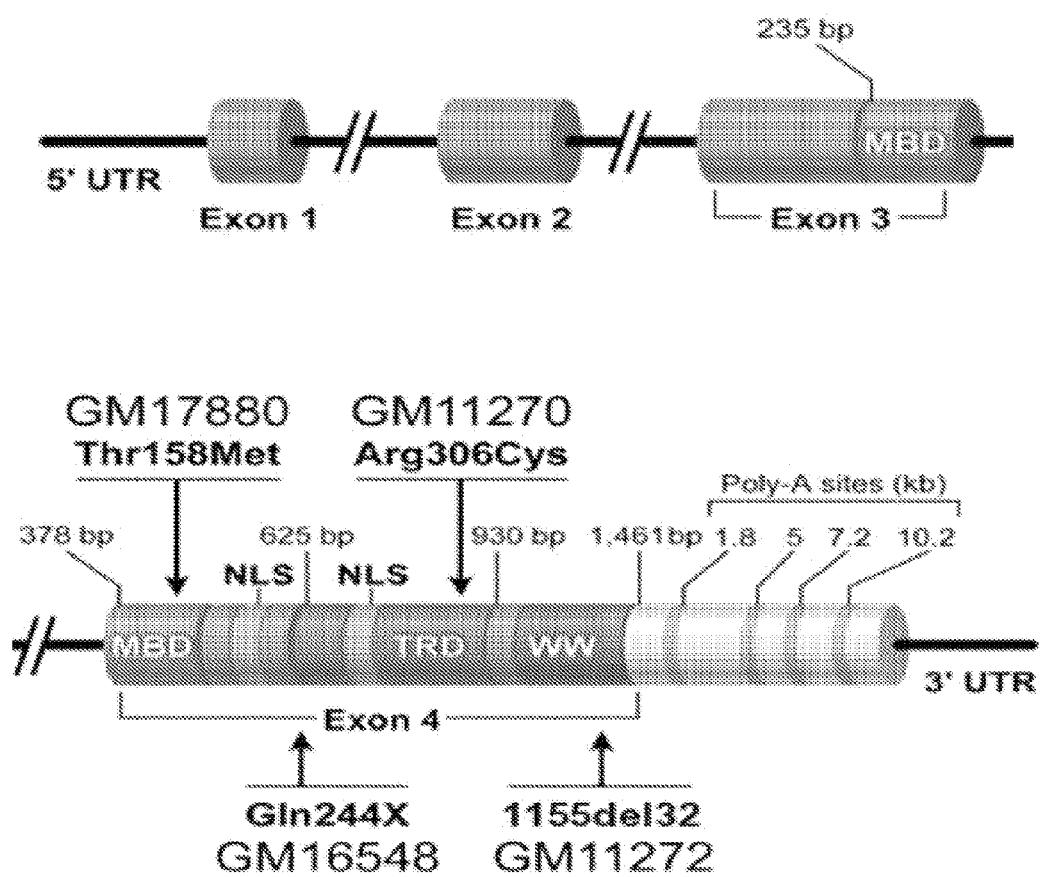
FIG. 1A: Schematic representation of the MeCP2 gene structure and mutations as described herein. UTR, untranslated region; MBD, methyl-CpG binding domain; NLS, nuclear localization signal; Poly-A, polyadenylation signal; TRD, transcriptional repression domain; WW, domain containing WW (two tryptophans); X, stop codon. Respective cell lines codes are shown close to their mutations.

Unless defined otherwise, technical and scientific terms used herein have the same meaning as commonly understood by a person of ordinary skill in the art. See, e.g., Singleton et al., DICTIONARY OF MICROBIOLOGY AND MOLECULAR BIOLOGY 2nd ed., J. Wiley & Sons (New York, N.Y. 1994); Sambrook et al., MOLECULAR CLONING, A LABORATORY MANUAL, Cold Springs Harbor Press (Cold Springs Harbor, N.Y. 1989). Any methods, devices and materials similar or equivalent to those described herein can be used in the practice of this invention. The following definitions are provided to facilitate understanding of certain terms used frequently herein and are not meant to limit the scope of the present disclosure.

"Nucleic acid" refers to deoxyribonucleotides or ribonucleotides and polymers thereof in either single- or double-stranded form, and complements thereof.

The words "complementary" or "complementarity" refer to the ability of a nucleic acid in a polynucleotide to form a base pair with another nucleic acid in a second polynucleotide. For example, the sequence A-G-T is complementary to the sequence T-C-A. Complementarity may be partial, in which only some of the nucleic acids match according to base pairing, or complete, where all the nucleic acids match according to base pairing.

The terms "identical" or percent "identity," in the context of two or more nucleic acids, refer to two or more sequences or subsequences that are the same or have a specified percentage of nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region, when compared and aligned for maximum correspondence over a comparison window or designated region) as measured using a BLAST or BLAST 2.0 sequence comparison algorithms with default parameters described below, or by manual alignment and visual inspection. See, e.g., the NCBI web site or the like. Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

The phrase "stringent hybridization conditions" refers to conditions under which a probe will hybridize to its target sequence, typically in a complex mixture of nucleic acids, but to not other sequences. Stringent conditions are sequence-dependent and will be different in different circumstances. Longer sequences hybridize specifically at higher temperatures. An extensive guide to the hybridization of nucleic acids is found in Tijssen, TECHNIQUES IN BIOCHEMISTRY AND MOLECULAR BIOLOGY—HYBRIDIZATION WITH NUCLEIC PROBES, "Overview of principles of hybridization and the strategy of nucleic acid assays" (1993). Generally, stringent conditions are selected to be about 5-10° C. lower than the thermal melting point (Tm) for the specific sequence at a defined ionic strength pH. The Tm is the temperature (under defined ionic strength, pH, and nucleic concentration) at which 50% of the probes complementary to the target hybridize to the target sequence at equilibrium (as the target sequences are present in excess, at Tm, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

A variety of methods of specific DNA and RNA measurement that use nucleic acid hybridization techniques are known to those of skill in the art (see, Sambrook, Id.). Some methods involve electrophoretic separation (e.g., Southern blot for detecting DNA, and Northern blot for detecting RNA), but measurement of DNA and RNA can also be carried out in the absence of electrophoretic separation (e.g., by dot blot).

The sensitivity of the hybridization assays may be enhanced through use of a nucleic acid amplification system that multiplies the target nucleic acid being detected. Examples of such systems include the polymerase chain reaction (PCR) system and the ligase chain reaction (LCR) system. Other methods recently described in the art are the nucleic acid sequence based amplification (NASBA, Cangene, Mississauga, Ontario) and Q Beta Replicase systems. These systems can be used to directly identify mutants where the PCR or LCR primers are designed to be extended or ligated only when a selected sequence is present. Alternatively, the selected sequences can be generally amplified using, for example, nonspecific PCR primers and the amplified target region later probed for a specific sequence indicative of a mutation. It is understood that various detection probes, including Taqman® and molecular beacon probes can be used to monitor amplification reaction products, e.g., in real time.

The word "polynucleotide" refers to a linear sequence of nucleotides. The nucleotides can be ribonucleotides, deoxyribonucleotides, or a mixture of both. Examples of polynucleotides contemplated herein include single and double stranded DNA, single and double stranded RNA (including miRNA), and hybrid molecules having mixtures of single and double stranded DNA and RNA.

The words "protein", "peptide", and "polypeptide" are used interchangeably to denote an amino acid polymer or a set of two or more interacting or bound amino acid polymers.

The term "gene" means the segment of DNA involved in producing a protein; it includes regions preceding and following the coding region (leader and trailer) as well as intervening sequences (introns) between individual coding segments (exons). The leader, the trailer as well as the introns include regulatory elements that are necessary during the transcription and the translation of a gene. Further, a "protein gene product" is a protein expressed from a particular gene.

The word "expression" or "expressed" as used herein in reference to a gene means the transcriptional and/or translational product of that gene. The level of expression of a DNA molecule in a cell may be determined on the basis of either the amount of corresponding mRNA that is present within the cell or the amount of protein encoded by that DNA produced by the cell (Sambrook et al., 1989, *Molecular Cloning: A Laboratory Manual*, 18.1-18.88).

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell.

The term "plasmid" refers to a nucleic acid molecule that encodes for genes and/or regulatory elements necessary for the expression of genes. Expression of a gene from a plasmid can occur in cis or in trans. If a gene is expressed in cis, gene and regulatory elements are encoded by the same plasmid. Expression in trans refers to the instance where the gene and the regulatory elements are encoded by separate plasmids.

A "vector" is a nucleic acid that is capable of transporting another nucleic acid into a cell. A vector is capable of directing expression of a protein or proteins encoded by one or more genes carried by the vector when it is present in the appropriate environment.

A "viral vector" is a viral-derived nucleic acid that is capable of transporting another nucleic acid into a cell. A viral vector is capable of directing expression of a protein or proteins encoded by one or more genes carried by the vector when it is present in the appropriate environment. Examples for viral vectors include, but are not limited to retroviral, adenoviral, lentiviral and adeno-associated viral vectors.

A "cell culture" is a population of cells residing outside of an organism. These cells are optionally primary cells isolated from a cell bank, animal, or blood bank, or secondary cells that are derived from one of these sources and have been immortalized for long-lived in vitro cultures.

A "stem cell" is a cell characterized by the ability of self-renewal through mitotic cell division and the potential to differentiate into a tissue or an organ. Among mammalian stem cells, embryonic and somatic stem cells can be distinguished. Embryonic stem cells reside in the blastocyst and give rise to embryonic tissues, whereas somatic stem cells reside in adult tissues for the purpose of tissue regeneration and repair.

The term "pluripotent" or "pluripotency" refers to cells with the ability to give rise to progeny that can undergo differentiation, under appropriate conditions, into cell types that collectively exhibit characteristics associated with cell lineages from the three germ layers (endoderm, mesoderm, and ectoderm). Pluripotent stem cells can contribute to tissues of a prenatal, postnatal or adult organism. A standard art-accepted test, such as the ability to form a teratoma in 8-12 week old SCID mice, can be used to establish the pluripotency of a cell population. However, identification of various pluripotent stem cell characteristics can also be used to identify pluripotent cells.

"Pluripotent stem cell characteristics" refer to characteristics of a cell that distinguish pluripotent stem cells from other cells. Expression or non-expression of certain combinations of molecular markers are examples of characteristics of pluripotent stem cells. More specifically, human pluripotent stem cells may express at least some, and optionally all, of the markers from the following non-limiting list: SSEA-3, SSEA-4, TRA-1-60, TRA-1-81, TRA-2-49/6E, ALP, Sox2, E-cadherin, UTF-1, Oct4, Lin28, Rex1, and Nanog. Cell morphologies associated with pluripotent stem cells are also pluripotent stem cell characteristics.

The term "reprogramming" refers to the process of dedifferentiating a non-pluripotent cell into a cell exhibiting pluripotent stem cell characteristics.

The term "treating" means ameliorating, suppressing, eradicating, and/or delaying the onset of the disease being treated.

The terms "induced pluripotent stem cell," "iPS," "iPSC" and the like refer to a pluripotent stem cell artificially derived from a non-pluripotent cell. A "non-pluripotent cell" can be a cell of lesser potency to self-renew and differentiate than a pluripotent stem cell. Cells of lesser potency can be, but are not limited to adult stem cells, tissue specific progenitor cells, primary or secondary cells. An adult stem cell is an undifferentiated cell found throughout the body after embryonic development. Adult stem cells multiply by cell division to replenish dying cells and regenerate damaged tissue. Adult stem cells have the ability to divide and create another cell like itself and also divide and create a cell more differentiated than itself. Even though adult stem cells are associated with the expression of pluripotency markers such as Rex1, Nanog, Oct4 or Sox2, they do not have the ability of pluripotent stem cells to differentiate into the cell types of all three germ layers. Adult stem cells have a limited potency to self renew and generate progeny of distinct cell types. Without limitation, an adult stem cell can be a hematopoietic stem cell, a cord blood stem cell, a mesenchymal stem cell, an epithelial stem cell, a skin stem cell or a neural stem cell. A tissue specific progenitor refers to a cell devoid of self-renewal potential that is committed to differentiate into a specific organ or tissue. A primary cell includes any cell of an adult or fetal organism apart from egg cells, sperm cells and stem cells. Examples of useful primary cells include, but are not limited to, skin cells, bone cells, blood cells, cells of internal organs and cells of connective tissue. A secondary cell is derived from a primary cell and has been immortalized for long-lived in vitro cell culture.

A "somatic cell" is a cell forming the body of an organism. Somatic cells include cells making up organs, skin, blood, bones and connective tissue in an organism, but not germline cells.

The teen "transfection" or "transfecting" is defined as a process of introducing nucleic acid molecules to a cell by non-viral or viral-based methods. The nucleic acid molecules may be gene sequences encoding complete proteins or functional portions thereof.

Non-viral methods of transfection include any appropriate transfection method that does not use viral DNA or viral particles as a delivery system to introduce the nucleic acid molecule into the cell. Exemplary non-viral transfection methods include calcium phosphate transfection, liposomal transfection, nucleofection, sonoporation, transfection through heat shock, magnetifection and electroporation. In some embodiments, the nucleic acid molecules are introduced into a cell using electroporation following standard procedures well known in the art. For viral-based methods of transfection any useful viral vector may be used in the methods described herein. Examples for viral vectors include, but are not limited to retroviral, adenoviral, lentiviral and adeno-associated viral vectors. In some embodiments, the nucleic acid molecules are introduced into a cell using a retroviral vector following standard procedures well known in the art.

Expression of a transfected gene can occur transiently or stably in a cell. During "transient expression" the transfected gene is not transferred to the daughter cell during cell division. Since its expression is restricted to the transfected cell, expression of the gene is lost over time. In contrast, stable expression of a transfected gene can occur when the gene is co-transfected with another gene that confers a selection advantage to the transfected cell. Such a selection advantage may be a resistance towards a certain toxin that is presented to the cell. Expression of a transfected gene can further be accomplished by transposon-mediated insertion into the host genome. During transposon-mediated insertion the gene is positioned between two transposon linker sequences that allow insertion into the host genome as well as subsequent excision.

The term "Yamanaka factors" refers to Oct3/4, Sox2, Klf4, and c-Myc, which factors are highly expressed in embryonic stem (ES) cells. Without wishing to be bound by any theory, it is believed that over-expression of the Yamanaka factors can induce pluripotency in somatic cells from a variety of species, e.g., mouse and human somatic cells. See, e.g., Yamanaka, 2009, *Cell* 137: 13-17.

A "KLF4 protein" as referred to herein includes any of the naturally-occurring forms of the KLF4 transcription factor, or variants thereof that maintain KLF4 transcription factor activity (e.g., within at least 50%, 80%, 90%, 95%, 96%, 97%, 98%, 99% or 100% activity compared to KLF4). In some embodiments, variants have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring KLF4 polypeptide (e.g., SEQ ID NO:1). In other embodiments, the KLF4 protein is the protein as identified by the NCBI reference gi:194248077 (SEQ ID NO:1).

An "OCT4 protein" as referred to herein includes any of the naturally-occurring forms of the Octomer 4 transcription factor, or variants thereof that maintain Oct4 transcription factor activity (e.g. within at least 50%, 80%, 90%, 95%, 96%, 97%, 98%, 99% or 100% activity compared to Oct4). In some embodiments, variants have at least 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring Oct4 polypeptide (e.g., SEQ ID NO:2, SEQ ID NO:3 or SEQ ID NO:4). In other embodiments, the Oct4 protein is the protein as identified by the NCBI reference gi:42560248 corresponding to isoform 1 (SEQ ID NO:2), gi:116235491 and gi:291167755 corresponding to isoform 2 (SEQ ID NO:3 and SEQ ID NO:4).

A "Sox2 protein" as referred to herein includes any of the naturally-occurring forms of the Sox2 transcription factor, or variants thereof that maintain Sox2 transcription factor activity (e.g., within at least 50%, 80%, 90%, 95%, 96%, 97%, 98%, 99% or 100% activity compared to Sox2). In some embodiments, variants have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring Sox2 polypeptide (e.g., SEQ ID NO:5). In other embodiments, the Sox2 protein is the protein as identified by the NCBI reference gi:28195386 (SEQ ID NO:5).

A "cMYC protein" as referred to herein includes any of the naturally-occurring forms of the cMyc transcription factor, or variants thereof that maintain cMyc transcription factor activity (e.g., within at least 50%, 80%, 90%, 95%, 96%, 97%, 98%, 99% or 100% activity compared to cMyc). In some embodiments, variants have at least 90%, 95%, 96%, 97%, 98%, 99% or 100% amino acid sequence identity across the whole sequence or a portion of the sequence (e.g., a 50, 100, 150 or 200 continuous amino acid portion) compared to a naturally occurring cMyc polypeptide (e.g., SEQ ID NO:6). In other embodiments, the cMyc protein is the protein as identified by the NCBI reference gi:71774083 (SEQ ID NO:6).

The term "feeder-free" refers to the absence of feeder cells. The term "feeder cell" is generally well known in the art and includes all cells used to support the propagation of stem cells during the process of reprogramming. Feeder cells may be irradiated prior to being co-cultured with the cells being reprogrammed in order to avoid the feeder cells to overgrow the cells undergoing reprogramming. Feeder cells produce growth factors that support cells during the process of reprogramming and also provide a layer physical support for the reprogrammed cells to attach to. Examples of feeder cells include fibroblasts, splenocytes, macrophages and thymocytes.

II. Methods and Compositions iPSC-Derived X Chromosome Inactivated Female Human Neural Cells In one aspect, an X chromosome inactivated female human neural cell derived from an induced pluripotent stem cell is provided. Human female somatic cells have two X chromosomes, one of which is inactive such that the female cell does not contain twice the number of X chromosome gene products as a human male cell. Where an X chromosome is referred to herein as inactive or inactivated, it is used in accordance with its generally known meaning in the art. As such, an X chromosome inactivated human female cell is a human female cell in which one of the two X chromosomes present in the human female cell is silent with respect to X chromosome gene expression.

A human neural cell is a cell associated with the human nervous system. Examples of human neural cells include but are not limited to neural stem cells, neural progenitor cells, neuron, and glial cells. In some embodiments, a human neural cell is a neural progenitor cell or a neuronal cell. In some embodiments, a human neural cell is a neural progenitor cell. A neural progenitor cell is a neural cell capable of differentiating into a specific neuronal cell type but incapable of replicating indefinitely (e.g., can only divide a limited number of times). As used herein, the term "differentiating" refers to a process by which a less specialized cell type becomes a more specialized cell type. In some embodiments, a human neural cell is a neuronal cell. A neuronal cell is a further differentiated neural cell, such as a neuron (e.g., a cholinergic, GABAergic, glutamatergic, dopaminergic and serotonergic neuron) or a glial cell (e.g., astrocyte, microglial cell, Schwann cell, etc.).

In some embodiments, the X chromosome inactivated female human neural cell includes a mutated X chromosome linked gene. In some embodiments, the mutated X chromosome linked gene is capable of causing a neurological disorder when found in a human. In some embodiments, the mutated X chromosome linked gene is capable of causing an autism spectrum disorder (e.g., autism or Rett syndrome). In some embodiments, the mutated X chromosome linked gene is a mutated X-linked gene encoding MeCP2. "MeCP2" as referred to herein stands for methyl CpG binding protein 2 and includes any of the naturally-occurring forms of the MeCP2 gene or protein, or variants thereof that maintain MeCP2 activity (e.g., within at least 50%, 80%, 90%, 95%, 96%, 97%, 98%, 99% or 100% activity compared to MeCP2). In some embodiments, variants have at least 70%, 75%, 80%, 85%, 90%, 95%, 96%, 97%, 98%, 99% or 100% amino acid sequence identity across the whole sequence or a portion of the sequence (e.g. a 50, 100, 150 or 200 continuous amino acid portion) compared to a naturally occurring MeCP2 polypeptide (e.g., SEQ ID NO:8 (MeCP2 isoform 1 protein) or SEQ ID NO:10 (MeCP2 isoform 2 protein)) or polynucleotide encoding an MeCP2 polypeptide (e.g., SEQ ID NO:7 (MeCP2 isoform 1 nucleic acid) or SEQ ID NO:9 (MeCP2 isoform 2 nucleic acid)). In some embodiments, the MeCP2 nucleic acid is the nucleic acid as identified by GenBank Accession Nos. NM_004992 (MeCP2 isoform 1 DNA; SEQ ID NO:7) or NM_001110792 (MeCP2 isoform 2 DNA; SEQ ID NO:9). In some embodiments, the MeCP2 protein is the protein as identified by GenBank Accession Nos. NP_004983 (MeCP2 isoform 1 protein; SEQ ID NO:8) and NP_001104262 (MeCP2 isoform 2 protein; SEQ ID NO:10). In some embodiments, the induced pluripotent stem cell from which the X chromosome inactivated female human neural cell is obtained (e.g., derived) from a patient having a neurological disorder. In some embodiments, the induced pluripotent stem cell from which the X chromosome inactivated female human neural cell is obtained (e.g., derived) from a patient having an autism spectrum disorder. In some embodiments, the induced pluripotent stem cell from which the X chromosome inactivated female human neural cell is obtained (e.g., derived) from a patient having autism, Rett syndrome, Alzheimer's disease, Parkinson's disease, Charcot-Marie-Tooth disease, Myasthenia Gravis, multiple sclerosis, or chronic demyelinating polyneuropathy and the like. In some embodiments, the induced pluripotent stem cell from which the X chromosome inactivated female human neural cell is obtained (e.g., derived) from a patient having autism or Rett syndrome. In some embodiments, the induced pluripotent stem cell from which the X chromosome inactivated female human neural cell is obtained (e.g., derived) from a patient having Rett syndrome.

The X chromosome inactivated female human neural cell may be prepared by a process that includes differentiating an induced pluripotent stem cell (iPSC). An induced pluripotent stem cell is typically a pluripotent stem cell that is derived non-naturally from a non-pluripotent cell, such as an adult somatic cell (e.g., generated from a non-pluripotent cell using any appropriate method as described herein). The iPSC may have two active X chromosomes, where upon differentiation of the iPSC to the X chromosome inactivated female human neural cell, one of the two active X chromosomes of is inactivated. The process may further include, prior to the differentiation of the induced pluripotent stem cell, generating the induced pluripotent stem cell from a human female somatic cell.

Any appropriate synthetic method may be used to produce an induced pluripotent stem cell, including genomic alterations (e.g., by transfection with transcriptional regulators) or treatment with proteins (e.g., protein-induced pluripotent stem cells) and/or methods as described herein. In some embodiments, iPSCs are generated by transfecting a non-pluripotent cell (e.g., a human female somatic cell) with nucleic acid encoding one or more proteins that are one or more highly expressed in embryonic stem cells. In some embodiments, the non-pluripotent cell is transfected with nucleic acids encoding one or more proteins effective to induce pluripotency (e.g., one or more Yamanaka factors). In some embodiments, the non-pluripotent cell is transfected with nucleic acids encoding a Sox2 protein, an Oct4 protein, a c-Myc protein, or a Klf4 protein. In some embodiments, the non-pluripotent cell is transfected with nucleic acids encoding a Sox2 protein, an Oct4 protein, a c-Myc protein, and a Klf4 protein. In some embodiments, the nucleic acids encoding a Sox2 protein, an Oct4 protein, a c-Myc protein, and/or a Klf4 protein are expressed in viral vectors. A viral vector may be any suitable virus (e.g., retrovirus or lentivirus). In some embodiments, the non-pluripotent cell is transfected with Sox2, Oct4, c-Myc, and Klf4-expressing viral vectors.

In some embodiments, iPSCs are differentiated into neural cells by culturing the iPSCs to generate embryoid bodies (EBs). In some embodiments, iPSCs may be differentiated into neural progenitor cells by culturing the EBs (e.g., in the presence of a medium suitable for the growth of neural progenitor cells) to form EB-derived rosettes, which are dissociated and re-plated to generate neural progenitor cells. In some embodiments, the EBs are cultured in the absence of FGF2. In some embodiments, the EBs are cultured in the presence of a protein that promotes neural induction (e.g., Noggin). Differentiation of an iPSC into a neural progenitor cell can be confirmed by detecting the presence of one or more neural precursor markers, including but not limited to Sox2, Pax6, and Musashi1. In some embodiments, iPSCs may be differentiated into neuronal cells by culturing the EBs (e.g., in the presence of a medium suitable for the growth of neuronal cells) to form mature EBs, which are then dissociated and replated to generate neuronal cells. In some embodiments, the EBs are cultured in the presence of a protein that promotes neuronal induction (e.g., retinoic acid). Differentiation of an iPSC into a neuronal cell can be confirmed by detecting the presence of one or more neuron markers, including but not limited to MAP2, MAP5, and Tuj1 (β-III-tubulin) or one or more glial cell markers, including but not limited to GFAP and O4.

The X chromosome inactivated female human neural cell may be derived from any appropriate human female somatic cell, including a human fibroblast cell. In some embodiments, the iPSC is derived from a human fibroblast cell, including but not limited to a human dermal fibroblast cell, a human lung fibroblast cell, a human dental pulp fibroblast cell, or a human adipose fibroblast cell. In some embodiments, the iPSC is derived from a human keratinocyte cell, including but not limited to a human skin keratinocyte cell or a human hair follicle keratinocyte cell. In some embodiments, the iPSC is derived from a human cell derived from tooth tissue, e.g., a cell derived from the cell rich pulp layer, preferably the innermost pulp layer, of the human tooth, cells from the odontoblastic layer, and the like as known in the art. In some embodiments, the iPSC is derived from the human fibroblast cell, human keratinocyte cell, or human cell derived from tooth tissue as described herein and used to generate the X chromosome inactivated female human neural cell. In some embodiments, the X chromosome inactivated female human neural cell that is derived from the iPSC as described herein is a neural progenitor cell. In some embodiments, the X chromosome inactivated female human neural cell that is derived from the iPSC as described herein is a neuronal cell, such as a neuron (e.g., cholinergic, GABAergic, glutamatergic, dopaminergic, or serotonergic neuron) or a glial cell (e.g., astrocytes, microglial cells, Schwann cells, etc.). In some embodiments, the X chromosome inactivated female human neural cell that is derived from the iPSC as described herein is a glutamatergic cell (e.g., a functional post-mitotic neuron which displays X-inactivation).

The human female somatic cell may include a first X chromosome and a second X chromosome. The first X chromosome may be active and the second X chromosome may be inactive. The second X chromosome may also include a mutated gene. In other embodiments the first X chromosome is inactive, the second X chromosome is active, and the second X chromosome includes a mutated gene. As used herein, a "mutated gene" refers to a gene comprising one or more modifications relative to a wild-type (i.e., naturally occurring) gene, such as substitutions, insertions, deletions, and/or truncations, wherein the one or more modifications results in an alteration in the protein encoded by the gene relative to the protein encoded by the wild-type gene.

In another aspect, a method is provided for preparing an X chromosome inactivated female human neural cell. The method includes differentiating an induced pluripotent stem cell having two active X chromosome. Upon differentiation, one of the two active X chromosomes may be inactivated. In some embodiments, the method also includes, prior to differentiating the induced pluripotent stem cell, generating the induced pluripotent stem cell from a human female somatic cell (e.g., human fibroblast cell, human keratinocyte cell, or human cell derived from tooth tissue). The human female somatic cell may include a first X chromosome and a second X chromosome, where the first X chromosome is active, the second X chromosome is inactive, and the second X chromosome comprises a mutated gene. In other embodiments, the X chromosome inactivated female human neural cell includes a first X chromosome and a second X chromosome, wherein the first X chromosome is inactive, the second X chromosome is active, and the second X chromosome comprises a mutated gene.

In some embodiments, the method includes generating an induced pluripotent stem cell from a human female somatic cell. In some embodiments, the iPSC is generated by transfecting a human female somatic cell with nucleic acid encoding one or more proteins that are one or more highly expressed in embryonic stem cells. In some embodiments, the human female somatic cell is transfected with nucleic acids encoding a Sox2 protein, an Oct4 protein, a c-Myc protein, and a Klf4 protein. In some embodiments, the nucleic acids encoding a Sox2 protein, an Oct4 protein, a c-Myc protein, and/or a Klf4 protein are expressed in viral vectors. A viral vector may be any suitable virus (e.g., retrovirus or lentivirus). In some embodiments, the human female somatic cell is transfected with Sox2, Oct4, c-Myc, and Klf4-expressing viral vectors to generate an iPSC.

In some embodiments, the method includes differentiating an induced pluripotent stem cell having two active X chromosomes. Induced pluripotent stem cells can be differentiated by any method known in the art (e.g., Marchetto, M. C. et al., *Cell Stem Cell*, 3, 649-657 (2008); Yeo, G. W. et al., *PLoS Comput Biol*, 3, 1951-1967 (2007)) or according to the methods described herein. In some embodiments, iPSCs having two active X chromosomes may be differentiated into X chromosome inactivated neural progenitor cells by culturing the EBs (e.g., in the presence of a medium suitable for the growth of neural progenitor cells) to form EB-derived rosettes, which are dissociated and re-plated to generate neural progenitor cells. In some embodiments, the EBs are cultured in the absence of FGF2. In some embodiments, the EBs are cultured in the presence of a protein that promotes neural induction (e.g., Noggin). Differentiation of an iPSC into a neural progenitor cell can be confirmed by detecting the presence of one or more neural precursor markers, including but not limited to Sox2, Pax6, and Musashi1. In some embodiments, iPSCs having two active X chromosomes may be differentiated into X chromosome inactivated neuronal cells by culturing the EBs (e.g., in the presence of a medium suitable for the growth of neuronal cells) to form mature EBs, which are then dissociated and replated to generate neuronal cells. In some embodiments, the EBs are cultured in the presence of a protein that promotes neuronal induction (e.g., retinoic acid). Differentiation of an iPSC into a neuronal cell can be confirmed by detecting the presence of one or more neuron markers, including but not limited to MAP2, MAP5, and Tuj1 (β-III-tubulin) or one or more glial cell markers, including but not limited to GFAP and O4. Activation or inactivation of an X chromosome can be detected by measuring the presence of a marker for X chromosome silencing. In some embodiments, inactivation of an X chromosome in a neural cell (e.g., a female human neural progenitor cell or a female human neuronal cell) is detected by contacting the neural cell with an antibody against trimethylated histone 3 Lysine 27 (me3H3K27). In some embodiments, inactivation of an X chromosome in a neural cell (e.g., a female human neural progenitor cell or a female human neuronal cell) is detected by contacting the neural cell with an antisense probe against Xist RNA.

In another aspect, a plurality of X chromosome inactivated female human neural cells are provided that are derived from a plurality of induced pluripotent stem cells. Each of the X chromosome inactivated female human neural cells includes a first X chromosome and a second X chromosome. The second X chromosome includes a mutated gene, where a portion of the plurality of X chromosome inactivated female human neural cells include an inactive first X chromosome and an active second X chromosome and another portion of the plurality of X chromosome inactivated female human neural cells include an active first X chromosome and an inactive second X chromosome. In some embodiments, the plurality of X chromosome inactivated female human neural cells are female human neural progenitor cells. In some embodiments, the plurality of X chromosome inactivated female human neural cells are female human neuronal cells. In some embodiments, at least a portion of the plurality of X chromosome inactivated female human neural cells are operably linked to form a neural network (i.e., a collection of neural cells in which at least some of the neural cells interact neurologically). In certain embodiments, the mutated gene is capable of causing a neurological disorder when found in a human. Applicable neurological disorders are discussed below. The mutated gene may encode MeCP2.

The induced pluripotent stem cell-derived X chromosome inactivated female human neural cells as described above can be used in the following methods.

Methods of Identifying a Compound Useful in Treating a Neurological Disorder

In another aspect, a method of identifying a compound useful in treating a neurological disorder is provided. The method includes contacting a test compound with a plurality of X chromosome inactivated female human neural cells (e.g., human neural progenitor cells or human neuronal cells as described above). The level of neurological functionality of the plurality of X chromosome inactivated female human neural cells is determined. The level of neurological functionality of the plurality of X chromosome inactivated female human neural cells in the presence of the test compound is compared to a control, thereby identifying a compound useful in treating a neurological disorder.

A change in the level of neurological functionality in the presence of the test compound relative to the control that correlates to desired neurological functionality is indicative of a compound useful in treating a neurological disorder. Any appropriate control may be used, including the level of neurological functionality of the plurality of X chromosome inactivated female human neural cells in the absence of the test compound. A "level of neurological functionality" means any measurable characteristic of the plurality of X chromosome inactivated female human neural cells that relates to the ability of the plurality of X chromosome inactivated female human neural cells to function as desired (e.g., function similarly or superior to a plurality of X chromosome inactivated female human neural cells that do not contain a mutated gene on the second of first X chromosome). In some embodiments, the level of neural functionality is determined by measuring in a plurality of X chromosome inactivated female human neuronal cells (e.g., neurons) the number of calcium transients and/or the percentage of X chromosome inactivated female human neuronal cells (e.g., neurons) that exhibit calcium transients as compared to a control. In some embodiments, the level of neural functionality is determined by measuring in a plurality of X chromosome inactivated female human neuronal cells (e.g., neurons) the frequency and/or amplitude of spontaneous excitatory and/or inhibitory postsynaptic currents as compared to a control.

The neurological disorder may be an autism spectrum disorder (e.g., autism or Rett syndrome), Alzheimer's disease, Parkinson's disease, Charcot-Marie-Tooth disease, Myasthenia Gravis, multiple sclerosis, chronic demyelinating polyneuropathy and the like. As used herein, "autism spectrum disorder" refers to a disease or disorder that is characterized by varying degrees of (1) deficits in social interaction, (2) deficits in verbal and nonverbal communication, and (3) repetitive behaviors or interests. Disorders of the autism spectrum include autism, Asperger's syndrome, Rett syndrome, Childhood Disintegrative Disorder, and Pervasive Developmental Disorder Not Otherwise Specified (PDD-NOS). In some embodiments, the neurological disorder is autism spectrum disorder. In some embodiments, the neurological disorder is autism. In some embodiments, the neurological disorder is Rett syndrome.

Methods of Determining Whether a Subject has a Neurological Disorder

In another aspect, a method of determining whether a human subject has a neurological disorder is provided. The method includes taking a somatic cell (e.g., a fibroblast cell, keratinocyte cell, or cell derived from tooth tissue as described above) from the human subject (e.g., a human female subject), generating an induced pluripotent stem cell from the somatic cell, and differentiating the induced pluripotent stem cell into a human neural cell (e.g., an X chromosome inactivated female human neural cell). The level of neurological functionality of the human neural cell is determined. The level of neural functionality of the human neural cell is compared to a control, thereby determining whether the subject has a neurological disorder. In some embodiments, the level of neural functionality is determined by measuring in the X human neural cell (e.g., an X chromosome inactivated female human neural cell) the number of calcium transients and/or the percentage of X chromosome inactivated female human neuronal cells (e.g., neurons) that exhibit calcium transients as compared to a control. In some embodiments, the level of neural functionality is determined by measuring in the X human neural cell (e.g., an X chromosome inactivated female human neural cell) the frequency and/or amplitude of spontaneous excitatory and/or inhibitory postsynaptic currents as compared to a control. The neurological disorder may be an autism spectrum disorder (e.g., autism or Rett syndrome), Alzheimer's disease, Parkinson's disease, Charcot-Marie-Tooth disease, Myasthenia Gravis, multiple sclerosis, chronic demyelinating polyneuropathy and the like. In some embodiments, the neurological disorder is autism spectrum disorder. In some embodiments, the neurological disorder is autism. In some embodiments, the neurological disorder is Rett syndrome. Induced pluripotent stem cells may be generated and differentiated into a human neural cell according to any method described herein or known in the art.

In some embodiments, the human neural cell is an X chromosome inactivated female human neural cell. In some embodiments, the X chromosome inactivated female human neural cell is a human neural progenitor cell or a human neuronal cell. In some embodiments, the X chromosome inactivated female human neural cell includes a mutated X chromosome linked gene. In some embodiments, the mutated X chromosome linked gene is capable of causing a neurological disorder when found in a human. In some embodiments, the mutated X chromosome linked gene is capable of causing an autism spectrum disorder (e.g., autism or Rett syndrome). In some embodiments, the mutated X chromosome linked gene is a mutated X-linked gene encoding MeCP2.

In some embodiments, the method includes determining the level of functionality of a plurality of human neural cells. In some embodiments, the method includes determining the level of functionality of a plurality of X chromosome inactivated female human neural cells. Each of the X chromosome inactivated female human neural cells includes a first X chromosome and a second X chromosome. The second X chromosome includes a mutated gene, where a portion of the plurality of X chromosome inactivated female human neural cells include an inactive first X chromosome and an active second X chromosome and another portion of the plurality of X chromosome inactivated female human neural cells include an active first X chromosome and an inactive second X chromosome. In some embodiments, the plurality of X chromosome inactivated female human neural cells are female human neural progenitor cells. In some embodiments, the plurality of X chromosome inactivated female human neural cells are female human neuronal cells. In some embodiments, at least a portion of the plurality of X chromosome inactivated female human neural cells are operably linked to form a neural network (i.e., a collection of neural cells in which at least some of the neural cells interact neurologically). In some embodiments, the mutated gene is capable of causing a neurological disorder when found in a human. In some embodiments, the mutated X chromosome linked gene is capable of causing an autism spectrum disorder (e.g., autism or Rett syndrome). In some embodiments, the mutated X chromosome linked gene is a mutated X-linked gene encoding MeCP2.

III. Examples

Autism and autism spectrum disorders (ASD) are heritable complex neurodevelopmental diseases in which different combinations of genetic mutations may contribute to the phenotype in different individuals. Herein is provided a cellular approach to study ASD. Using Rett syndrome (RTT) as an ASD genetic model, we developed an in vitro system by deriving induced pluripotent stem cells (iPSCs) from a RTT patient's fibroblast. Most RTT patients have mutations in the X-linked gene encoding the methyl-CpG binding protein 2 (MeCP2). RTT patients' iPSCs are pluripotent in culture and able to generate proliferating neural progenitor cells and functional postmitotic neurons while displaying X-inactivation. Although we found no differences in neural progenitor cell replication, glutamatergic neurons derived from RTT iPSCs had significantly fewer synapses compared to control neurons. Moreover, we characterized significant neuronal morphological changes that may contribute to an altered network dynamics in the RTT neuronal population. Thus, a human in vitro model of RTT has been generated from iPSCs from fibroblasts of a RTT patient and a control individual. The generated iPSCs-RTT surprisingly retained the capacity to generate proliferating neural progenitor cells and neurons that underwent X-inactivation. A reduced number of dendritic spines and synapses were observed in glutamatergic neurons. Moreover, using calcium imaging, an altered frequency of intracellular $Ca^{2+}$ spikes were detected in RTT-derived neuronal networks, revealing earlier markers for RTT pathology. Together, these results allow, inter alia, modeling and chemical screening of RTT and other ASD in a relevant cellular system. The model provides a reproducible assay to reveal and understand the common molecular mechanisms present in ASDs and is a promising human cellular tool for in vitro drug screening aimed at reverting neuronal phenotypes.

Cell Culture and Retrovirus Infection.

Female RTT and control fibroblasts were generated from explants of dermal biopsies following informed consent under protocols approved by the University of California San Diego. The Syn::EGFP or DsRed reporter vector was obtained by cloning the Synapsin-1 promoter in a lentivirus backbone. The shRNA against a target sequence on the human MeCP2 gene was cloned in the LentiLox3.7 lentivirus vector. Retrovirus vectors containing the Oct4, c-Myc, Klf4 and Sox2 human cDNAs from Yamanaka's group (Takahashi et al., 2007, Id.) were obtained from Addgene. Two days after infection, fibroblasts were plated on mitotically inactivated mouse embryonic fibroblasts (Chemicon) with hESC medium. After 2 weeks, iPSC colonies were directly transferred to feeder-free conditions on matrigel-coated dishes (BD) using mTeSRTM1 (StemCell Technologies), and passed manually. To obtain neural progenitor cells, embryoid bodies (EBs) were formed by mechanical dissociation of cell clusters and plating onto low-adherence dishes in hESC medium without FGF2 for 5-7 days. After that, EBs were plated onto poly-ornithine/laminin (Sigma)-coated dishes in DMEM/F12 (Invitrogen) plus N2. Rosettes were visible to collect after 7 days. Rosettes were then dissociated with accutase (Chemicon) and plated again onto coated dishes with NPC media (DMEM/F12/0.5×N2; 0.5× B27 and FGF2). Homogenous populations of NPCs were achieved after 1-2 passages with accutase in the same condition. To obtain mature neurons, floating EBs were treated with 1 μM of retinoic acid for 3 more weeks (total time of differentiation 4 weeks). Mature EBs were then dissociated with Papain and DNase (Worthington) for 1 hr at 37° C. and plated in poly-ornithine/laminin-coated dishes in NPC media without FGF2. For the rescue experiments, 10 μg/mL of IGF1 (Peprotech) or Gentamicin (Invitrogen; at 100 or 400 μg/mL) was added to neuronal cultures for 1 week. Protocols were previously approved by the University of California San Diego and Salk Institute Institutional Review Board and the Embryonic Stem Cell Research Oversight Committee.

Immunocytochemistry and Synapse Quantification.

Cells were briefly fixed in 4% paraformaldehyde and then permeabilized with 0.5% Triton-X100 in PBS. Cells were then blocked in PBS containing 0.5% Triton-X100 and 5% donkey serum for 1 hour before incubation with primary antibody overnight at 4° C. After 3 washes with PBS, cells were incubated with secondary antibodies (Jackson ImmunoResearch) for 1 hour at room temperature. Fluorescent signals were detected using a Zeiss inverted microscope and images were processed with Photoshop CS3 (Adobe Systems). Primary antibodies used in this study are described herein. Cell soma size was measure in bright field using ImageJ software after identification of neurons using the Syn::EGFP. The morphologies of neuronal dendrites and spines were studied from an individual projection of z-stacks optical sections and scanned at 0.5-μm increments that correlated with the resolution valued at z-plane. Each optical section was the result of 3 scans at 500 lps followed by Kalman filtering. For synapse quantification, images were taken by a z-step of 1 μm using Biorad radiance 2100 confocal microscope. Synapse quantification was done blinded to genotype. Only VGLUT1 puncta along Map2-positive processes were counted. Statistical significances were tested using Two-way ANOVA test and Bonferroni post-test.

Cell Cycle Analysis.

One million NPCs were fixed in 70% EtOH for at least 2 hours at 4° C. After PBS washing, cells were stained with 1 mL of propidium iodide (PI) solution (50 μg/mL PI in 3.8 Mm sodium citrate) and treated with 20 μL/mL of RNAseA. Cells were analyzed by fluorescence-activated cell sorting (FACS) on a Becton-Dickinson LSRI and cell cycle gating was examined using FLOWJO—Flow Cytometry Analysis Software.

RNA Extraction and RT-PCR.

Total cellular RNA was extracted from ~$5 \times 10^6$ cells using the RNeasy Protect Mini kit (Qiagen, Valencia, Calif.), according to the manufacturer's instructions, and reverse transcribed using the SuperScript III First-Strand Synthesis System RT-PCR from Invitrogen. The cDNA was amplified by PCR using Accuprime Taq DNA polymerase system (Invitrogen). The primer sequences were: hPAX6-F: 5' acccattatccagatgtgtttgcccgag (SEQ ID NO:11) and hPAX6-R 5' atggtgaagagggcataggeggcag (SEQ ID NO:12); hMSX1-F: 5' cgagaggaccccgtggatgcagag (SEQ ID NO:13) and hMSX1-R: 5' ggcggccatcttcagatctccag (SEQ ID NO:14); hKRT-18-F: tctgtggagaacgacatcca (SEQ ID NO:15) and KRT-18-R: 5' ctgtacgtctcagctctgtga (SEQ ID NO:16); hAFP-F: 5' aaaagcccactccagcatc (SEQ ID NO:17) and hAFP-R: 5' cagacaatccagcacatctc (SEQ ID NO:18); hGAPDH-Fw: 5' accacagtccatgccatcac (SEQ ID NO:19), hGAPDH-Rv: 5' tccaccaccctgttgctgta (SEQ ID NO:20). PCR products were separated by electrophoresis on a 2% agarose gel, stained with ethidium bromide and visualized by UV illumination.

Teratoma Formation in Nude Mice.

Around $1-3 \times 10^6$ fibroblasts or iPSCs were injected subcutaneously into the dorsal flanks of nude mice (CByJ.Cg-Foxn1nu/J) anesthetized with isoflurane. Five to six weeks after injection, teratomas were dissected, fixed overnight in 10% buffered formalin phosphate and embedded in paraffin. Sections were stained with hematoxylin and eosin for further analysis. Control mice injected with RTT fibroblasts failed to form teratomas. Protocols were approved by the University of California San Diego Institutional Animal Care and Use Committee.

Karyotyping and DNA Fingerprinting.

Standard G-banding chromosome and DNA fingerprinting analysis was performed by Cell Line Genetics (Madison, Wis.).

DNA and RNA FISH.

Xist RNA exon 6 probes (GenBank U80460: 75081-78658) were transcribed by using T7 RNA polymerase (Roche) with AlexaFluor 488-5-UTP. X chromosome probe and Xist slide hybridization were performed by Molecular Diagnostic Services, Inc. (San Diego, Calif.).

Protein Isolation and Western Blot Analysis.

Cells were isolated, suspended in 1×RIPA lyses buffer (Upstate) supplemented with 1% protease inhibitor cocktail (Sigma), triturated and centrifuged at 10,000×g for 10 minutes at 4° C. Twenty micrograms of total protein was separated on 12% SDS-polyacrylamide gel, transferred to a nitrocellulose membrane and probed with a primary antibody against MeCP2 (1:5,000; Diagenode), followed by horseradish-peroxidase-conjugated secondary antibody (1:5,000; Promega), and then visualized using ECL chemiluminescence (Amersham). As a control, membranes were stripped and re-probed for β-actin (1:10,000; Ambion) or α-tubulin (1:5,000, Ambion). For semi-quantitative analysis, MeCP2 signal intensity was analyzed and corrected with respect to β-actin.

Microarray Analysis.

The Affymetrix Power Tools (APT) suite of programs and Affymetrix Human Gene 1.0 ST Arrays library files and annotation were obtained from the Affymetrix website. Gene-level signal estimates were derived from the CEL files by RMA-sketch normalization as a method in the apt-probeset-summarize program. Hierarchical clustering of the full dataset by probeset values was performed by complete linkage using Euclidean distance as a similarity metric in Matlab.

Electrophysiology.

Whole-cell patch clamp recordings were performed from cells co-cultured with astrocytes after 6 weeks of differentiation. The bath was constantly perfused with fresh HEPES-buffered saline as described herein. The recording micropipettes (tip resistance 3-6 MΩ) were filled with internal solution described in the Supplemental materials. Recordings were made using Axopatch 200B amplifier (Axon Instruments). Signals were filtered at 2 kHz and sampled at 5 kHz. The whole-cell capacitance was fully compensated. The series resistance was uncompensated but monitored during the experiment by the amplitude of the capacitive current in response to a 10-mV pulse. All recordings were performed at room temperature and chemicals were purchased from Sigma. Frequency and amplitude of spontaneous postsynaptic currents were measured with the Mini Analysis Program software (Synaptosoft, Leonia, N.J.). Statistical comparisons of WT and RTT groups were made using the non-parametric Kolmogorov-Smirnov two-tailed test, with a significance criterion of p=0.05. EPSCs were blocked by CNQX or DNQX (10-20 μM) and IPSPs were inhibited by bicuculine (20 μM).

Calcium Imaging.

Neuronal networks derived from human iPSCs were previously infected with the lentiviral vector carrying the Syn::DsRed reporter construct. Cell cultures were washed twice with sterile Krebs HepesHEPES Buffer (KHB) (10 mM HEPES, 4.2 mM NaHCO3, 10 mM dextrose, 1.18 mM MgSO4.2H2O, 1.18 mM KH2PO4, 4.69 mM KCl, 118 mM NaCl, 1.29 mM CaCl2; pH 7.3) and incubated with 0.2-0.5 μM Fluo-4AM (Molecular Probes/Invitrogen, Carlsbad, Calif.) in KHB for 40 minutes at room temperature. Excess dye was removed by washing twice with KHB and an additional 20-minute minutes incubation was done to equilibrate intracellular dye concentration and allow de-esterification. Time-lapse image sequences (200×100× magnification) of 5000 frames were acquired at 28 Hz with a region of 336×256 pixels, using a Hamamatsu ORCA-ER digital camera (Hamamatsu Photonics K.K., Hamamatsu City, Japan) with a 488 mm (FITC) filter on an Olympus IX81 inverted fluorescence confocal microscope (Olympus Optical, Tokyo, Japan). Images were acquired with MetaMorph 7.17 (MDS Analytical Technologies, Sunnyvale, Calif.). Images were subsequently processed in using ImageJ (National Instituted of Health, Washington D.C.) and Matlab 7.2 (Mathworks, Natick, Mass.).

Quantification of $Ca^{2+}$ Transients.

ImageJ, an NIH funded open source, JAVA-based morphometric application, was used to allow manual selection of individual cells on the xy-plane of each movie using circles of 4 pixels (~5 μm) in diameter. Each cell was considered as an individual region of interest (ROIs) and the average fluorescence intensity was calculated for each ROI in each frame using Time Series Analyzer ImageJ plugin.

Quantitative signal analysis and processing were done in custom Matlab routines. The temporal fluorescence intensity signals indicative of intracellular $Ca^{2+}$ fluctuations were filtered with low pass Gaussian filter to reduce noise. Signals were presented as relative fluorescence changes ($\Delta F/F$) after background subtraction. A first-derivative filter was used to identify significant increases in calcium levels, i.e., >10 consecutive frames (~350 ms) with positive derivative values.

Results

Generation of RTT and Control iPSCs

Figure 1H:
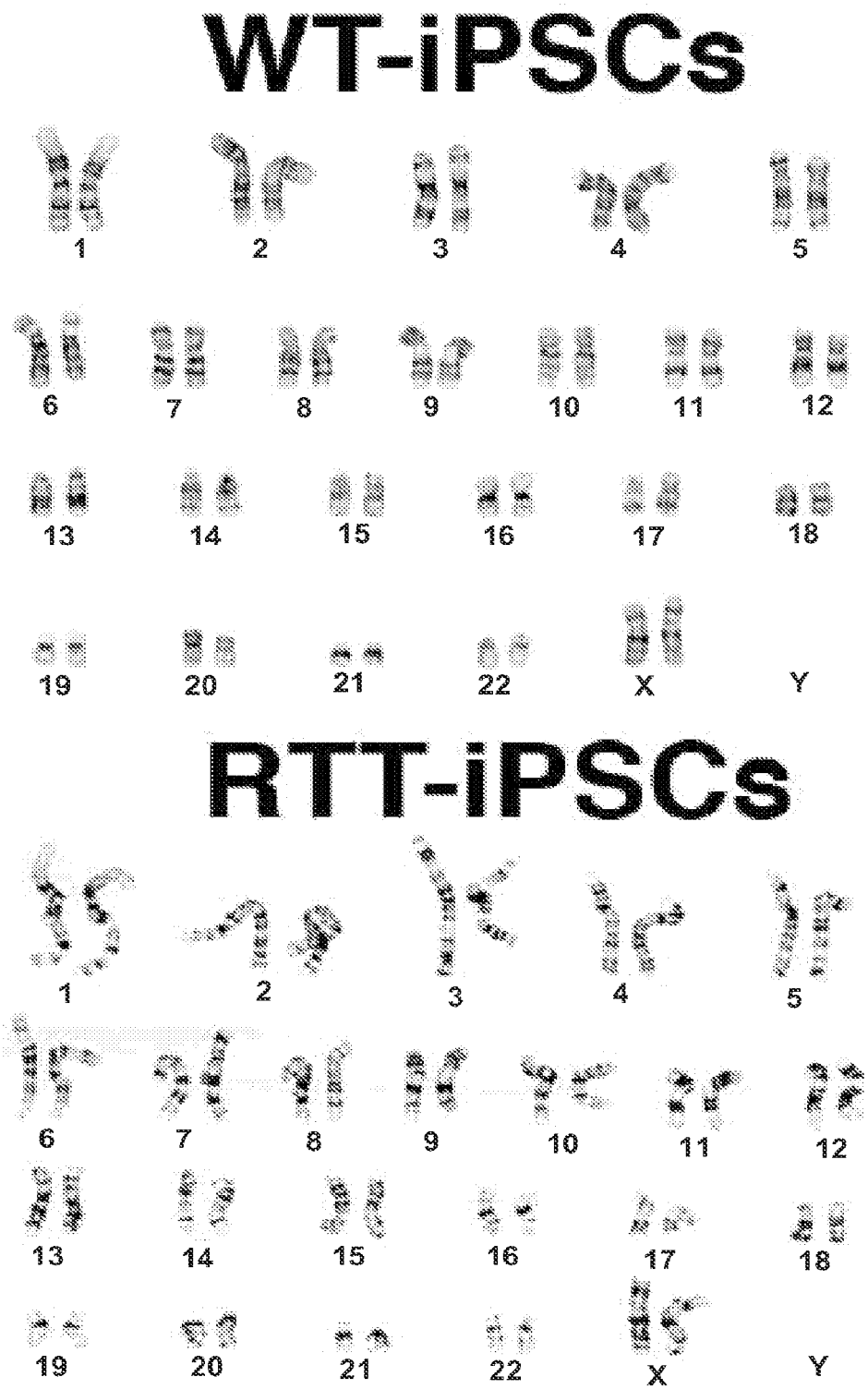
FIG. 1H: No karyotypic abnormalities were observed.
Figure 1B:
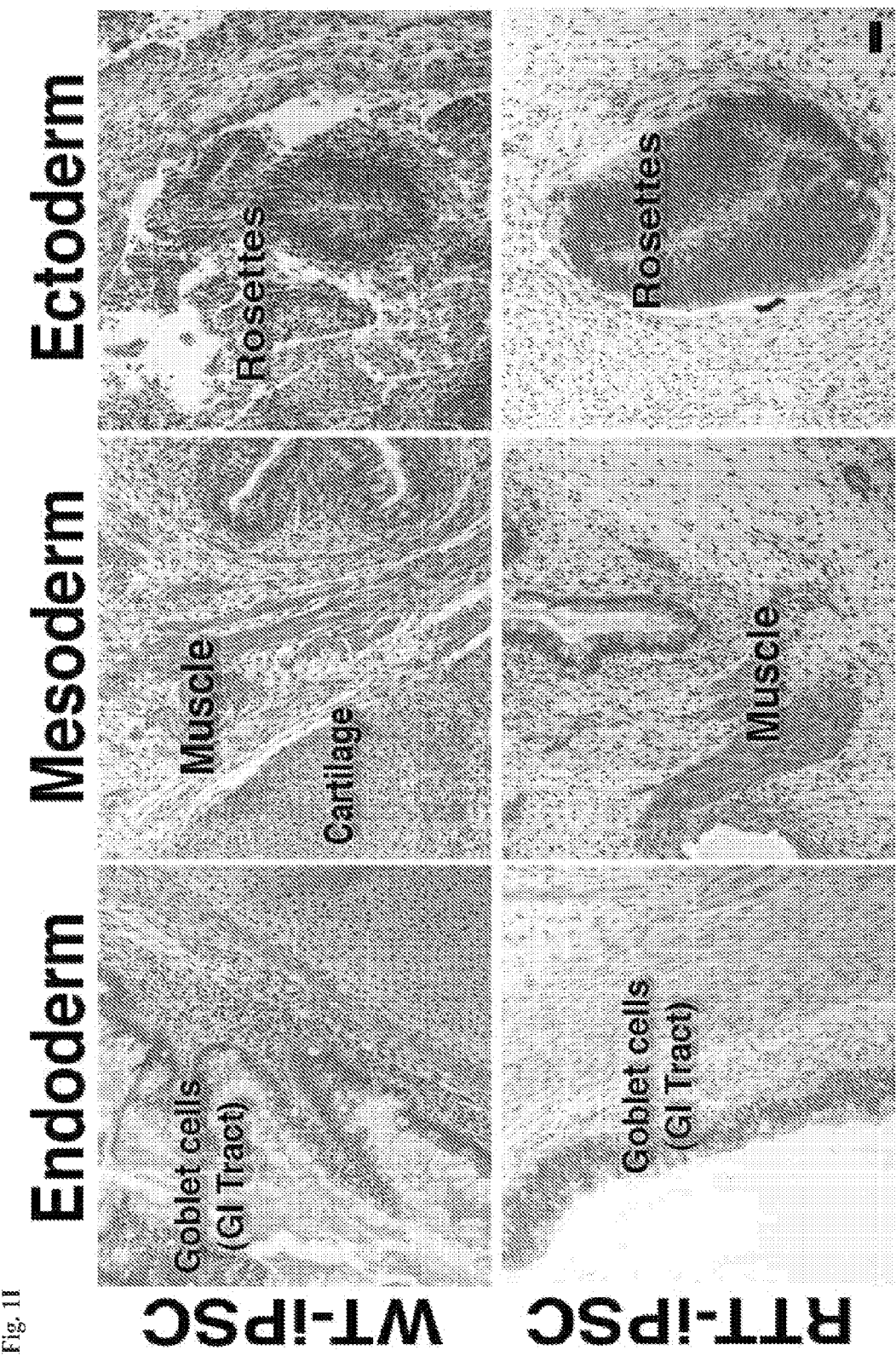
FIG. 1B: Morphology of human fibroblasts before retroviral infection.
Figure 7D:
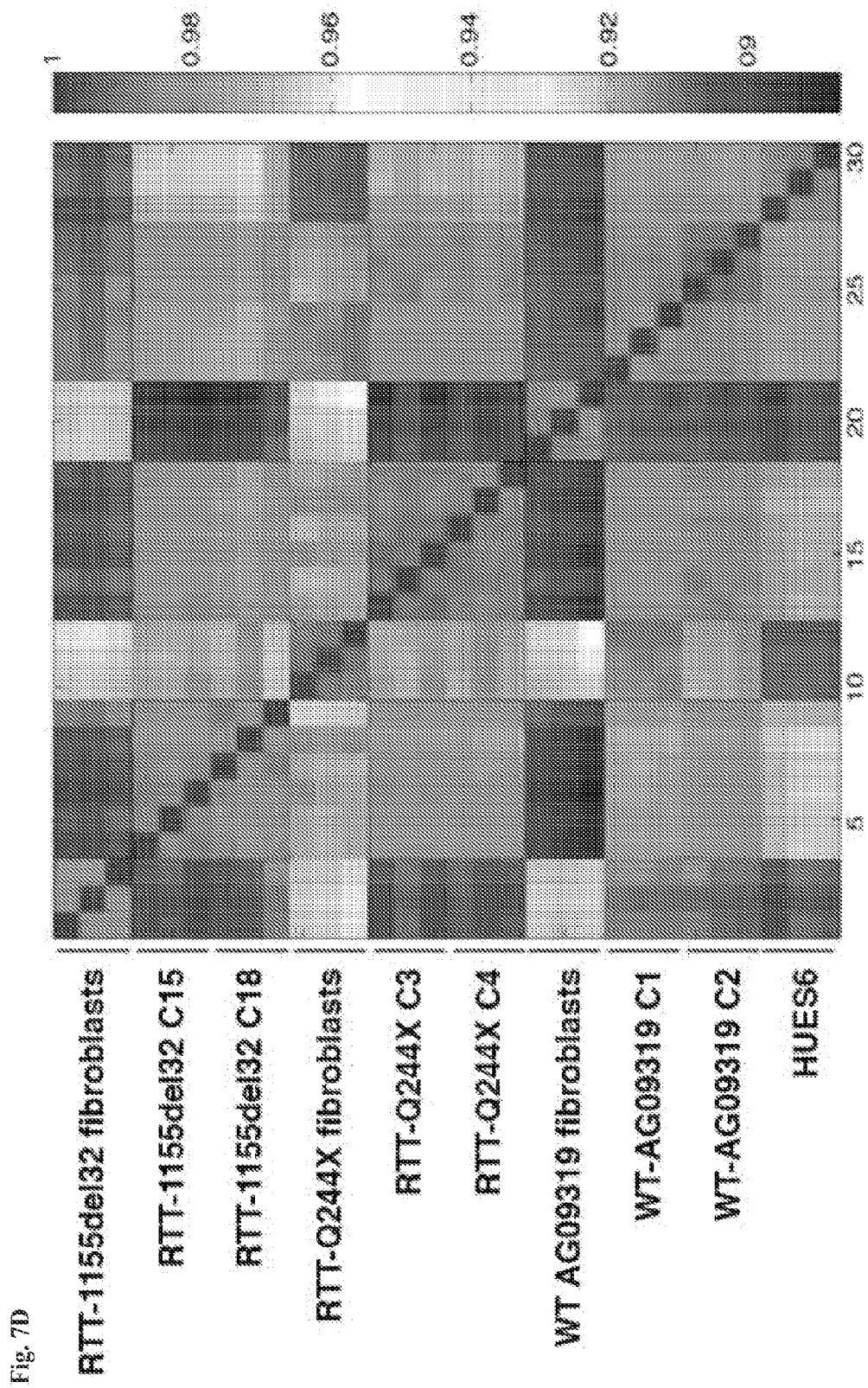
FIG. 7D: Hierarchical clustering and correlation coefficients of microarray profiles of triplicate WT Fibroblasts, RTT Fibroblasts, WT-iPSC clone 1, WT-iPSC clone 2, RTT-iPSC clones 15 and 18 (1155del32), RTT-iPSC clones 1 and 2 (Q244X) and the hESC line HUES6. Shade indicates the level of correlation (from 0 to 1), with bar reporting log 2 normalized expression values.
Figure 7F:
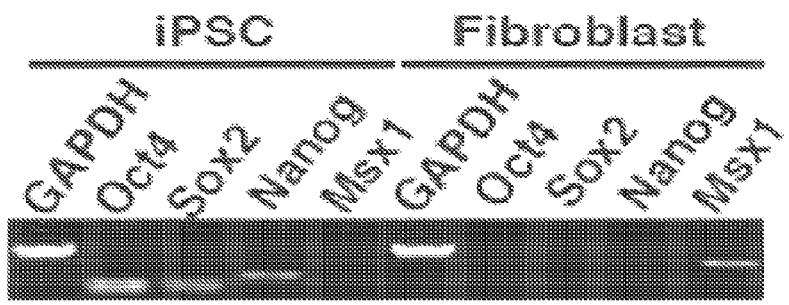
FIG. 7F: RT-PCR from reprogrammed iPSCs showed endogenous expressions of hESC-enriched genes (Oct4, Sox2 and Nanog) but not from a fibroblast-enriched gene (Msx1). Lanes in FIG. 7F in order (left to right): (iPSC) GAPDH; Oct4; Sox2; Nanog; Msx1; (Fibroblast) GAPDH; Oct4; Nanog; Msx1.

Non-affected control fibroblasts and cells carrying four distinct MeCP2 mutations (FIG. 1A and Table 1 following) isolated from clinically affected female patients with RTT symptoms were infected with retroviral reprogramming vectors (Sox2, Oct4, c-Myc and Klf4), as described elsewhere. See, e.g., Takahashi et al., 2007, Id. After 2 to 3 weeks, compact iPSC colonies emerged from a background of fibroblasts. See FIGS. 1B1C. Colonies were manually picked and transferred to matrigel, as known in the art. See FIGS. 1D-1E. We obtained at least 10 clones from each control (WT)-iPSC and RTT-iPSC that continuously expressed pluripotent markers such as Nanog, Lin28, Tra-1-81 and Sox2. See FIGS. 1F-1G and FIGS. 7A-7C. All iPSC clones used in this study maintained a normal karyotype. See FIG. 1H. Teratomas containing derivatives from all 3 embryonic germ layers confirmed that the iPSCs were able to differentiate in vivo. See FIG. 1I. PCR fingerprinting confirmed their derivation from respective fibroblasts. Next, we asked if the global molecular signatures of RTT-iPSC clones carrying the two distinct MeCP2 mutations (1155del32 and Q244X) and WT-iPSC clones (from AG09319) resembled those of available hESC lines (HUES6). Gene expression profiles measured using human genome Affymetrix Gene Chip arrays were grouped by hierarchical clustering, and correlation coefficients were computed for all pair-wise comparisons (GEO accession number GSE21037). We observed that the WT-iPSC and RTT-iPSC clones were almost indistinguishable. The results clearly revealed that the iPSC and hESC lines were more similar to each other than to the respective original fibroblasts. See FIG. 7D. These findings, combined with manual inspection of the gene expression of known pluripotent- and fibroblast-related genes (FIGS. 7E-7F), indicated that the reprogramming was successful. In Tables 2.1 and 2.2 following, there is presented a summary of iPSC subjects and clones utilized for the experiments described herein.

TABLE 1

MeCP2 mutations, phenotype description and respective cell lines.

| Cell line name | iPSC code | Gender | MeCP2 Mutation | Nucleotide change | Individual phenotype |
|---|---|---|---|---|---|
| GM11270* | R306C | Female | missense | 916C > T | Clinically affected; classical symptoms; normal lysosomal enzymes; 46, XX in PBL; donor carries missense mutation, 916C > T, in the gene encoding methyl-CpG binding protein 2 (MECP2). |
| GM11272* | 1155del32 | Female | frameshift | 1155del32 | Clinically affected; classical symptoms; normal lysosomal enzymes; 46, XX in PBL; donor subject carries a frameshift mutation, 1155del32, in the gene encoding methyl-CpG binding protein 2 (MECP2). |
| GM16548* | Q244X | Female | nonsense | 730C > T | Clinically affected; abnormal sleep patterns; ambulatory; breath holding; constipation; decelerating head circumference; loss of purposeful hand use; nonverbal; poor hand and feet circulation; repetitive hand motions; self injurious behavior; small feet; teeth grinding; tremors; donor subject is heterozygous for a 730C > T transition in the MECP2 gene resulting in a stop codon. |
| GM17880* | T158M | Female | missense | 473C > T | Growth and developmental delay; can walk only with assistance; nonverbal; no hand use; constant repetitive hand motions; no seizures, but significantly abnormal EEG; teeth grinding; some sleep difficulties; eating problems with minor reflux; breath holding and hyperventilation; small feet; some tremor; this culture had a lifespan of 56 population doublings (PDLs); the donor subjects carried a 473C > T transition, resulting in the substitution of threonine 158 by methionine |
| AG09319* | AG09319 | Female | WT | — | Healthy individual. The karyotype is 46, XX; normal diploid female. |
| CRL2529** | CRL2529 | Male | WT | — | Healthy individual. The karyotype is 46, XY; natrual diploid male. |
| WT-126*** | 126 | Male | WT | — | Healthy individual. The karyotype is 46, XY; normal diploid male. |
| WT-33*** | 33 | Female | WT | — | Healthy individual. The karyotype is 46, XX; normal diploid female. |
| WT-ARDC40*** | ARDC40 | Male | WT | — | Healthy individual. The karyotype is 46, XY; normal diploid male. |

*From Coriell.
**From ATCC
***From biopsies of healthy individuals.

TABLE 2.1

Summary of the iPSC subjects and clones utilized for each experiment.
Numbers represent experimental replications for each individual clone.
The clones utilized in neuronal differentiation experiments
were determined by availability at the end time-point.

| | SUBJECTS | | | | | |
|---|---|---|---|---|---|---|
| | ADRC40 | AG09319 | | CRL2529 | WT-33 | |
| Experiments/clones | C1 | C1 | C2 | C1 | C1 | C7 |
| Pluripotency assays | 2 | 2 | 2 | 2 | 2 | 2 |
| Gene expression | | 3 | 3 | | | |
| Map2 Labeling | 3 | 3 | | | 3 | |
| Syn::DsRed labeling | | 3 | | | 3 | |
| GABA labeling | | 3 | | | 3 | |
| H3K27me3 labeling | | 3 | | | 3 | |
| Xist FISH | | | | | 2 | |
| Androgen receptor | | | | | 2 | |
| Cell cycle | | 3 | | 3 | | |
| VGLUT puncta | 3 | 3 | | | 3 | |
| Soma size | 2 | | 2 | | | 2 |
| Spine Density | | | 3 | | | |
| Calcium Transients | | | | | 3 | |
| Electrophysiology | | | | | 3 | |

TABLE 2.2

Continuation of Table 2.1.

| | SUBJECTS | | | | | | | | |
|---|---|---|---|---|---|---|---|---|---|
| | WT-126 | | | 1155del32 clones | | Q244X | | T158M | R306C |
| Experiments | C5 | C8 | C13 | C15 | C18 | C3 | C4 | C3 | C1 |
| Pluripotency assays | 2 | 2 | 2 | 2 | 2 | 2 | 2 | 2 | 2 |
| Gene expression | | | | 3 | 3 | 3 | 3 | | |
| Map2 Labeling | 3 | 3 | | 3 | 3 | 3 | 3 | 3 | |
| Syn::DsRed labeling | | 3 | | 3 | 3 | 3 | | | |
| GABA labeling | | 3 | | 3 | | 3 | | 3 | |
| H3K27me3 labeling | | | | 3 | 3 | 3 | | | |
| Xist FISH | | | | 2 | 2 | 2 | | | |
| Androgen receptor | | | | 2 | | 2 | | | 2 |
| Cell cycle | | | 3 | 3 | 3 | | | 3 | |
| VGLUT puncta | 3 | 3 | | 3 | 3 | | 3 | 3 | |
| Soma size | | 2 | 2 | 2 | 2 | 2 | 2 | 2 | |
| Spine Density | | 3 | | | 3 | 3 | | | |
| Calcium Transients | | 3 | | 3 | 3 | | | | |
| Electrophysiology | | 4 | | 4 | 4 | | | | |

Neural Induction of iPSCs

Figures 2B, 2C:
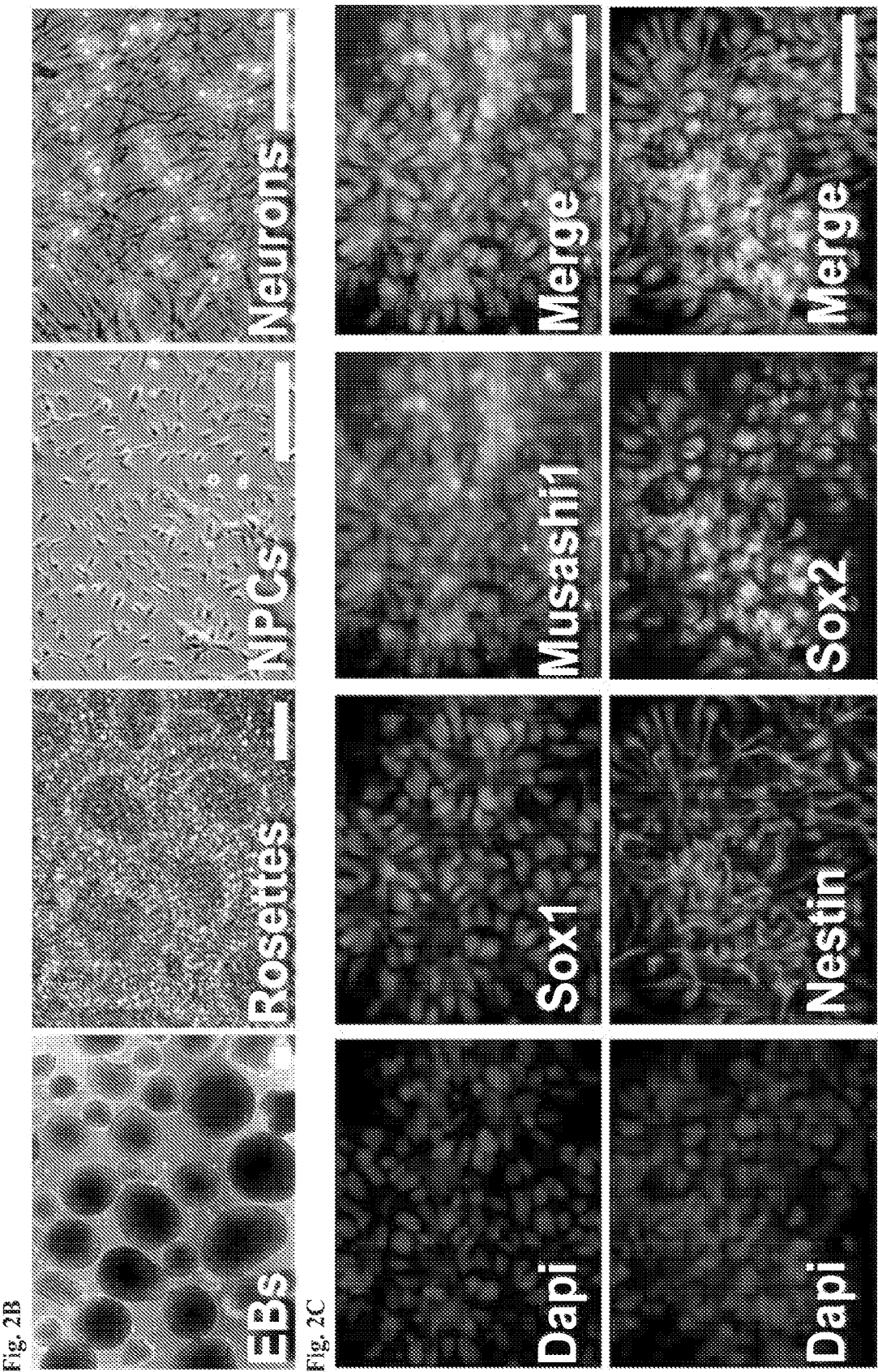
FIG. 2B: Representative images depicting morphological changes during neuronal differentiation. Bar=100 μm.
FIG. 2C: NPCs are positive for neural precursor markers: Sox1, Sox2, Musashi1 and Nestin. Bar=50 μm.
Figure 2D:
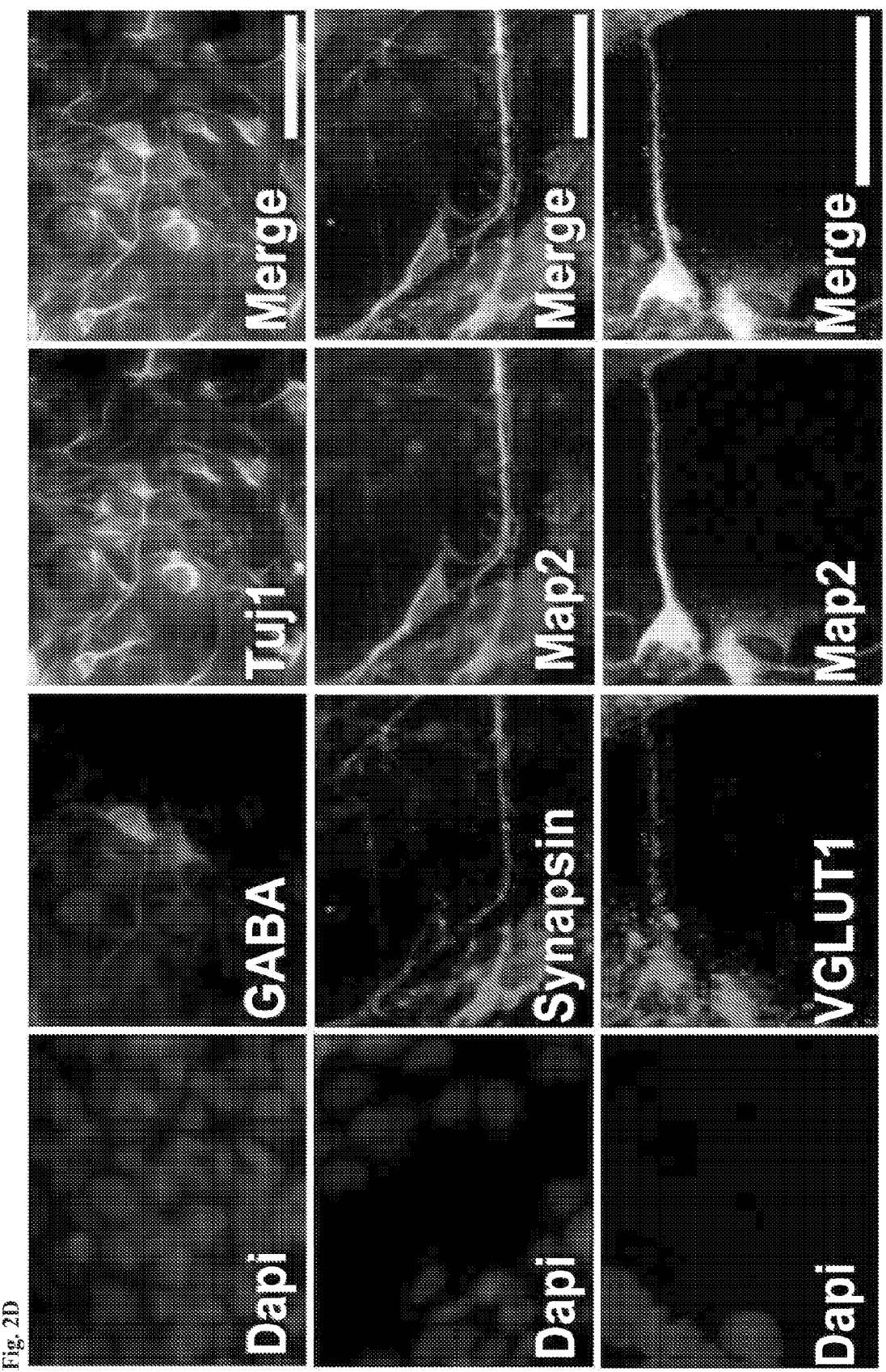
FIG. 2D: Representative images of cells after neuronal differentiation. iPSC-derived neurons express mature neuronal markers: GABA, Map2 and Synapsin. Bar=20 μm. Similar numbers of Map2-positive and Syn::DsRed-positive (FIG. 2E) as well as GABA-positive (FIG. 2F) neurons from WT and RTT cultures. Data shown as mean±s.e.m. See also FIG. 8.
Figure 2E:
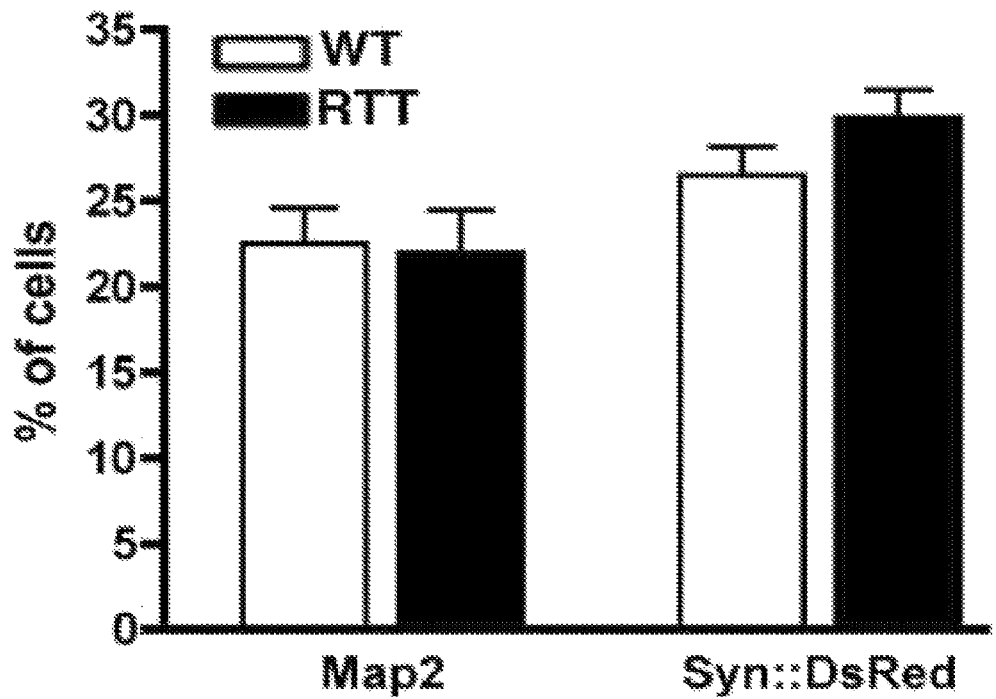
FIG. 2. Neural differentiation of iPSCs.
FIG. 2A: Schematic view of a neural differentiation protocol described herein.
Figure 2F:
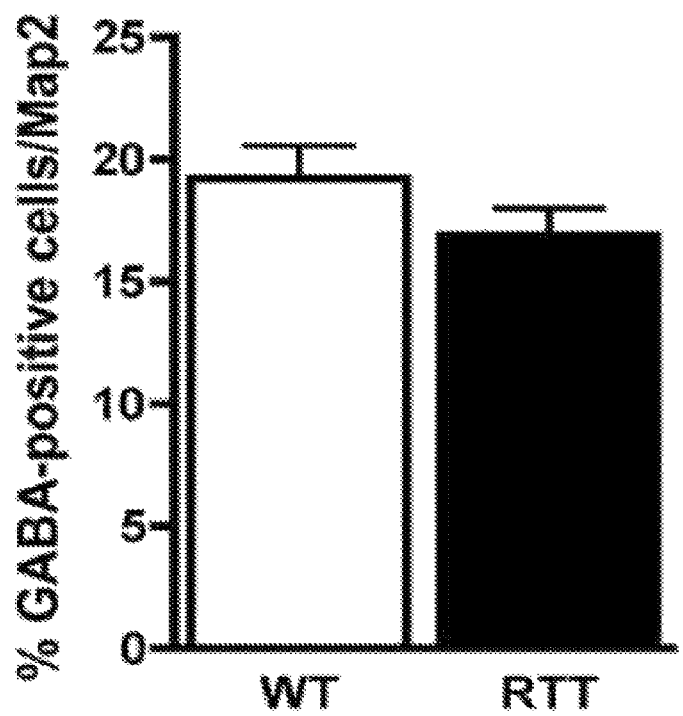
Figure 8A:
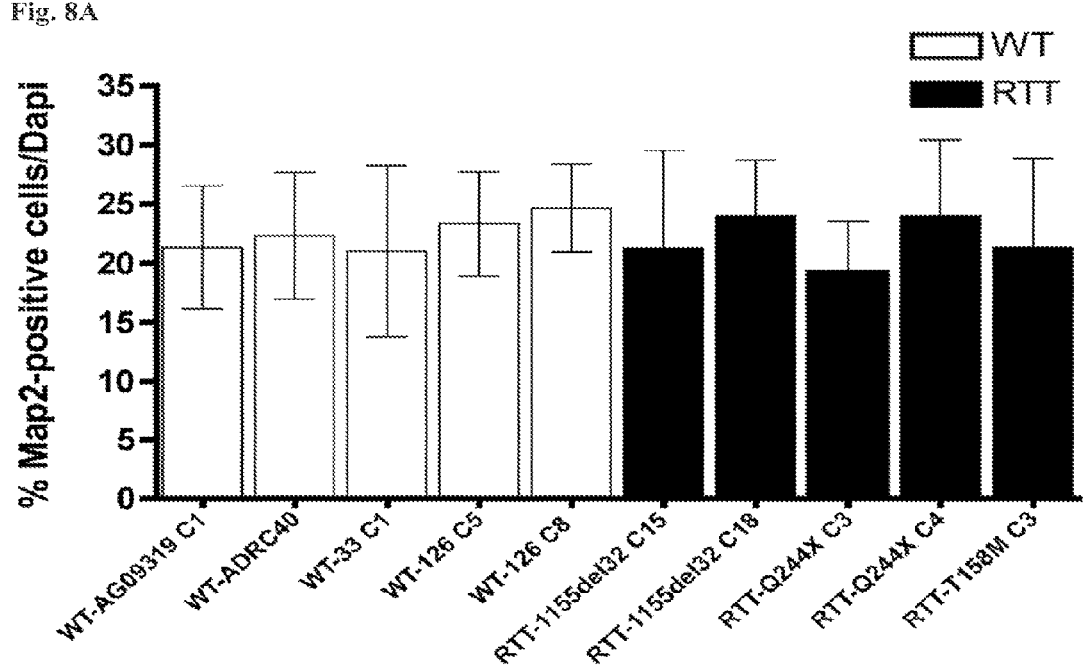
FIG. 8A: Neurons were stained with the Map2 neuronal marker. Order of X-axis entries for histogram
Figure 8B:
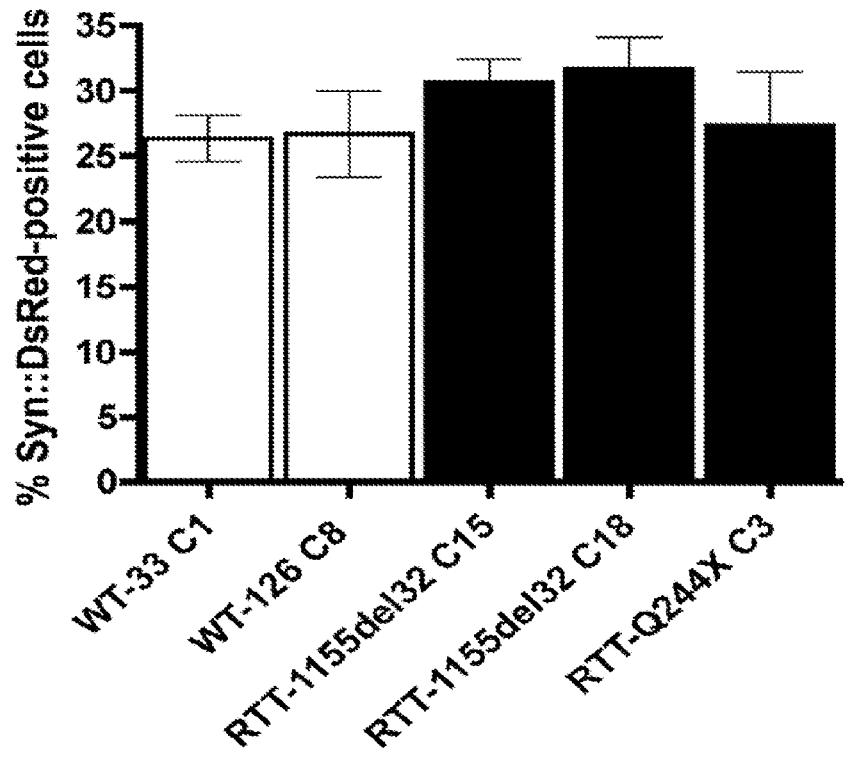
FIG. 8B: Neurons were infected with a lentiviral vector expressing the DsRed reporter under the control of the Synapsin promoter region. Order of X-axis entires for histogram
Figure 8C:
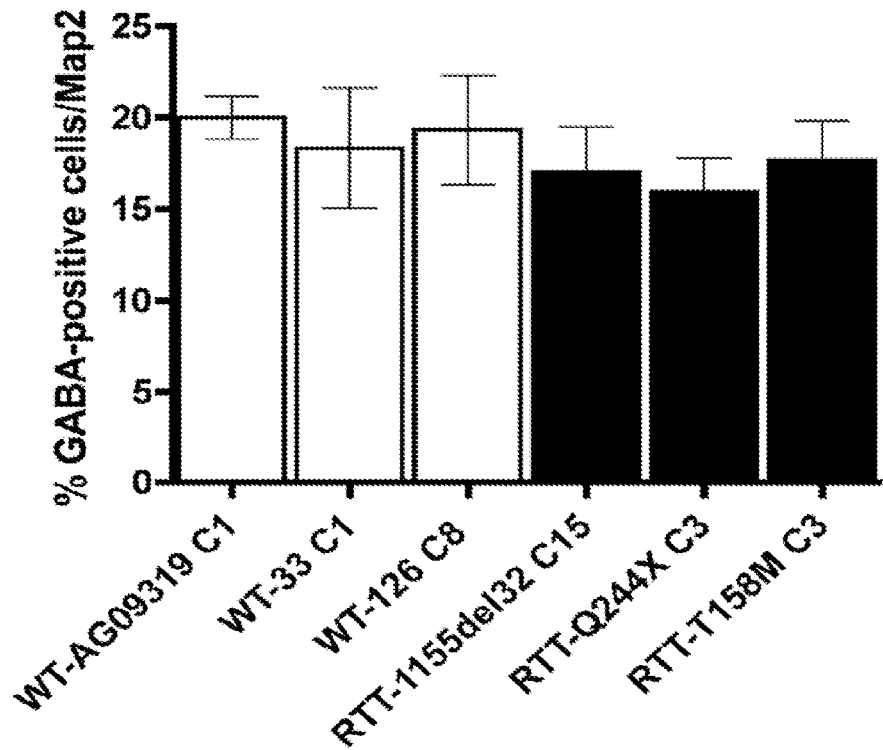
FIG. 8C: Inhibitory neurons were revealed in the cultures after staining with anti-GABA antibody. Each bar represents 3 independent experiments for each individual clone. Order of X-axis entries for histogram

A protocol for neuronal differentiation is outlined in FIG. 2A. Neural differentiation was initiated by plating embryoid bodies (EBs). After a week, EB-derived rosettes became apparent (FIG. 2B). Rosettes were then manually collected, dissociated and re-plated. The NPCs (neural precursor cells) derived from rosettes formed a homogeneous population after a couple of passages. NPCs were positive for early neural precursor markers, such as Nestin, Sox1-2 and Musashi1 (FIG. 2C). To obtain mature neurons, EBs in the presence of retinoic acid (RA) were dissociated and re-plated (FIG. 2B). At this stage, cells were positive for Tuj1 (β-III-Tubulin) and Map2 (Microtubule-associated protein 2). See FIG. 2D. Moreover, there was detected expression of the inhibitory and excitatory neurotransmitters GABA (γ-amino butyric acid) and VGLUT1 (vesicular glutamate transporter-1), respectively. Also observed were synapsin puncta outlining Map2-positive neurites. See FIG. 2D. A significant alteration in RTT neuronal survival was not detected when compared to controls, as measured by Map2 staining. See FIGS. 2E and 8A. In addition, infection with a lentivirus expressing the DsRed gene under the control of Synapsin promoter (Syn::DsRed) did not reveal any difference in neuronal survival between RTT and controls. See FIGS. 2E and 8B. Interestingly, the number of GABA-positive neurons was also not affected between RTT and controls. See FIGS. 2F and 8C.

X-Inactivation During Neuronal Differentiation of iPSCs-RTT

Figure 3B:
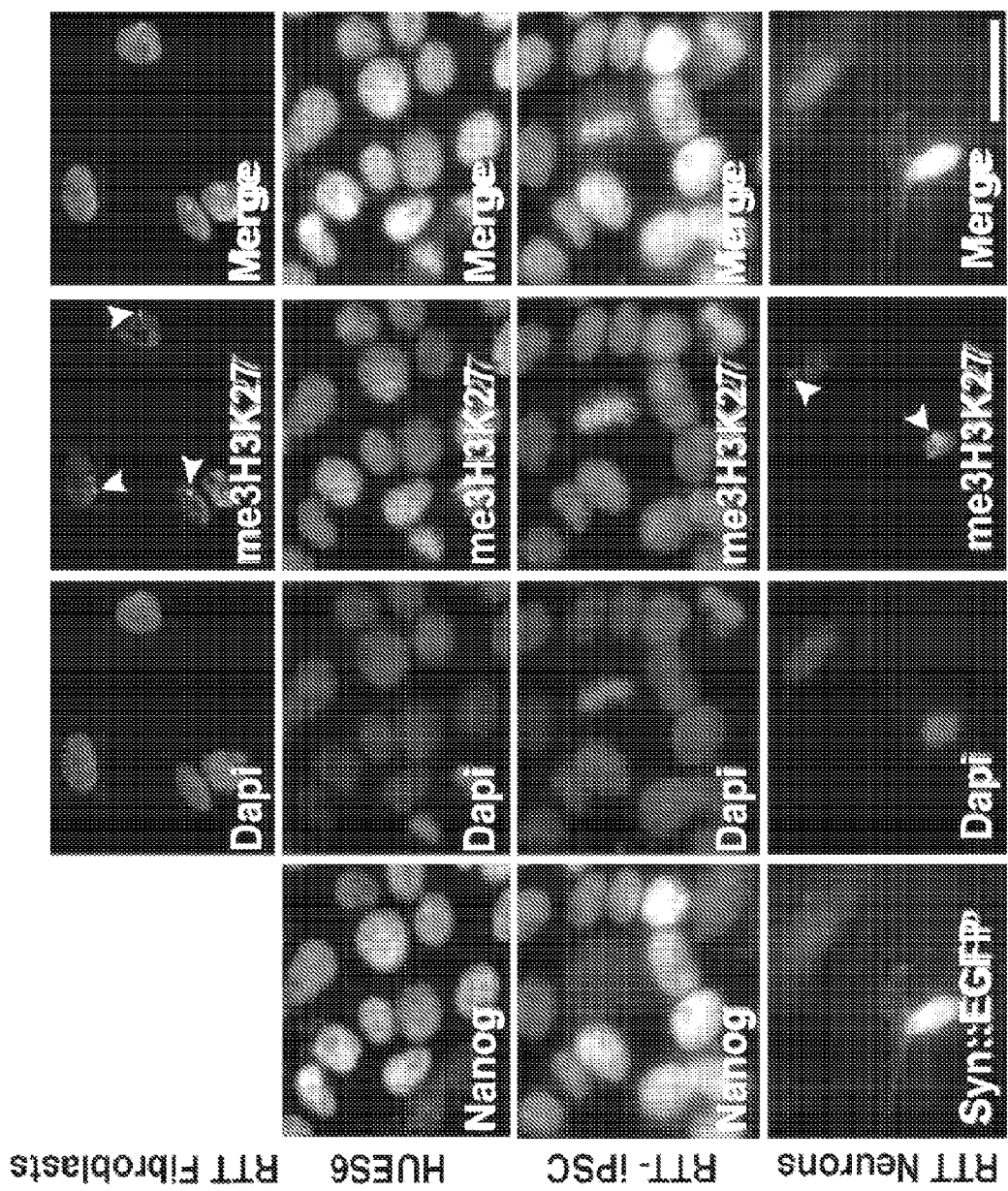
FIG. 3. RTT-iPSC clones undergo X-inactivation during differentiation.
FIG. 3A: Schematic representation of X-inactivation dynamics during reprogramming and further neural differentiation. RTT fibroblasts are mosaic for the MeCP2 WT gene expression. During reprogramming, X-inactivation is erased and iPSCs express both MeCP2 alleles. Upon neuronal differentiation, X-inactivation is re-established and the resultant cells are mosaic for MeCP2 WT gene expression. 3B: Immunofluorescence for me3H3K27 in fibroblasts, pluripotent cells (Nanog-positive) and after neuronal differentiation (Syn::EGFP-positive). Pluripotent cells (hESCs and iPSCs) show diffuse staining whereas differentiated cells (fibroblasts and neurons) exhibit prominent me3H3K27 nuclear foci (arrowheads). Cells were counterstained with Dapi. Bar=15 μm.
FIG. 3C: Quantification of cells as indicated with diffuse or foci me3H3K27 nuclear staining. Data shown as mean±s.e.m.
FIG. 3D: RNA FISH shows that Xist RNA domains are present in the original fibroblasts before reprogramming. iPSCs show no Xist expression. Neurons derived from normal and RTT iPSCs show clear Xist clouds, indicating transcriptional silencing of the X chromosome (arrows). Bar=5 μm.
FIG. 3E: Two DNA FISH signals are evident in the nuclei of iPSC-derived NPCs and neurons, revealing the presence of two X chromosomes. Bar=10 μm.
FIG. 3F: RTT-iPSCs (1155del32) expressed WT MeCP2 but derived neurons displayed mosaicism regarding WT (arrowhead) and mutant (arrow) MeCP2 forms. Bar=50 μm.
FIG. 3G: RTT-derived fibroblasts and neurons have reduced levels of WT MeCP2 protein by Western blot. See also FIG. 9.
Figure 3C:
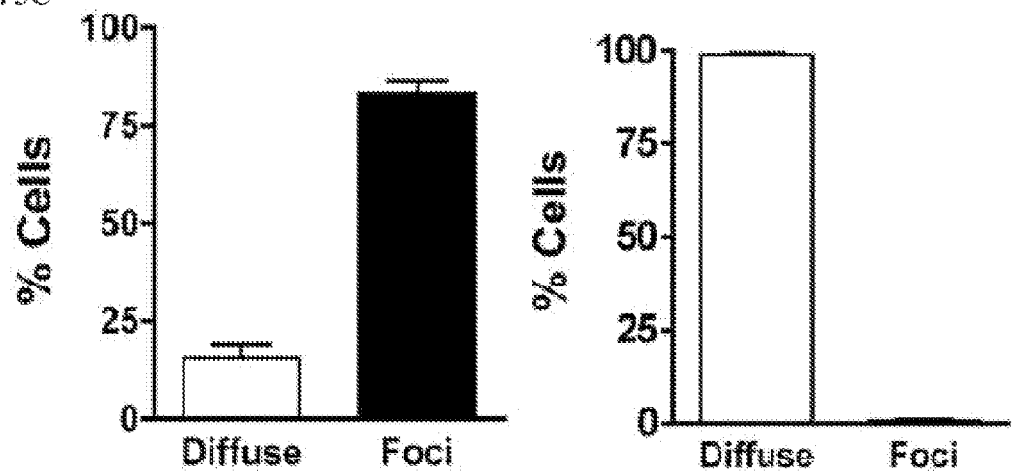
Figure 3C:
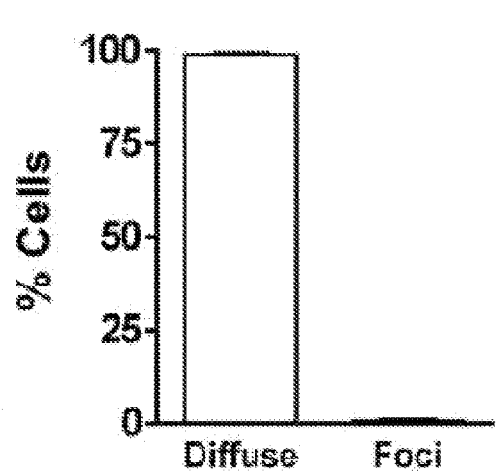
Figure 3C:
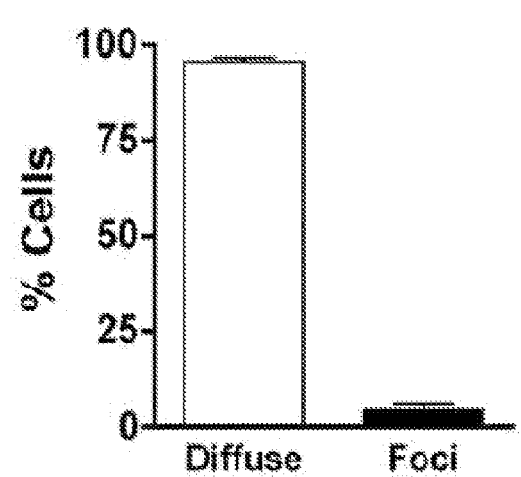
Figure 3C:
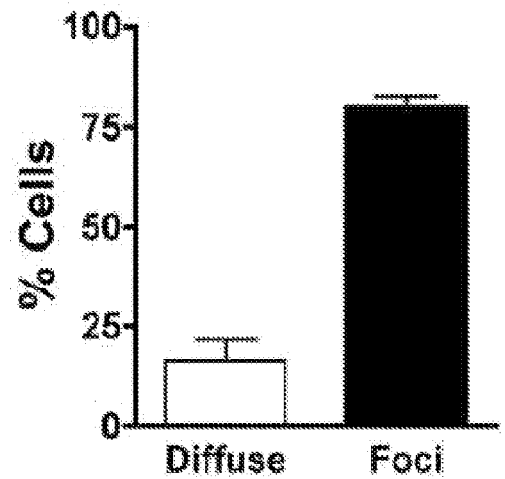

In female hESCs, both chromosomes should be active, but one X chromosome becomes silenced upon differentiation. See Dhara & Benvenisty, 2004, *Nucleic Acids Res* 32:3995-4002. Similar to ESCs, female mouse iPSCs have shown reactivation of a somatically silenced X chromosome and have undergone random X-inactivation upon differentiation. See Maherali et al., 2007, *Cell Stem Cell* 1:55-70. Because MeCP2 is an X-linked gene, we examined the ability of the RTT-iPSCs clones described herein to reset the X chromosome (i.e., to erase X-inactivation) and whether X-inactivation would take place again after neuronal differentiation. See FIG. 3A. We stained RTT-iPSCs clones and their respective fibroblasts with an antibody against trimethylated histone 3 Lysine 27 (me3H3K27), an epigenetic silencing mark present on the inactive X chromosome in interphase nuclei. See Silva et al., 2003, *Developmental Cell* 4:481-495. Some, but not all, undifferentiated RTT-iPSCs clones displayed diffuse immunoreactivity throughout the nucleus, similar to some hESCs, showing that the memory of the previous inactivation state had been erased. See FIG. 3B. For further analysis, we only selected clones that displayed a diffuse me3H3K27 pattern to differentiate into neurons. Upon neuronal differentiation, intense nuclear foci staining, a prominent diagnostic of the inactive X, was found in 80% of neurons labeled by the infection of a lentivirus carrying the neuron-specific Synapsin promoter driving the EGFP reporter (Syn::EGFP). Nuclear foci were also present in RTT fibroblasts before reprogramming. See FIG. 3B. We quantified the percentage of cells displaying either a diffuse or intense X-inactivation (nuclear foci). See FIG. 3C. Without wishing to be bound by any theory, it is believed that these data suggest that the majority of cells in selected clones from both hESCs (99%) and iPSCs (95%) have a diffuse pattern. In contrast, differentiated populations of fibroblasts and iPSC-derived neurons have me3H3K27 nuclear foci staining, indicating X-inactivation.

Figure 3D:
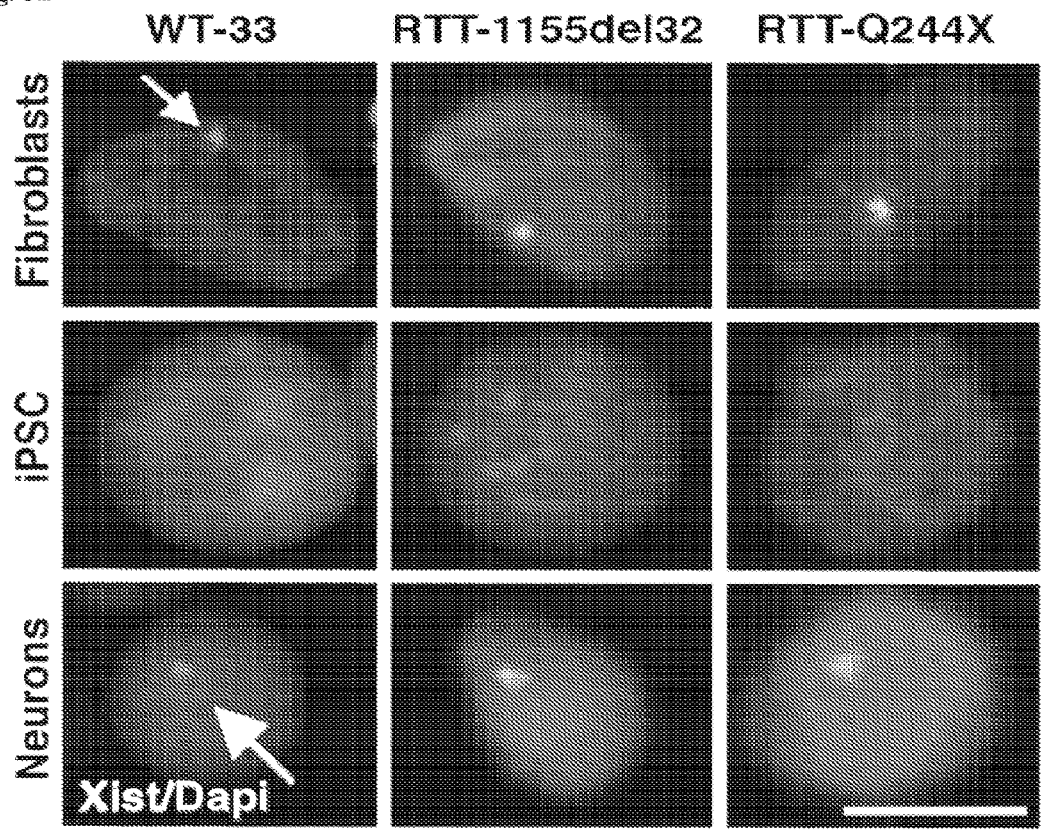
Figure 3E:
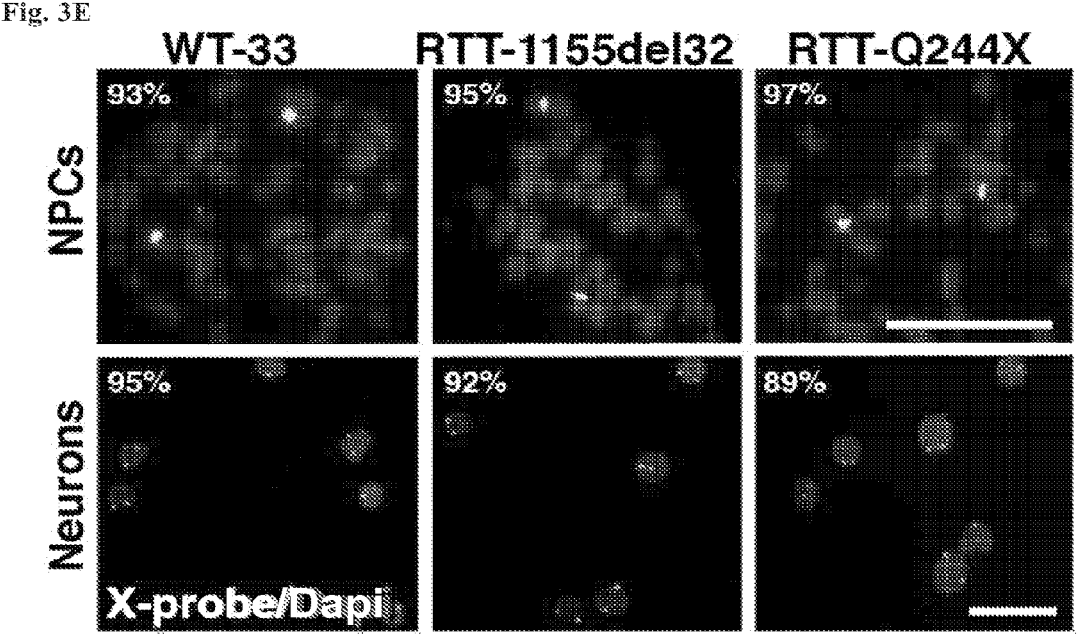
Figure 3F:
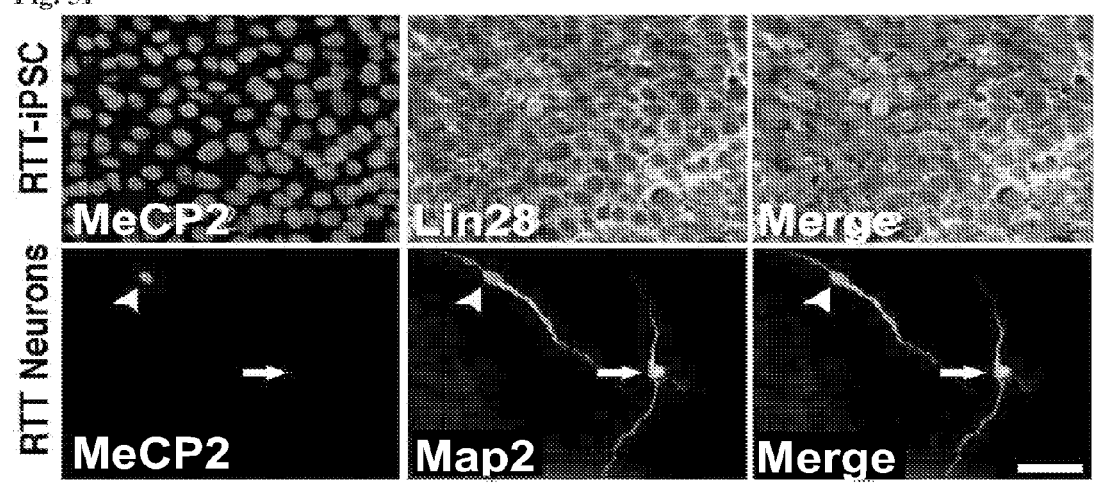

We also used fluorescent in situ hybridization (FISH) to visualize Xist RNA, a noncoding transcript involved in X chromosome silencing that physically wraps the inactive X. See Lucchesi et al., 2005, *Annu Rev Genet* 39:615-651. Before reprogramming, the majority of fibroblasts exhibit a clear Xist cloud. The signal is lost after reprogramming, indicating that selected iPSC clones have two active X chromosomes under the culture conditions. A Xist cloud is also observed in iPSC-derived neurons. See FIG. 3D. Fluorescent in situ hybridization (FISH) analysis using a centromeric X-chromosome probe in iPSC-derived NPCs and neurons showed the presence of two X chromosomes. See FIG. 3E. As a consequence of both X-chromosomes' activation after reprogramming, the MeCP2 protein can be detected in undifferentiated iPSCs from RTT patients. See FIG. 3F. However, after differentiation, RTT-iPSC-derived neurons recapitulated X-inactivation, and the population became mosaic regarding MeCP2 expression. Immunostaining was performed on several RTT-iPSC clones, and a representative example of MeCP2 expression after differentiation is shown in FIG. 3F. Clones obtained from RTT fibroblasts carrying the 1155del32 MeCP2 mutation do not produce a full-length MeCP2 protein. See Traynor et al., 2002, *BMC Medical Genetics* 3:12.

Figure 3G:
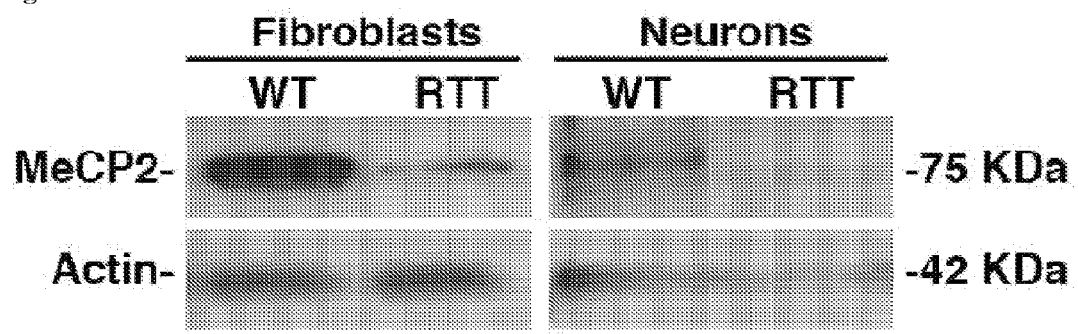
Figure 9A:
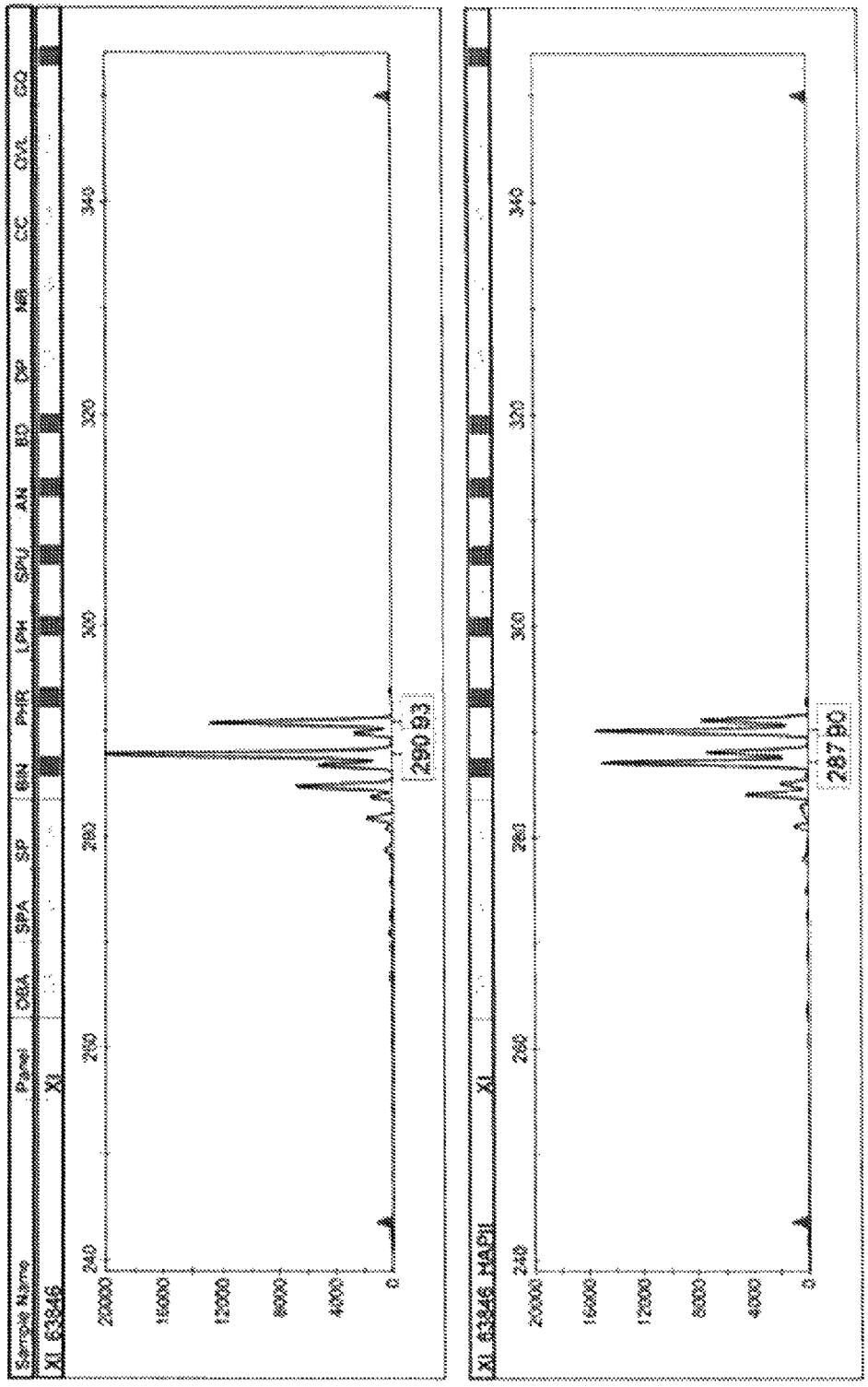
FIG. 9A: When random inactivation is present, the maternal and paternal alleles are represented at similar proportions.
Figure 9B:
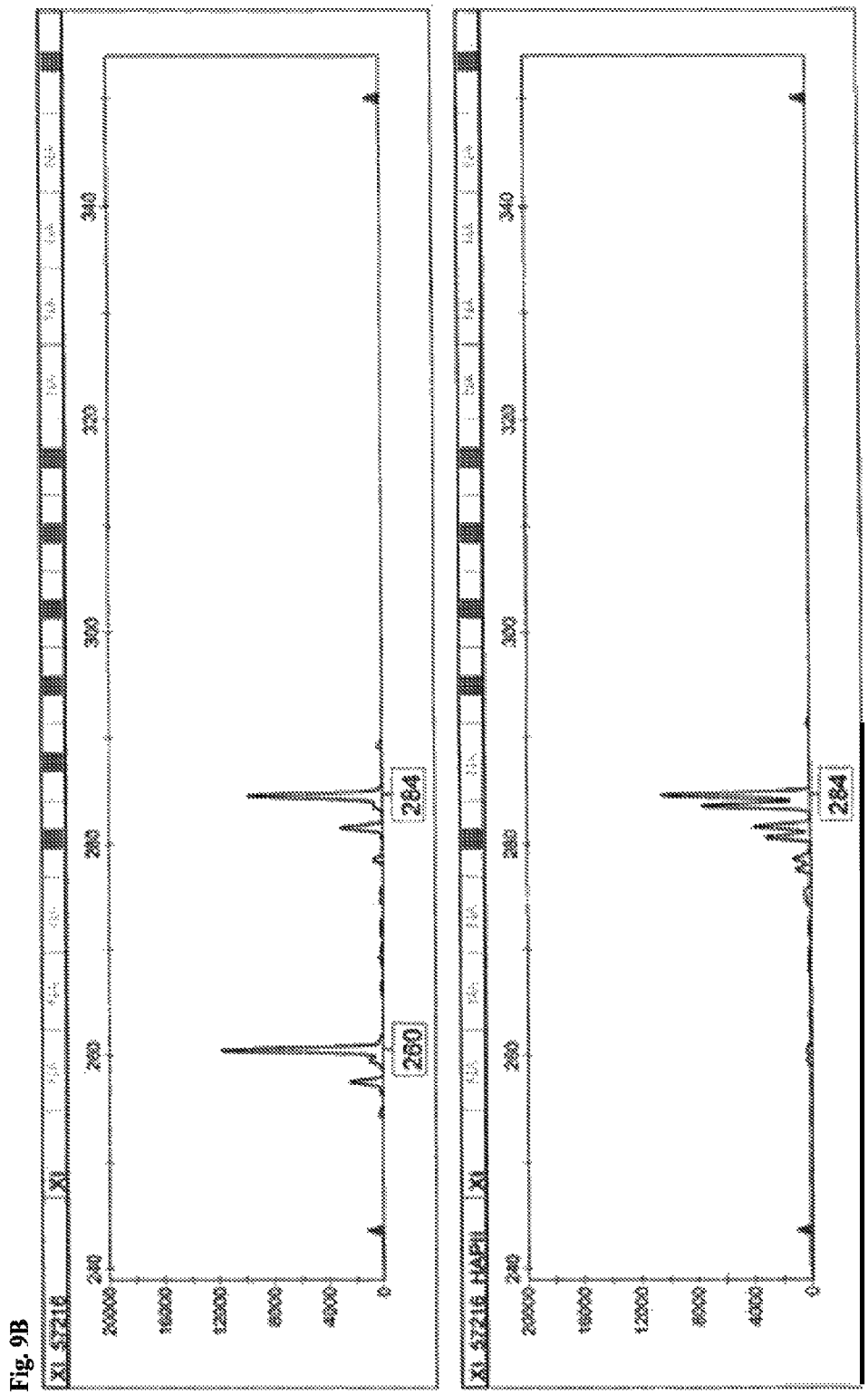
FIG. 9B: In contrast, in a condition where non-random inactivation is present, the more commonly inactive allele will be preferentially amplified and this will be detected by a stronger peak.
Figure 9C:
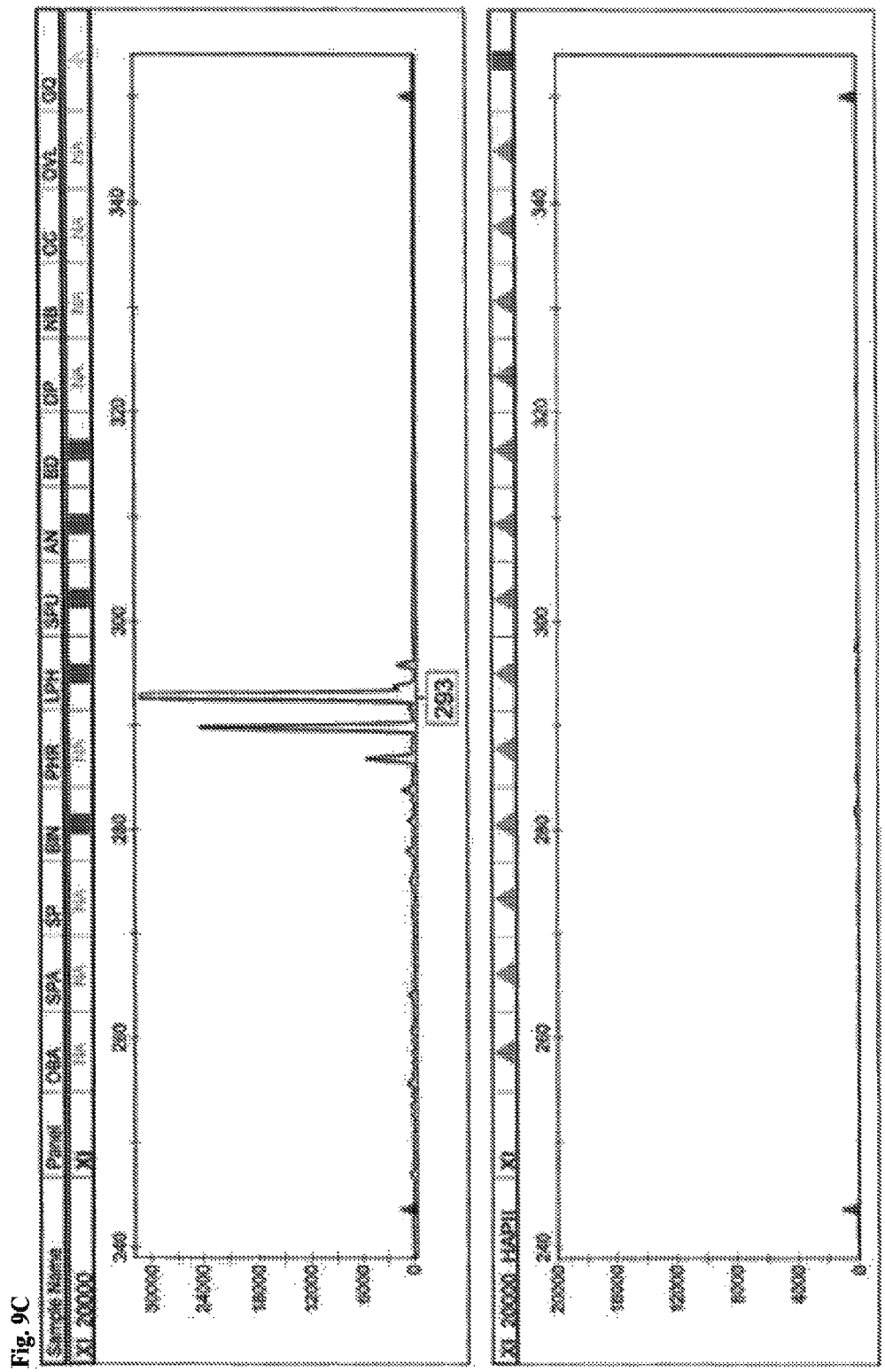
FIG. 9C: A male control is displayed showing a single peak before HpaII digestion.
Figure 9D:
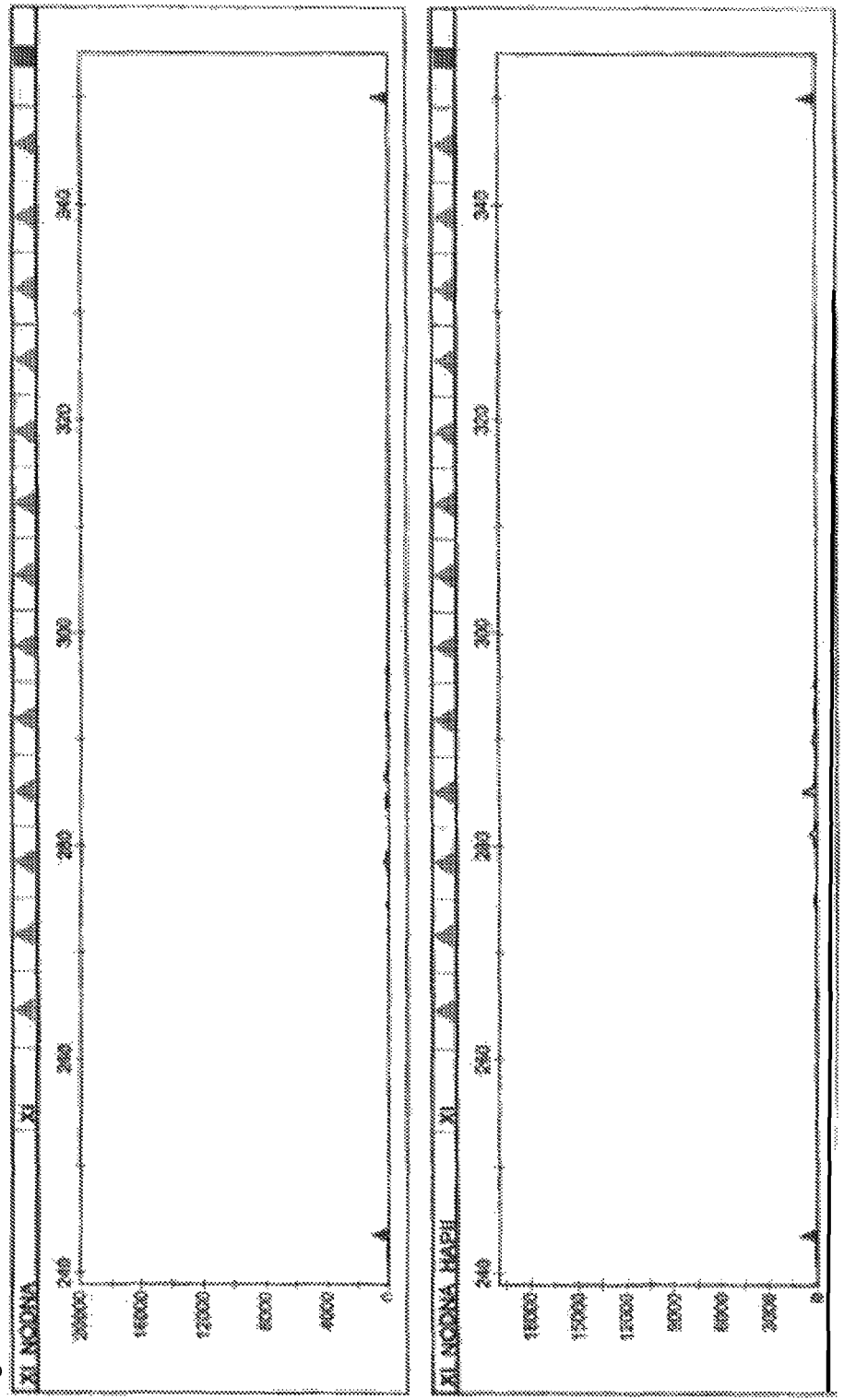
FIG. 9D: A PCR was run without DNA template as a control.
Figure 9E:
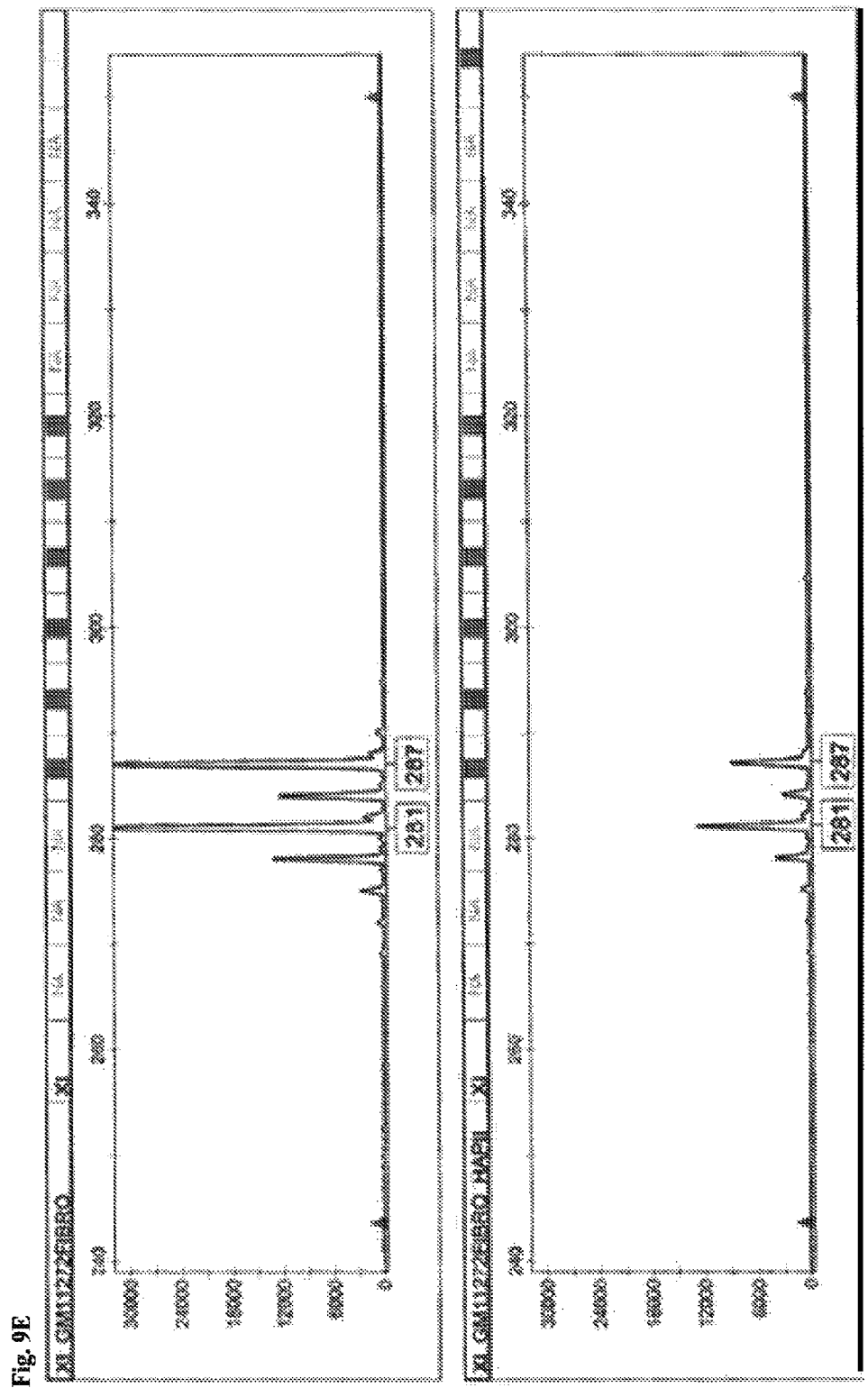
FIG. 9E: Fibroblasts carrying the 1155del32 MeCP2 mutant (GM11272) displayed random X-inactivation.
Figure 9F:
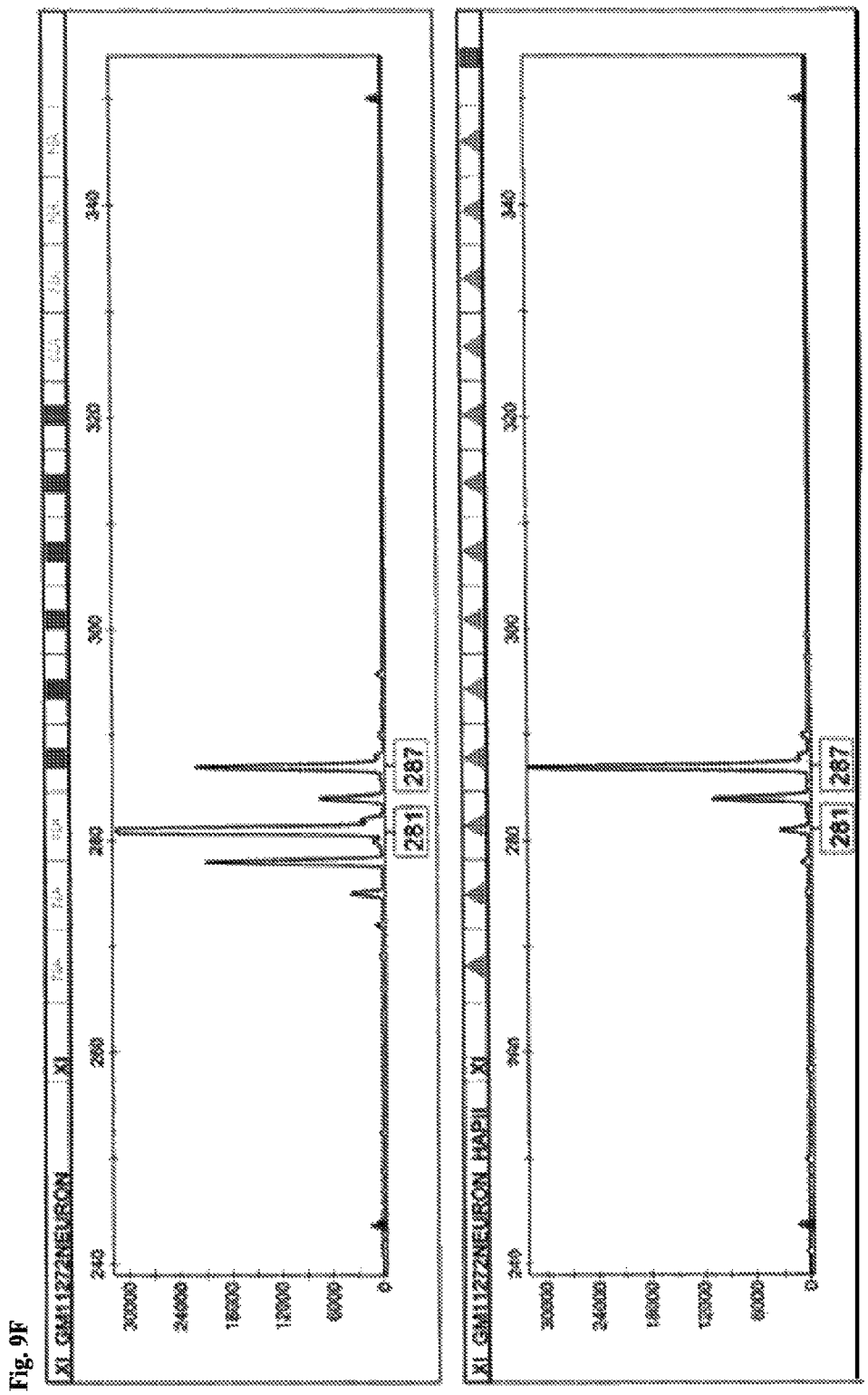
FIG. 9F: RTT-1155del32-derived neurons showed highly skewed X-inactivation.

Next, we selected one WT-iPSC clone (WT-33 C1) and one RTT-iPSC clone (1155del32 C15) to determine whether the RTT-iPSC-derived neuronal population showed reduced MeCP2 protein levels. As expected, we observed a reduction in the full-length MeCP2 protein amounts in both fibroblasts and neurons derived from the RTT-iPSC clone. See FIG. 3G. We tested the original fibroblasts and iPSC-derived neurons from this patient for X-inactivation using standard methodology for the androgen receptor locus. See Allen et al., 1992, *Am J Hum Genet* 51:1229-1239. RTT fibroblasts carrying the 1155del32 MeCP2 mutation had a 55:45 distribution, but RTT-derived neurons showed highly skewed X-inactivation, with a 96:4 distribution. See FIGS. 9A-9F. The data depicted in FIGS. 9A-9F are summarized in Table 3 following, with naming scheme as follows: FIG. 9A: XI_63846, XI_63846_HapII; FIG. 9B: XI_57216, XI_57216_HapII; FIG. 9C: XI_20000, XI_20000_HapII; FIG. 9D: XI_NoDNA, XI_NoDNA_HapII; FIG. 9E: XI_GM11272Fibro, XI_GM11272_HapII; FIG. 9F: XI_GM11272Neuron, XI_GM11272Neuron_HapII.

TABLE 3

Androgen receptor analysis. See FIGS. 9A-9F.

| Sample Name | Peak Area1 | Peak Area2 | Corr. Factor | Corr. Peak2 (Hpa) | Corr. Total | Peak1 % | Peak2 % | X1:Xa |
|---|---|---|---|---|---|---|---|---|
| XI_63846 | 156508 | 87390 | 1.7909 | | | | | |
| XI_63846_HapII | 100309 | 103847 | | 185981.08 | 286290.08 | 35 | 65 | 65:35 (Random Control) |
| XI_57216 | 87250 | 73588 | 1.1857 | | | | | |
| XU7216_HapII | 79106 | | | 0 | 79106 | 100 | 0 | 100 (Highly Control) |
| XI_20000 | 325981 | | | | | | | Male Control |
| XI_20000_HapII | | | | | | | | Male Control |
| XI_NoDNA | | | | | | | | No DNA |
| XI_NoDNA_HpaII | | | | | | | | No DNA |
| XI_GM11272 Fibro | 273822 | 245617 | 1.1148 | | | | | |
| XI_GM11272 Fibro_HapII | 85193 | 61995 | | 69114.09 | 154307.09 | 55.2 | 44.8 | 55:45 (Random) |
| XI_GM11272 Neuron | 330180 | 150314 | 2.1966 | | | | | |
| XI_GM11272 Neuron_HapII | 19851 | 229017 | | 503059.15 | 522910.15 | 3.8 | 96.2 | 96:4 (Highly) |

Figure 10A:
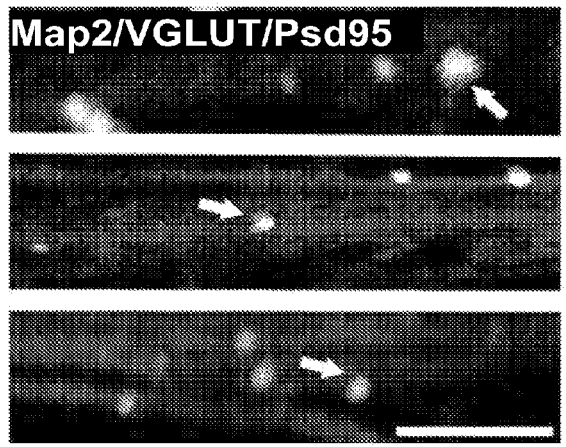
FIG. 10A: Representative images showing co-localization between VGLUT1 and Psd95 (arrows). Bar=5 μm.
Figure 10B:
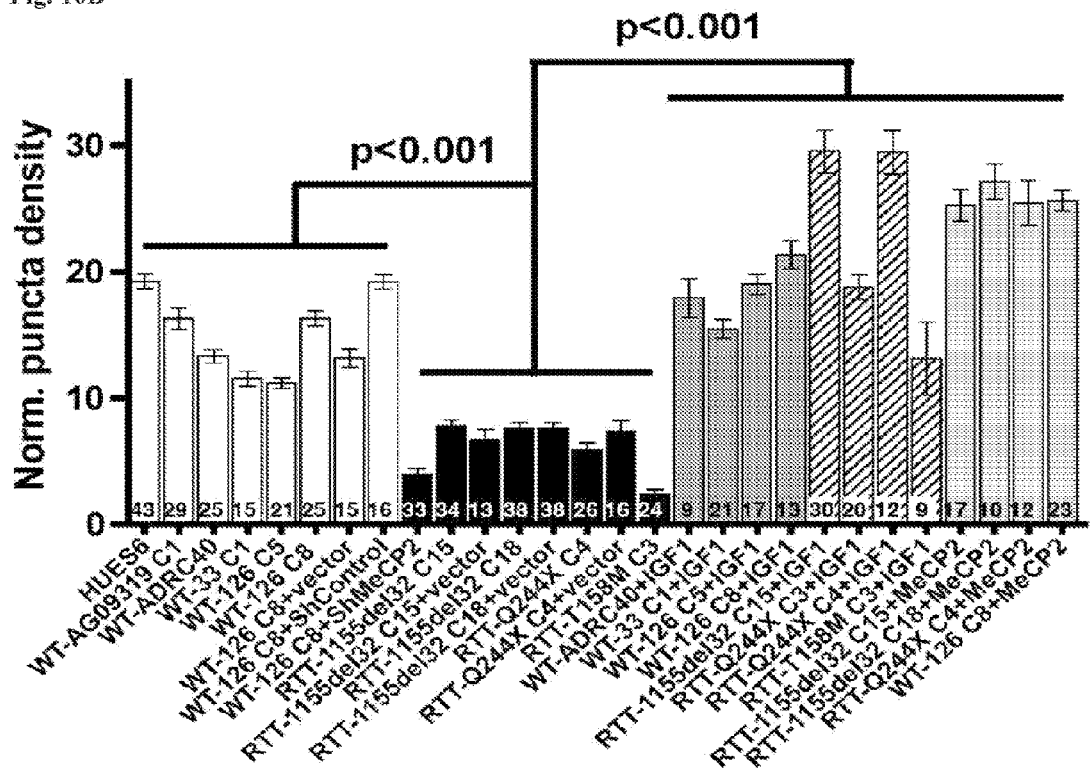
FIG. 10B: Experimental and clonal variation of VGLUT1 puncta quantification in different individuals. The order of histogram entries is as provided in the figures.
Figure 10C:
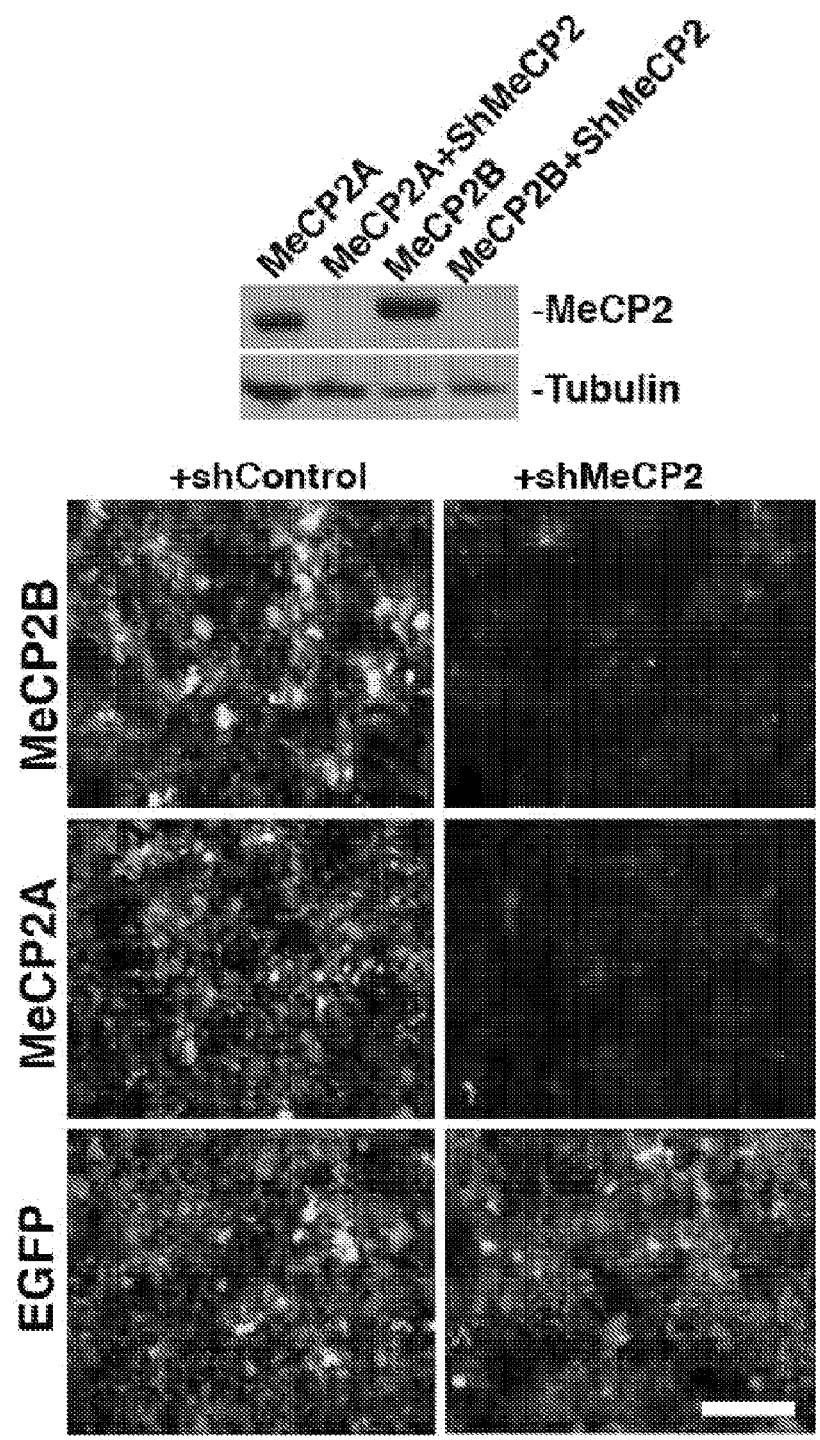
FIG. 10C: Efficient expression and knock-down of both MeCP2 isoforms by a specific shRNA against MeCP2. Bar=50 μm. Two alternatively spliced MeCP2 transcripts have been characterized, isoforms A and B, which differ only in their most 5' regions. The MeCP2 isoform B is more prevalent in the brain and during neuronal differentiation.
Figure 10D:
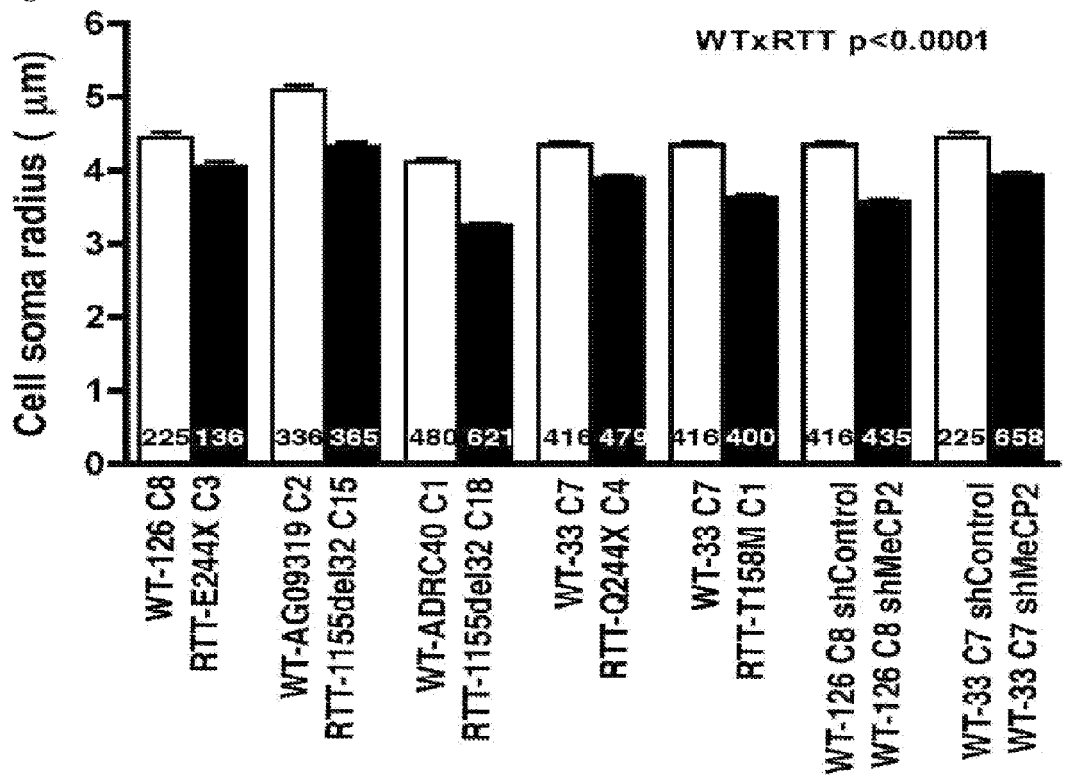
FIG. 10D: Histogram shows cell soma radius for several RTT and WT clones, as indicated in the figure.
Figure 10E:
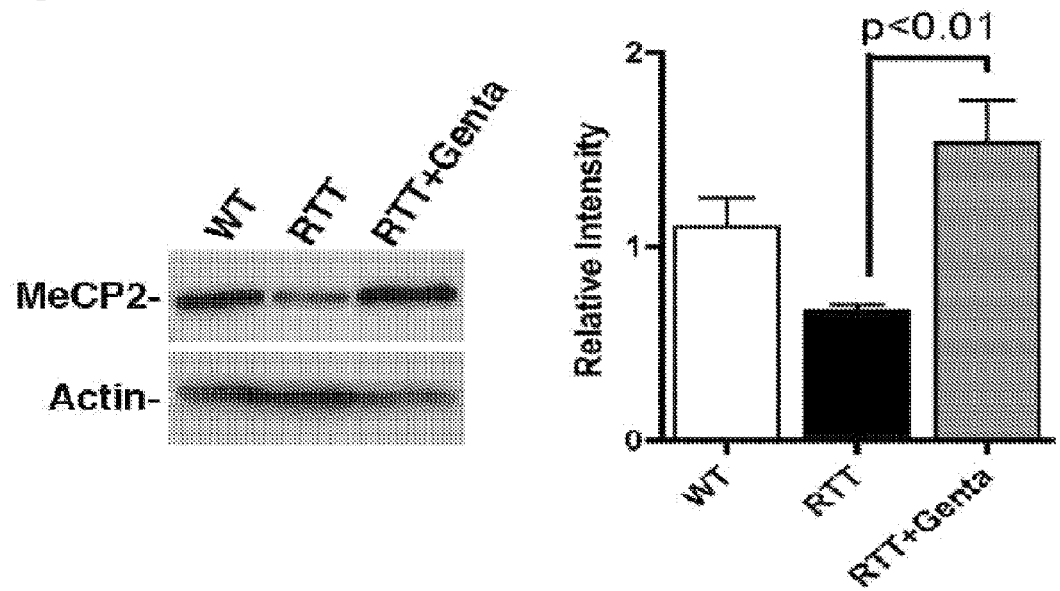
FIG. 10E: WT MeCP2 protein levels detected in control and RTT neurons (Q244X). Gentamicin treatment in RTT neurons increased protein levels after 2 weeks. Numbers of neurons analyzed (n) are shown within the bars in graphs (FIG. 10B) and (FIG. 10D). Order of X-axis entries for histogram of FIG. 10E (right panel): WT; RTT; RTT+Genta. Data shown as mean±s.e.m.

In view of the data disclosed herein, and without wishing to be bound by any theory, it is believed that the outcome of the X-inactivation process, measured by the androgen receptor locus, is consistent within the same clone. An independent differentiation of the same clone (RTT-1155del32 C15) yielded a 98:2 distribution. It is further believed that the androgen receptor locus analysis was not conclusive for the MeCP2 mutation Q244X cells. However, a reduction of 50% in the amount of MeCP2 protein level (FIG. 10E) is consistent with a random X-inactivation.

The present data show that X-inactivation was erased in selected reprogrammed RTT-iPSCs clones and subsequently restored during neuronal differentiation. Importantly, the recapitulation of X-inactivation produces mosaic neuronal cultures with different ratios of cells expressing normal MeCP2 levels, mimicking what is observed in RTT patients' brains. The data do not preclude that partial reprogramming from a single fibroblast or retention of the X-inactivation would lead to clones with highly skewed X-inactivation, where neurons would express only the normal or mutant form of MePC2. In fact, we do observe WT and RTT-iPSC clones retaining X-inactivation after reprogramming. The RTT-T158M C3-derived neurons showed 100:0 distribution. The expression of the mutant MeCP2 allele was confirmed by sequencing.

Normal Cellular Proliferation from iPSCs-RTT-Derived NPCs

Figure 4A:
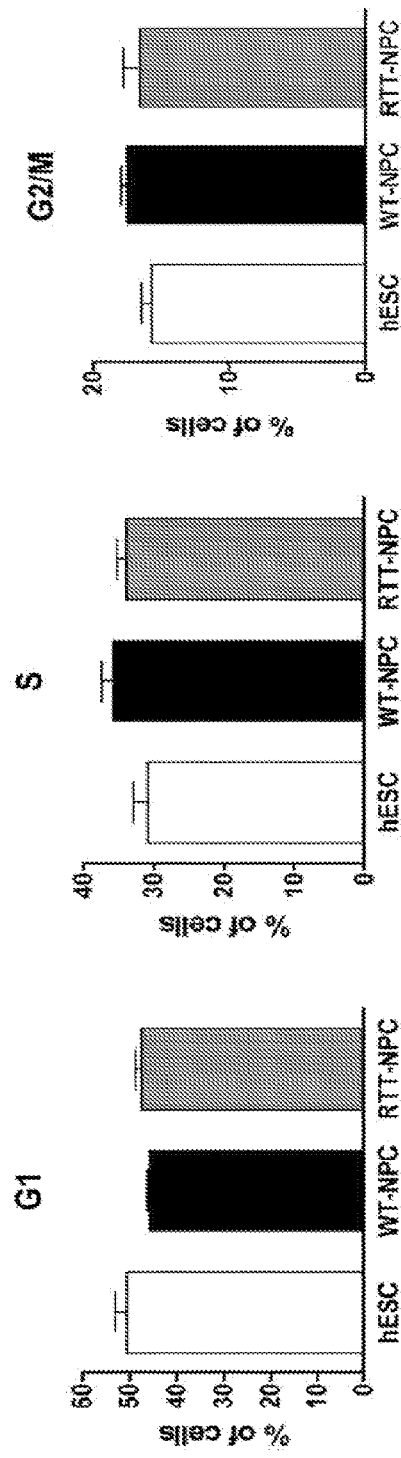
FIG. 4A: Proliferating RTT NPCs displayed no signal of aberrant cell cycle when compared to controls. X-axis of histogram FIG. 4A in order (left to right): hESC; WT-NPC; RTT-NPC.

An increased incidence of large head size has been reported in autism. See e.g., Piven et al., 1995, *Id*. Other studies have suggested that the autistic brain is smaller at birth, followed by rapid head growth during early development and then a period of reduced brain growth (Courchesne et al., 2003, *J Am Med Asso* 290:337-344). Head growth deceleration has also been reported for RTT patients. See Hagberg et al., 2001, *Brain Dev* 23 Suppl 1:S227-229. Since the cellular mechanism behind this phenomenon is unknown, we investigated whether a perturbed NPC replication cycle was affected in RTT. NPCs derived from RTT-iPSCs, WT-iPSCs and hESCs (Cyth25 and HUES6) were generated and kept under proliferating conditions in the presence of FGF2. NPCs derived using the protocol described herein had identical passage numbers and were analyzed for cell cycle by flow cytometry. Our results showed no significant differences in any cycle phase between HESC-, WT-iPSC- and RTT-iPSC-derived NPCs (FIG. 4A), though we cannot exclude the possibility that altered head growth in RTT patients is caused by eventual abnormal NPC proliferation in another developmental stage. We then investigated potential phenotypic changes in RTT neurons compared to controls.

Figure 4B:
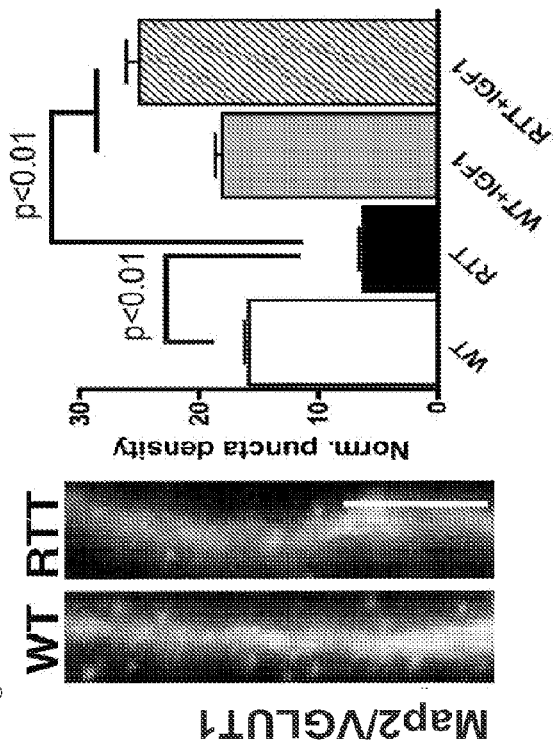
FIG. 4B: Representative images of neurons showing VGLUT1 puncta on Map2 neurites. Histogram (right panel) shows synaptic density in RTT and WT neurons. IGF1 treatment increased VGLUT1 puncta number in RTT-derived neurons. Bar=5 μm. X-axis of histogram FIG. 4B in order (left to right): WT; RTT; WT+IGF1; RTT+IGF1.

Reduced Glutamatergic Synapse Number and Morphological Alterations in RTT Neurons Strong evidence implicates synapse alteration with ASD, including RTT. See e.g., Zoghbi, 2003, *Science* 302:826-830. Loss of MeCP2 and doubling of MeCP2 dosage in mice have opposite effects on excitatory synapse numbers in individual neurons. See Chao et al., 2007, *Neuron* 56:58-65. These results suggest that MeCP2 may be a rate-limiting factor in regulating glutamatergic synapse formation and indicate that changes in excitatory synaptic strength may underlie global network alterations in RTT. Therefore, we determined whether excitatory synapse numbers were reduced in human RTT neurons. After 8 weeks of differentiation, glutamatergic neurons were identified using antibodies against VGLUT1 (Takamori et al., 2000, *Nature* 407: 189-194), and dendrites were labeled with Map2. See FIG. 4B. To confirm the specificity of glutamatergic neurons in our cultures, we showed that VGLUT1 puncta were mostly adjacent to the postsynaptic density-95 (Psd95) protein (Niethammer et al., 1996, *J Neurosci* 16:2157-2163). See FIG. 10A. We found a reduction in the density of VGLUT1 puncta from RTT-iPSCs clones carrying 3 different MeCP2 mutations compared to HUES6 and distinct WT-iPSCs-derived Map2-positive neurons, suggesting a specific defect in glutamate transport in RTT cultures. See FIG. 4B and FIG. 10B. Since neurons carrying different MeCP2 mutations showed reduced VGLUT1 puncta in our cultures, we tested whether loss of function of MeCP2 was directly related to the number of glutamatergic synapses in our neuronal cultures. We cloned an shRNA against MeCP2 in a lentiviral vector that is able to knockdown both isoforms of MeCP2. See FIG. 10C. Neurons derived from WT-iPSCs expressing the shMeCP2 showed a similar reduction in VGLUT1 puncta when compared to control neurons expressing a scramble shRNA (shControl). See FIG. 4C and FIG. 10B. Overexpression of MeCP2 using a lentiviral vector (FIG. 10C) increased the number of VGLUT1 puncta in WT and RTT neurons. See FIG. 4D and FIG. 10B. Our data strongly suggest that MeCP2 is a rate-limiting factor in regulating glutamatergic synapse number in human neurons.

Figure 4F:
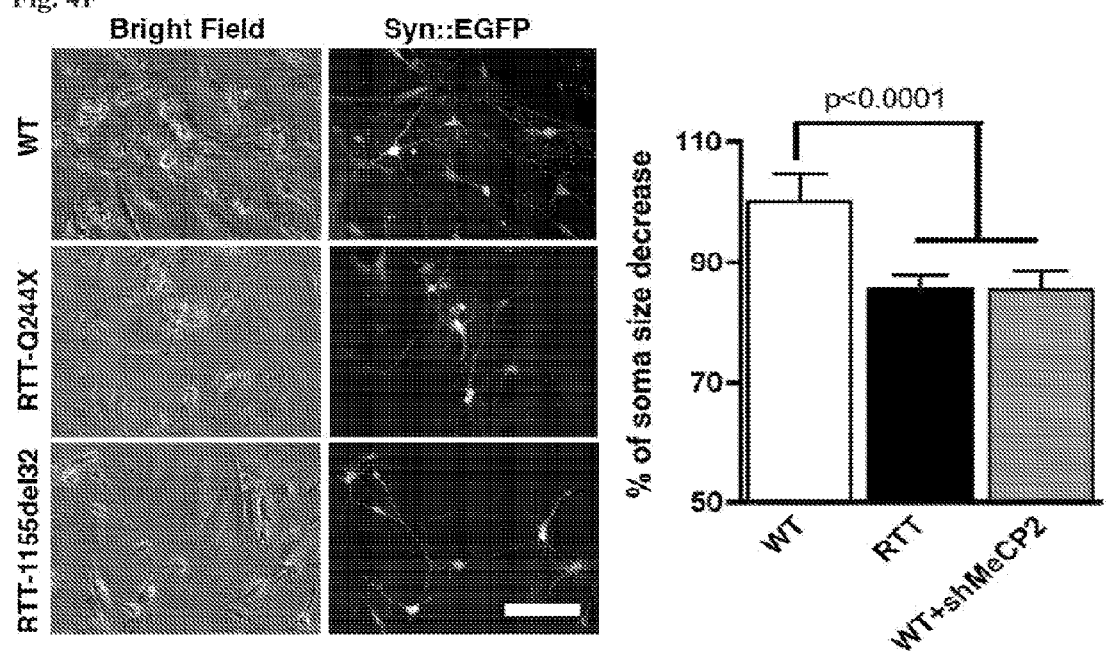
FIG. 4. Alterations in RTT neurons.
FIG. 4C: Reduction of MeCP2 expression decreased the number of glutamatergic synapses in WT neurons. X-axis of histogram FIG. 4C in order (left to right): WT; WT+ShControl; WT+ShMeCP2.
FIG. 4D: Overexpression of MeCP2 increased the number of glutamatergic synapses. X-axis of histogram FIG. 4D in order (left to right): WT+Vector; WT+MeCP2; RTT+Vector; RTT+MeCP2.
FIG. 4E: Representative images of neurites of different genetic backgrounds. Histogram (right panel) shows the spine density from independent experiments using different RTT backgrounds and controls and after expression of shMeCP2. Bar=5 μm. X-axis of histogram FIG. 4E in order (left to right): WT-AG09319 C2; RTT-1155del32 C18; WT-126 C8; RTT-Q244X C3; WT-126 C8+ShControl; WT-126 C8+ShMeCP2. 4F: Representative images of neuronal cell body size. Histogram (right panel) shows the percentage of soma size decrease in RTT compared to WT neurons. Neuronal morphology was visualized using the Syn::EGFP lentiviral vector. Bar=50 μm. X-axis of histogram FIG. 4F in order (left to right): WT; RTT; WT+shMeCP2.
FIG. 4G: A lower dose of gentamicin was able to rescue glutamatergic synapses in RTT neurons. X-axis of histogram FIG. 4G in order (left to right): WT; WT+Genta (400 ug/ml); RTT; RTT+Genta (400 ug/ml); RTT+Genta (100 ug/ml). Numbers of neurons analyzed (n) are shown within the bars in graphs (FIG. 4E) and (FIG. 4G). For all clones and mutations used, refer to FIG. 10 and Tables 2.1 and 2.2. Data shown as mean±s.e.m.

We also investigated whether RTT neurons displayed any morphological alteration when compared to controls. To visualize neuronal anatomy, we infected the cultures with the Syn::EGFP lentivirus. Morphological analysis of RTT neurons revealed that the number of spines in RTT neurites was reduced when compared to WT neurons and after ectopic expression of shMeCP2. See FIG. 4E. Consistent with this observation, the number of spines in dendrites of neurons from postmortem RTT patient brain was previously reported to be lower than that in normal individuals. See Chapleau et al., 2009, *Neurobiol Dis.* 35:219-233. Finally, we documented that the cell soma sizes from neurons derived from the RTT-iPSCs carrying different MeCP2 mutations were smaller when compared to controls (reduction of 14.31±4.83%). Similarly, loss of function using the shMeCP2 knockdown strategy in WT neurons reduced soma size at levels comparable to RTT levels (reduction of 14.52±4.31%). See FIG. 4F and FIG. 10D.

Rescuing a RTT Neuronal Phenotype

Recent studies have shown that re-activation of MeCP2 expression knockout mice led to a prolonged life span and delayed onset or reversal of certain neurological symptoms. See e.g., Giacometti et al., 2007, *Proc Natl Acad Sci USA* 104:1931-1936; Guy et al., 2007, *Science* 315:1143-1147. These reports suggest that some RTT phenotypes can be rescued in vivo. We used our model to analyze the effect of selected compounds that may revert the neuronal phenotype in culture as a validation, e.g., for high-throughput drug screening platforms. Administration of IGF1 was recently described to promote a partial reversal of the RTT-like symptoms in a mouse model. See Tropea et al., 2009, *Proc Natl Acad Sci USA* 106:2029-2034. We treated RTT-derived neurons carrying different MeCP2 mutations in culture with IGF1 and observed an increase in glutamatergic synapse number, suggesting that the drug treatment could correct the RTT neuronal phenotype. See FIG. 4B and FIG. 10B.

Figure 4G:
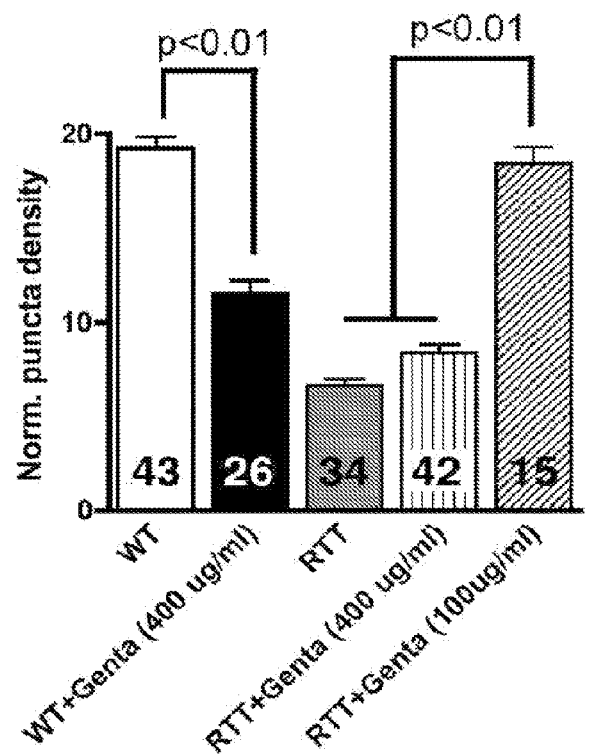

It is believed that around 60% of MeCP2 mutations in RTT are nonsense mutations. See Laccone et al., 2001, *Hum Mutat* 17:183-190. Thus, we tested whether we could increase MeCP2 expression levels in affected neurons by suppressing the nonsense mutation (Q244X) with read-through of the premature stop codon using pharmacological treatments. For example, high concentrations of aminoglycosides antibiotics, such as gentamicin and the like as known in the art, can bind to the 16S rRNA, impairing ribosomal proofreading. See Kellermayer, 2006, *Eur J Med Genet* 49:445-450. As a consequence, a full-length protein is produced by incorporating random amino acid at the stop codon position. We treated RTT-Q244X clones 3- and 4-derived neurons with two different doses of gentamicin and found that MeCP2 protein levels and glutamatergic synapse numbers were increased after 1 week. See FIGS. 4G and 10E. Treatment with higher gentamicin dose (400 ug/ml) for the same period did not rescue RTT neurons and lowered the number of VGLUT1 puncta in control neurons. See FIG. 4G.

Accordingly, without wishing to be bound by any theory, it is believed that RTT patient-derived neurons display changes in neuronal morphology and in number of synapses, which belief prompted us, e.g., to explore putative circuit alterations in vitro.

Altered Activity-Dependent Calcium Transients in RTT-iPSC-Derived Cells

Early in neural development, spontaneous electrical activity leads to increases in intracellular calcium levels and activation of signaling pathways that are important in regulating several neuronal processes. See Spitzer et al., 2004, *Trends Neurosci* 27:415-421. Recently, a disturbance in calcium homeostasis during early postnatal development was reported in a MeCP2 knockout model. See Mironov et al., 2009, *J Physiol* 587:2473-2485. Moreover, several studies have shown that functional mutations in genes encoding voltage-gated calcium channels and in genes whose activity is modulated by calcium, such as MeCP2, could lead to ASD. See e.g., Splawski et al., 2006, *J Biol Chem* 281: 22085-22091; Zhou et al., 2006, *Neuron* 52:255-269. Neuronal activity-induced calcium influx can trigger the calcium/calmodulin-dependent protein kinase (CamK). CamK activation has been reported to induce phosphorylation of MeCP2, which was further postulated to regulate neuronal spine maturation. See e.g., Tao et al., 2009, *Proc Natl Acad Sci USA* 106:4882-4887; Zhou et al., 2006, Id. Although these studies raised an interesting link between neuronal activity and spine maturation, the extent of cellular alteration in human ASD neurons was never characterized. To test if RTT-iPSCs-derived neuronal networks are affected in our system, we pre-loaded the cells with the calcium indicator fluo-4AM and highlighted neurons using the Syn::DsRed vector. Cultures with similar cell density and numbers of DsRed-positive neurons were used. See FIG. 8B. Spontaneous calcium transients were analyzed from WT and RTT neuronal networks in several independent experiments over time. See FIGS. 5A-5B.

Figure 5A:
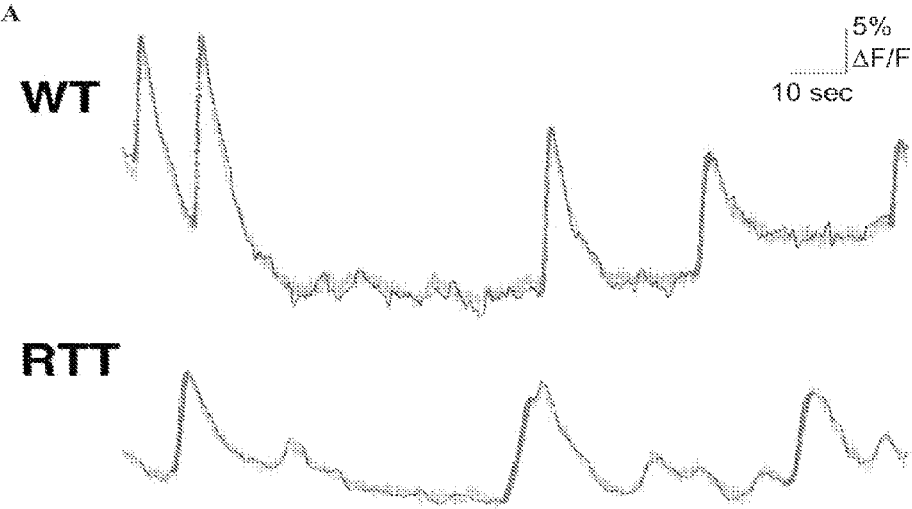
FIG. 5A: Representative examples of WT (upper) and RTT (lower) calcium signal traces. Observed traces correspond to the calcium rise phase detected by the algorithm used.
Figure 5B:
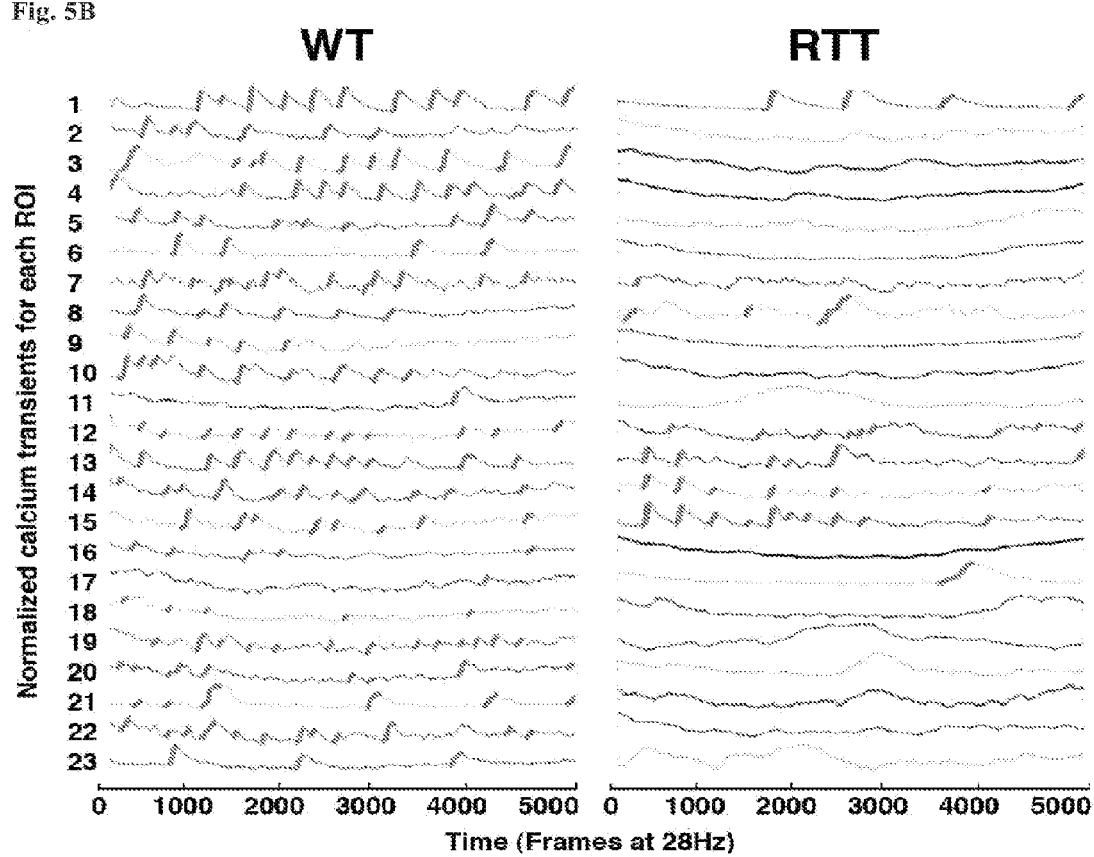
FIG. 5B: Fluorescence intensity changes reflecting intracellular calcium fluctuations in RTT and WT neurons in different Regions of Interest (ROI).
Figure 5C:
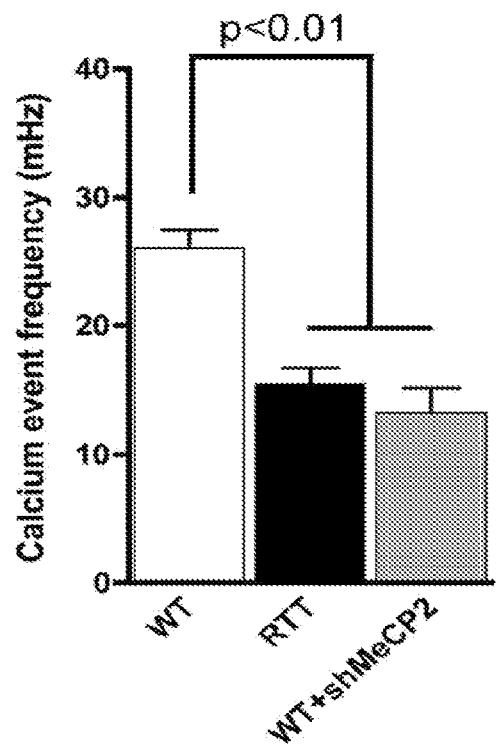
FIG. 5C: RTT neurons show a lower average of calcium spikes when compared to WT control neurons.
Figure 5D:
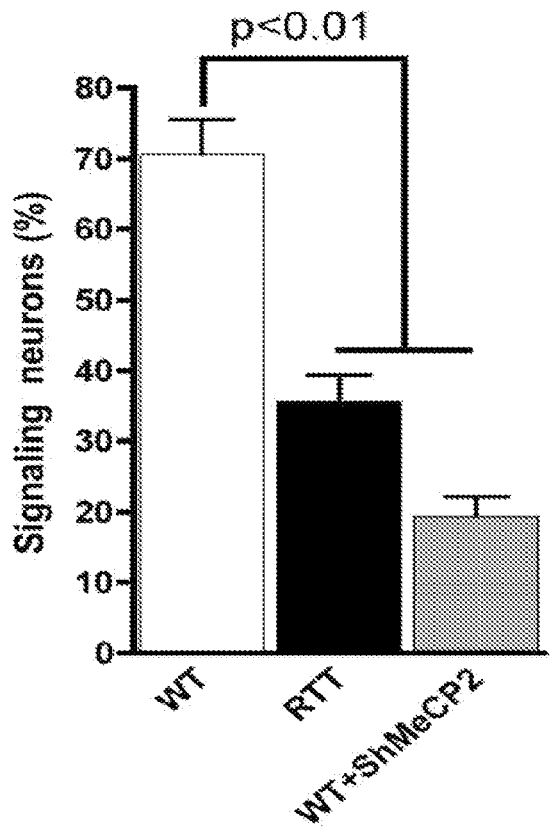
FIG. 5D: The percentage of Syn::DsRed-positive neurons signaling in the RTT neuronal network is significantly reduced when compared to controls. X-axis of histograms FIGS. 5C-5D in order (left to right): WT; RTT; WT+ShMeCP2. Data shown as mean±s.e.m. See also FIG. 11.
Figure 11B:
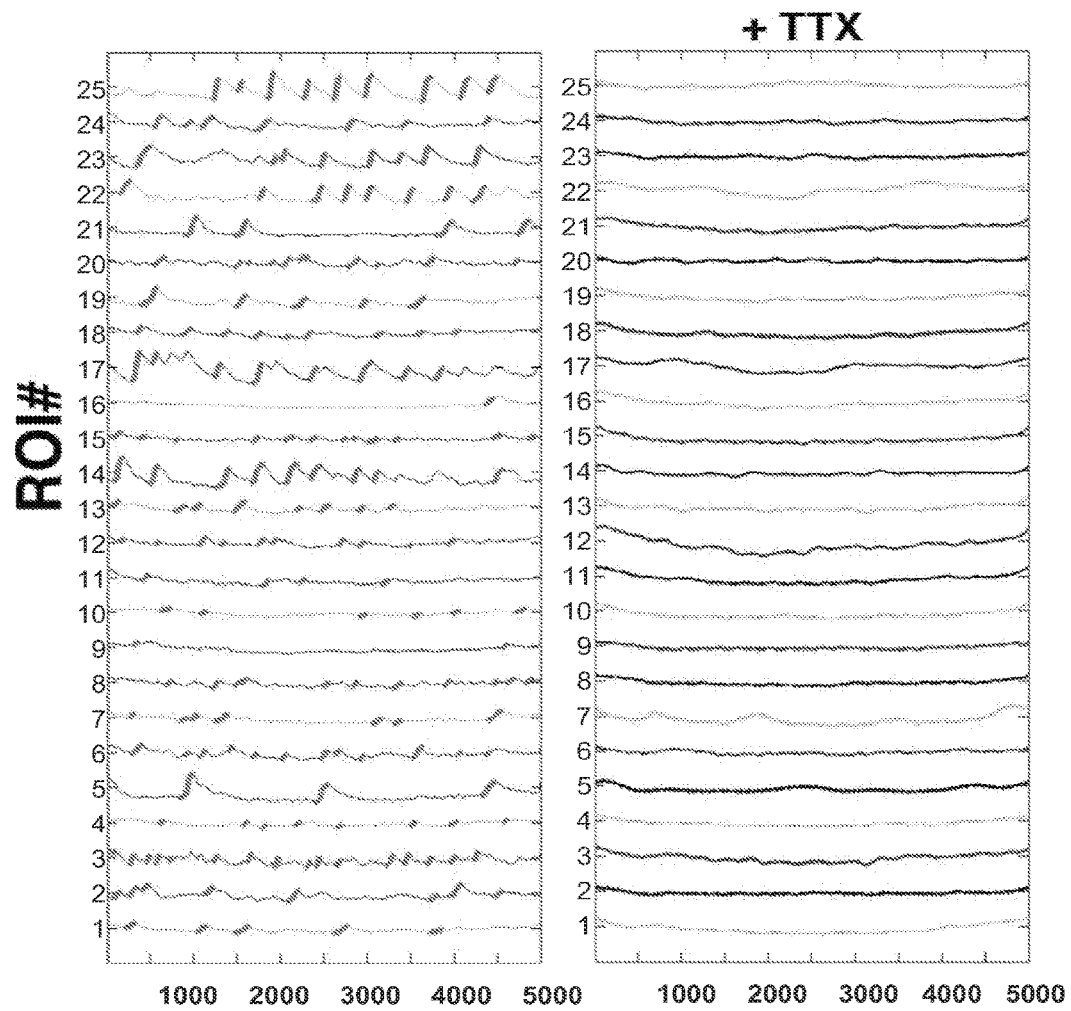
FIG. 11B: Blocking voltage-gated sodium channels using TTX prohibited the generation of action potentials and resulted in complete elimination of neuronal intracellular calcium transients.
Figure 11C:
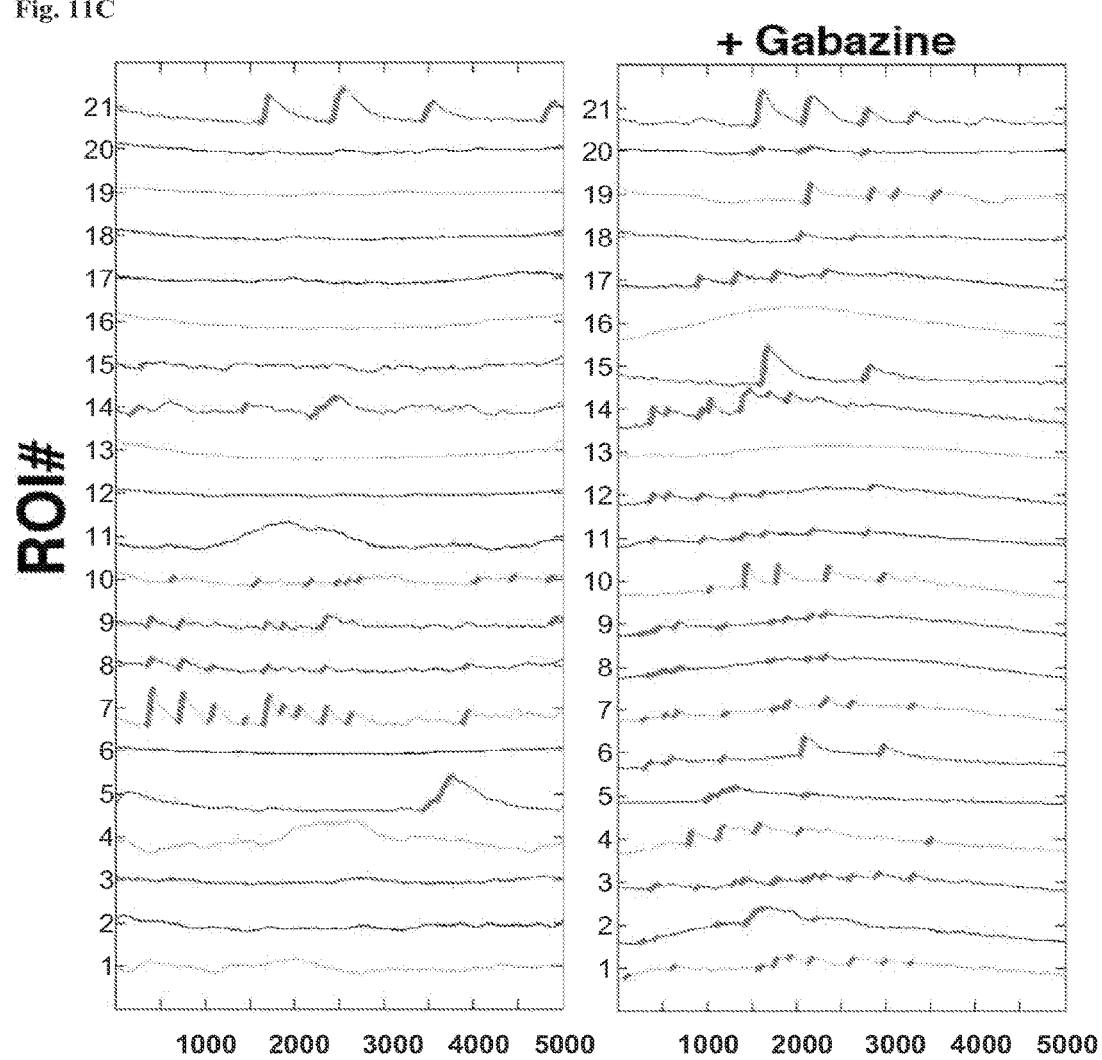
FIG. 11C: Gabazine increased the number of calcium transients in the iPSC-derived neuronal networks. Traces correspond to the calcium rise phase detected by the algorithm used.
Figures 11D, 11E, 11F:
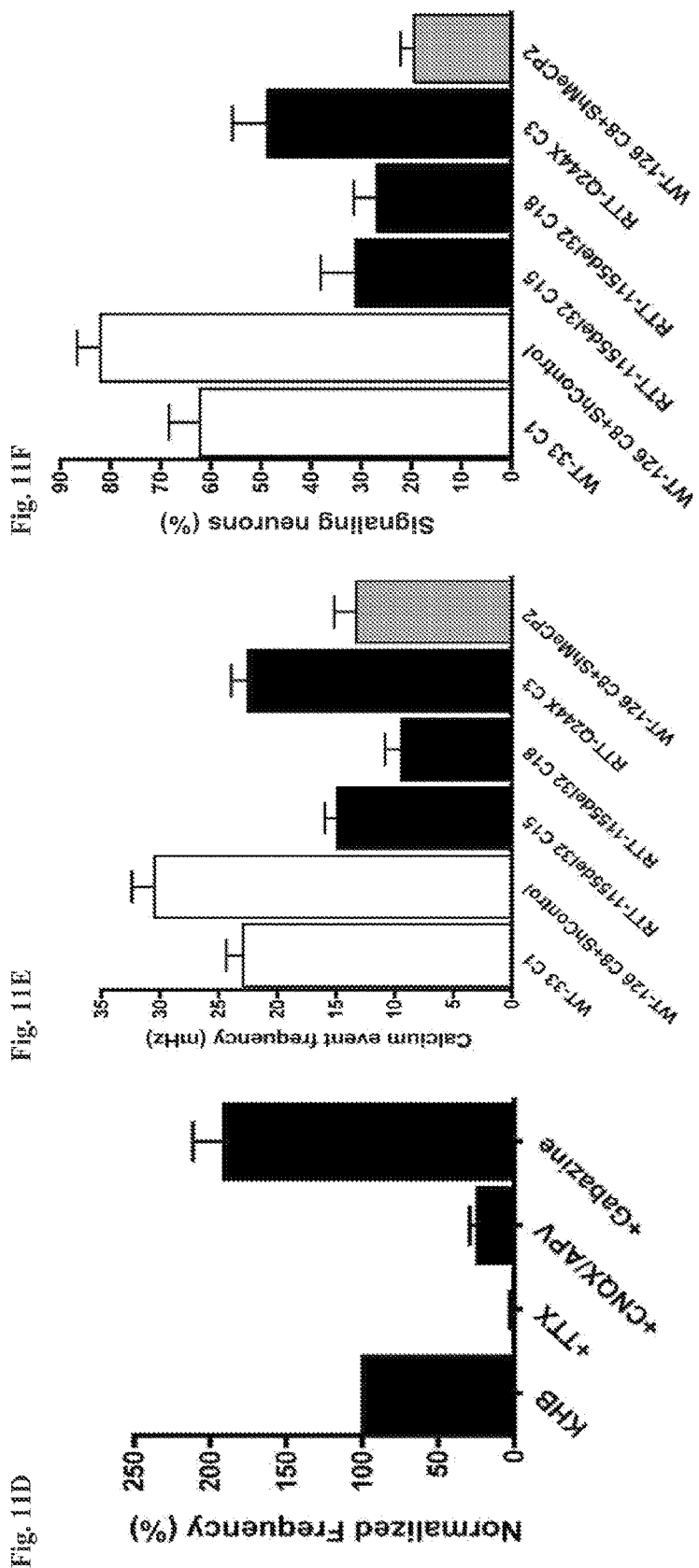
FIG. 11D: Histogram shows the normalized frequency of neurons with calcium transients after drug treatments. Order of histogram entries (left to right): KHB; +TTX; +CNQX/APV; +Gabazine.
FIG. 11E: Histogram shows the event frequency decrease in RTT and shMeCP2-treated WT neurons compared to WT controls neurons. Order of histogram entries (left to right): WT-33 C1; WT-126 C8+ShControl; RTT-1155del32 C15; RTT=1155del32 C18; RTT=Q244X C3; WT-126 C8+ShMeCP2.
FIG. 11F: Bar graph shows the percentage of signaling neurons in RTT and shMeCP2-treated WT neurons compared to WT control neurons. Order of histogram entries (left to right): as in FIG. 11E.

In our analyses, we considered calcium transients generated by synaptic activity. Neurons were selected after confirmation that calcium transients were blocked with TTX or with the glutamate receptor antagonists CNQX (AMPA) and APV (NMDA) treatments, indicating neuronal signaling dependence on local synaptic connections. See FIGS. 11A, 11B, 11D. Gabazine, an antagonist of GABAa receptors, increased the number of calcium transients in the networks, indicating the presence of glutamatergic and gabaergic synapses in our system. See FIGS. 11C-11D. A representative example of calcium tracing in control and RTT neurons is depicted in FIG. 5A and shows a sharp increase in amplitude followed by a decrease over time. The frequency of calcium oscillations in RTT neurons and in WT neurons expressing shMeCP2 was abnormally decreased when compared to controls, suggesting a deficiency in the neuronal network connectivity and activity dynamics. See FIGS. 5B-5C and FIGS. 11E and 11F. The deficiency in connectivity was further corroborated by a decrease in the percentage of Syn::DsRed-positive neurons exhibiting calcium transients in the RTT cultures when compared to controls. See FIG. 5D and FIG. 11F.

Decreased Frequency of Spontaneous Postsynaptic Currents in RTT Neurons

Figure 6A:
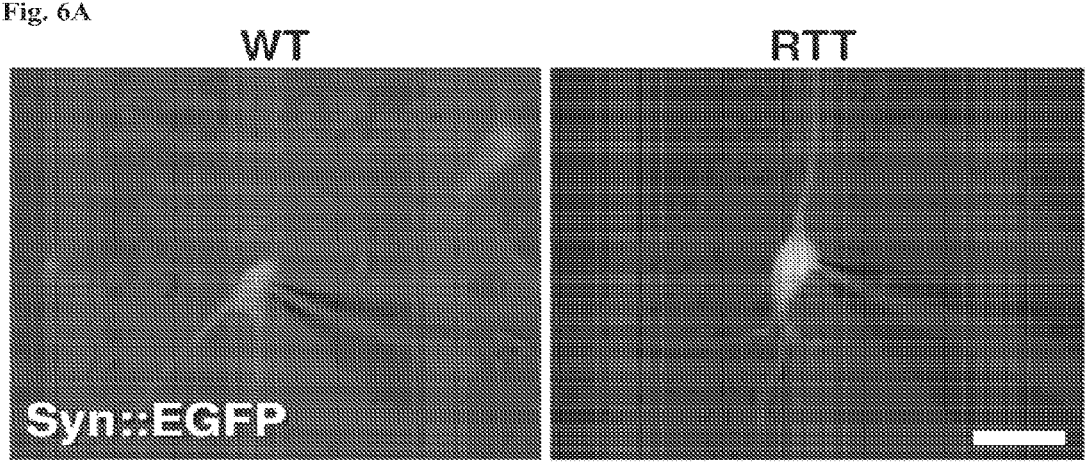
FIG. 6A: Fluorescence micrographs of representative WT (left) and RTT (right) neurons. Bar=10 μm.
Figure 6B:
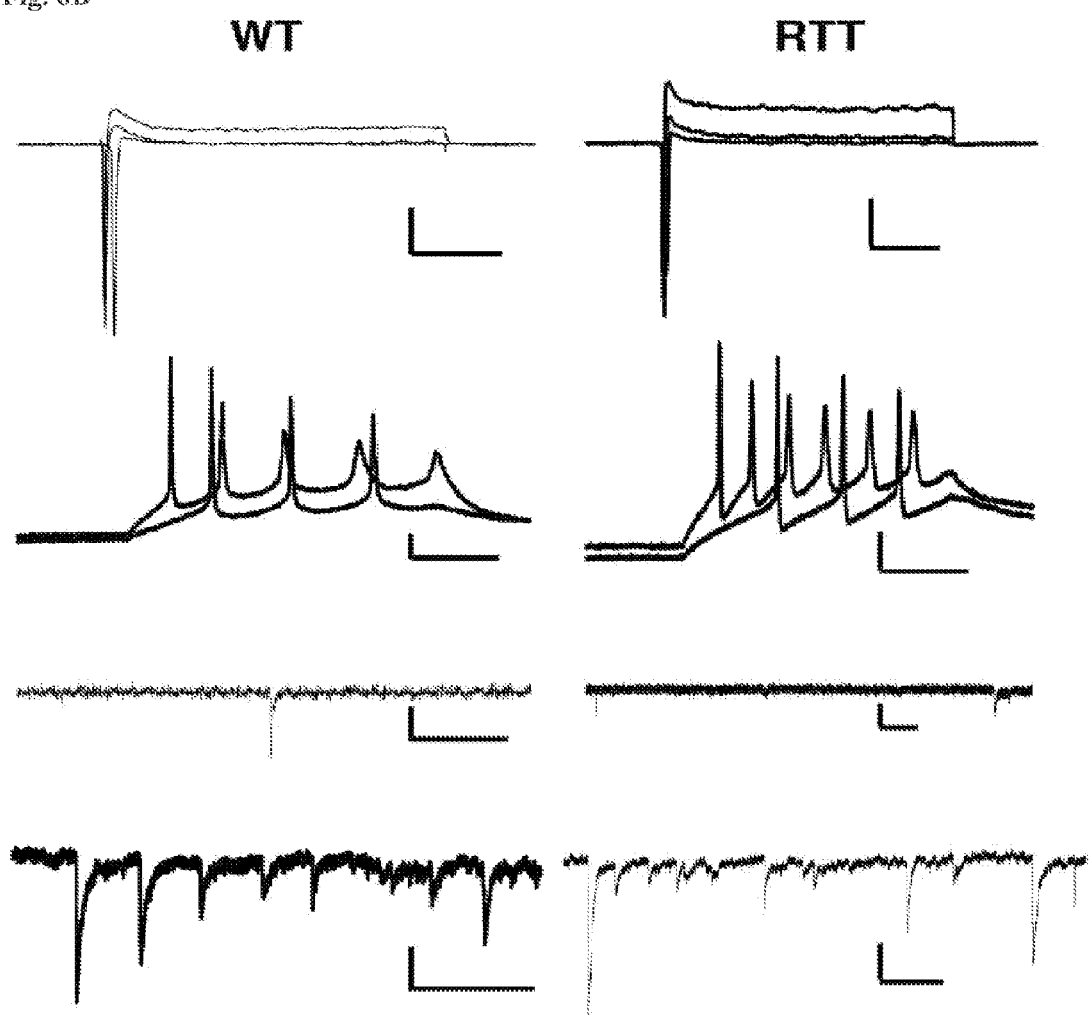
FIG. 6B: Electrophysiological properties of WT and RTT neurons. From top to bottom: Transient Na+ currents and sustained K+ currents in response to voltage step depolarizations (command voltage varied from −20 to +30 mV in 5 mV increments when cells were voltage-clamped at −70 mV, Bars=400 pA and 50 ms). Action potentials evoked by somatic current injections (cells current-clamped at around −60 mV, injected currents from 10 to 40 pA, Bars=20 mV and 100 ms), sEPSCs (Bars=right, 20 pA, 100 ms; left: 10 pA, 500 ms), and sIPSCs (Bars=right, 20 pA, 500 ms; left: 20 pA, 400 ms).
Figure 6C:
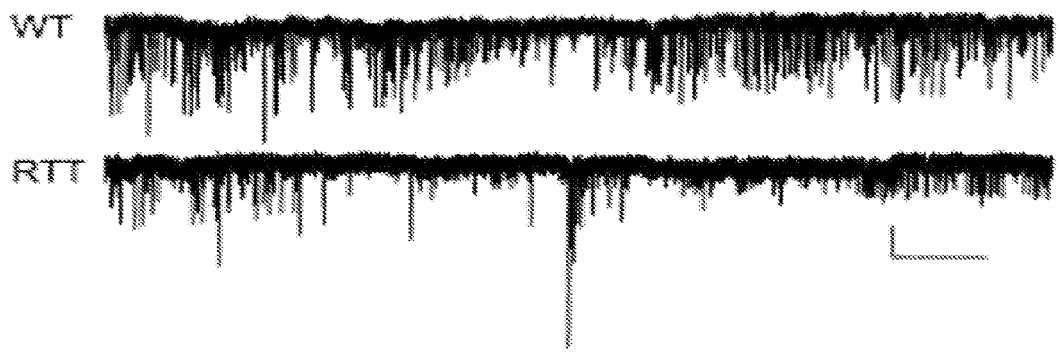
FIG. 6C: Sample 4-min recordings of spontaneous currents in WT (upper) and RTT (lower) when the cells were voltage-clamped at −70 mV (Bars=20 pA and 25 s).
Figure 6D:
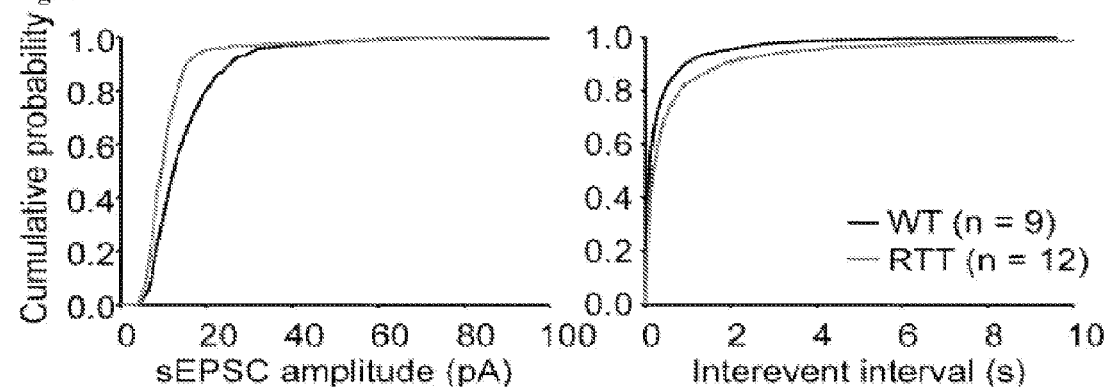
FIG. 6D: Cumulative probability plot of amplitudes (left panel, 1 pA bins; $p<0.001$) and inter-event intervals (right panel, 20 ms bins; $p<0.05$) of sEPSCs from groups of WT and RTT cells, respectively.
Figure 6E:
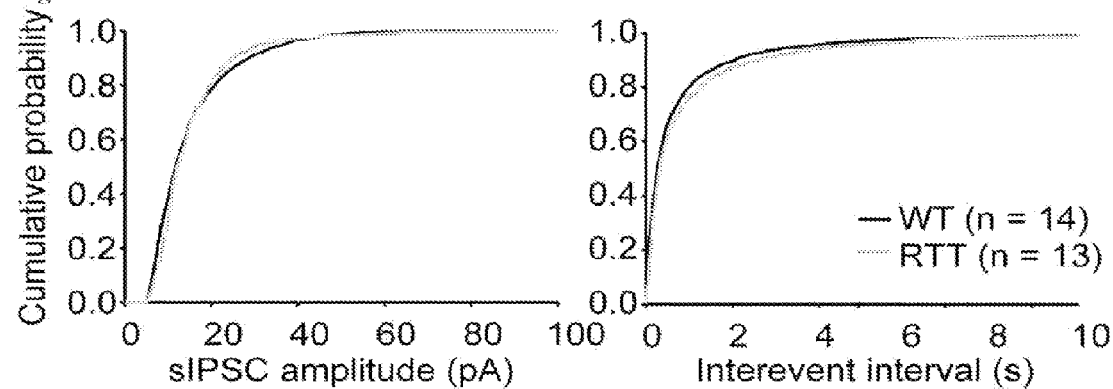
FIG. 6E: Cumulative probability plot of amplitudes (left panel, 1 pA bins; $p<0.05$) and inter-event intervals (right panel, 20 ms bins; $p<0.05$) of sIPSCs from each group (WT and RTT).

The functional maturation of the iPSC-derived neurons was further determined using electrophysiological methods. Whole-cell recordings were performed from cells that had differentiated for at least 6 weeks in culture. Neurons were visualized by infection with the Syn::EGFP viral vector. See FIG. 6A. Both WT and RTT neurons showed similar transient sodium inward currents, sustained potassium outward currents in response to voltage step depolarizations, and action potentials evoked by somatic current injections. See FIG. 6B. Therefore, the data indicate that WT and RTT reprogramming did not affect the ability of WT-iPSC- and RTT-iPSC-derived neurons to mature and become electrophysiologically active. Spontaneous excitatory and inhibitory postsynaptic currents (sEPSCs and sIPSCs) were recorded as a way of measuring intercellular connectivity and network formation. See FIGS. 6B-6C. Cumulative probability plots of amplitudes and inter-event intervals of spontaneous postsynaptic currents revealed that RTT neurons have a significant decrease in frequency and amplitude when compared to WT neurons. See FIGS. 6D-6E. Together, our data suggest that the neuronal network is altered in RTT iPSC-derived cultures.

Discussion

The lack of detectable symptoms in female RTT patients until 6-18 months of age and the apparent phenotypic reversibility of some RTT phenotypes in MeCP2 knockout animals indicate that MeCP2 is not essential for early wiring of the nervous system but instead may only be required at late stages. It is possible that RTT patients have aberrant excitatory synaptic strength at very early stages, when the disease phenotype is not yet clearly observed. In fact, increasing evidence from clinical studies and mouse models indicates the presence of alterations during the so-called pre-symptomatic developmental phase. See e.g., Charman et al., 2002, *Brain Dev* 24:281-283; De Filippis et al., 2010, *Genes Brain Behav* 9:213-233; Kerr et al., 1987, *Brain Dev* 9:487-490; Picker et al., 2006, *Neuroreport* 17:541-544; Santos et al., 2007, *Genes Brain Behav* 6:277-286.

To study human RTT neurons in culture, we derived iPSCs from RTT fibroblasts. RTT iPSCs are pluripotent and able to recapitulate X-inactivation upon neuronal differentiation. Even though the ratio of neurons expressing mutant MeCP2 due to X-inactivation was variable, the phenotypes described here for all RTT-derived neurons are similar. One interpretation could be that astrocytes, or other non-neuronal cells, carrying MeCP2 mutations present in our cultures could also affect neurons expressing the normal MeCP2 protein. In fact, the non-cell autonomous influence was recently described for RTT, indicating that glial cells carrying MeCP2 mutations can distress healthy neurons. See e.g., Ballas et al., 2009, *Nat Neurosci* 12:311-317; Kishi & Macklis, *Exp Neurol* 222:51-58; Maezawa et al., 2009, *J Neurosci* 29:5051-5061.

Using human neurons carrying MeCP2 mutations, we showed that RTT glutamatergic neurons have a reduced number of synapses and dendritic spines when compared to non-affected controls. Moreover, electrophysiological recordings from RTT neurons showed a significant decrease in the frequency and amplitude of spontaneous synaptic currents compared to WT neurons. The reduced frequency in RTT neurons could reflect the presence of fewer release sites or a decreased release probability. The results of electrophysiology recordings are consistent with the decreased V-GLUT1 puncta observed in Map2-positive dendrites from RTT neurons. Also consistent with these findings, the frequency of intracellular calcium transients was decreased in RTT neurons when compared to controls. Our data indicate a potential imbalance in the neuronal networks associated with RTT pathology. The observations described here provide valuable information for RTT and, potentially, ASD patients, since they suggest that pre-symptomatic defects may represent novel biomarkers to be exploited as diagnostic tools and that early intervention may be beneficial.

Therapies aiming at earlier stages of development may attenuate the downstream consequences of MeCP2 mutations. Restoring protein levels may be challenging, since MeCP2 levels are tightly regulated and chronically overdosing neurons with the WT allele can be as harmful as a loss of expression. See e.g., Collins et al., 2004, *Hum Mol Genet* 13:2679-2689; Ramocki et al., 2009, *Ann Neurol* 66:771-782; Van Esch et al., 2005, *Am J Hum Genet* 77:442-453. Thus, we tested pharmacological treatment as a way to recover the RTT neuronal phenotype. We investigated the use of IGF1 in human neuronal cultures. Without wishing to be bound by any theory, IGF1 is considered to be a candidate for pharmacological treatment of RTT and potentially other CNS disorders in a future clinical trial. See Tropea et al., *Id*. While IFG1 treatment increased synapse number in some clones, it stimulated glutamatergic RTT neurons above normal levels. Our data indicate that the IGF1 dose and timing parameters need to be precisely tuned in future clinical trials to avoid side effects. In a different approach, we tested a read-through drug (gentamicin) to rescue neurons derived from iPSCs carrying a nonsense MeCP2 mutation. A lower dosage of gentamicin was enough to increase full-length MeCP2 levels in RTT neurons, rescuing glutamatergic synapses.

The gain and loss of function data provided herein strongly suggest that MeCP2 is indeed the causative agent of the cellular phenotypes reported here that might be relevant to the clinical features of RTT. Indeed, the present data indicate that iPSCs not only can recapitulate some aspects of a genetic disease but also can be used to better design and anticipate results from translational medicine. This cellular model has the potential to lead to the discovery of new compounds to treat RTT and other forms of ASD. Finally, without wishing to be bound by any theory, it is believed that other CNS diseases may be modeled in vitro using a similar approach.

In summary, we have developed a human model of RTT by generating iPSCs from fibroblasts of RTT patients carrying different MeCP2 mutations and unaffected individuals. We show that RTT-iPSCs retain the capacity to generate proliferating neural progenitor cells (NPCs) and functional neurons that undergo X-inactivation. We observed a reduced number of dendritic spines and synapses in iPSC-derived neurons. Moreover, we detected an altered frequency of intracellular calcium spikes and electrophysiological defects in RTT-derived neuronal networks, revealing new biomarkers for RTT pathology. Gain and loss of function experiments in iPSC-derived neurons confirmed that some of the alterations observed were related to MeCP2 expression levels. Finally, we used the iPSC system to test candidate drugs to rescue synaptic deficiency in RTT neurons. Without wishing to be bound by any theory, it is believed that RTT and other complex CNS diseases can be modeled using iPSC technology to investigate the cellular and molecular mechanisms underlying their abnormalities.

What is claimed is:

1. An in vitro method for preparing an X chromosome inactivated female human neuronal cell comprising introducing nucleic acids encoding Oct4, c-Myc, Klf4 and Sox2 proteins into a somatic cell derived from a female human subject with Rett syndrome, wherein the cell comprises a mutated endogenous MeCP2 gene, wherein the nucleic acids are comprised in one or more retroviral vectors, wherein the proteins are expressed by the cell thereby generating an induced pluripotent stem cell (iPSC), culturing the iPSC under human embryonic stem cell (hESC) culture conditions, identifying and isolating an iPSC comprising two active X chromosomes, differentiating the iPSC comprising two active X chromosomes into a neuronal cell in vitro, wherein the neuronal cell exhibits a reduction in the frequency of intracellular calcium transients or the transient rise of intracellular calcium levels, and a decrease in the frequency and amplitude of spontaneous excitatory and inhibitory postsynaptic currents, compared to a control cell without the mutated endogenous MeCP2 gene, wherein upon differentiation one of the two active X chromosomes is inactivated, selecting a neuronal cell comprising an active X chromosome comprising the mutated MeCP2 gene, and determining the neural functionality of the neuronal cell.

2. The method of claim 1, wherein said human female somatic cell comprises a first X chromosome and a second X chromosome, wherein said first X chromosome is active and said second X chromosome is inactive, and wherein said second X chromosome comprises the mutated MeCP2 gene.

3. An in vitro method for preparing an X chromosome inactivated female human neural cell comprising introducing nucleic acids encoding Oct4, c-Myc, Klf4 and Sox2 proteins into a somatic cell derived from a female human subject with Rett syndrome, wherein the cell comprises a mutated endogenous MeCP2 gene, wherein the nucleic acids are comprised in one or more retroviral vectors, wherein the proteins are expressed by the cell thereby generating an induced pluripotent stem cell (iPSC), culturing the iPSC under human embryonic stem cell (hESC) culture conditions, identifying and isolating an iPSC comprising two active X chromosomes, differentiating the iPSC comprising two active X chromosomes into a neural cell in vitro, wherein the neural cell exhibits a reduction in the frequency of intracellular calcium transients or the transient rise of intracellular calcium levels, and a decrease in the frequency and amplitude of spontaneous excitatory and inhibitory postsynaptic currents, compared to a control cell without the mutated endogenous MeCP2 gene, wherein upon differentiation one of the two active X chromosomes is inactivated, and selecting a neural cell comprising an active X chromosome comprising the mutated MeCP2 gene.

4. The method of claim 3, wherein said human female somatic cell comprises a first X chromosome and a second X chromosome, wherein said first X chromosome is active and said second X chromosome is inactive, and wherein said second X chromosome comprises the mutated MeCP2 gene.

* * * * *